US006902744B1

(12) United States Patent
Kolterman et al.

(10) Patent No.: US 6,902,744 B1
(45) Date of Patent: Jun. 7, 2005

(54) EXENDIN AGONIST FORMULATIONS AND METHODS OF ADMINISTRATION THEREOF

(75) Inventors: Orville G. Kolterman, Poway, CA (US); Andrew A. Young, La Jolla, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/889,330

(22) PCT Filed: Jan. 14, 2000

(86) PCT No.: PCT/US00/00902

§ 371 (c)(1),
(2), (4) Date: Dec. 27, 2001

(87) PCT Pub. No.: WO00/41546

PCT Pub. Date: Jul. 20, 2000

Related U.S. Application Data

(60) Provisional application No. 60/175,365, filed on Jan. 10, 2000, and provisional application No. 60/116,380, filed on Jan. 14, 1999.

(51) Int. Cl.$^7$ .................................................. A61K 9/14
(52) U.S. Cl. ........................ 424/489; 424/278.1; 514/2; 514/3; 514/4; 514/12; 514/866; 530/300
(58) Field of Search ............................ 424/489, 278.1; 514/2, 3, 4, 12, 866; 530/300

(56) References Cited

U.S. PATENT DOCUMENTS

| 5,424,286 | A | 6/1995 | Eng | |
|---|---|---|---|---|
| 6,506,724 | B1 | * 1/2003 | Hiles et al. | ..................... 514/2 |
| 6,528,486 | B1 | * 3/2003 | Larsen et al. | ................. 514/12 |
| 2003/0087821 | A1 | 5/2003 | Beeley et al. | |

FOREIGN PATENT DOCUMENTS

| WO | WO 97/46584 | 12/1997 | | |
|---|---|---|---|---|
| WO | WO 98/08871 | 3/1998 | | |
| WO | WO 98/30231 | 7/1998 | | |
| WO | WO 9830231 | * 7/1998 | .......... | A61K/38/16 |
| WO | WO 99/07404 | 2/1999 | | |
| WO | WO 99/25727 | 5/1999 | | |
| WO | WO 99/25728 | 5/1999 | | |
| WO | WO 99/40788 | 8/1999 | | |
| WO | WO 99/43708 | 9/1999 | | |

OTHER PUBLICATIONS

Amylin Pharmaceuticals, Inc., Form 10–K Annual Report Pursuant to Section 13 or 15(d) of the Securities Exchange Act of 1934, Mar. 15, 2002, pp. 1–8.
Baggio et al., "Sustained Expression of Exendin–4 Does Not Perturb Glucose Homeostasis, β–Cell Mass, or Food Intake in Metallothionein–Preproexendin Transgenic Mice," *J. Biol. Chem.* 275(44):34471–7 (2000).
Edwards et al., "Exendin–4 Reduces Fasting and Postprandial Glucose and Decreases Energy Intake in Healthy Volunteers," *Am. J. Physiol. Endocrinol. Metab.* 281:E155–61 (2001).
Egan et al., "The Insulinotropic Effect of Acute Exendin–4 Administered to Humans: Comparison of Nondiabetic State to Type 2 Diabetes," *J. Clin. Endocrinol. & Metab.* 87(3):1282–90 (2002).
Goke et al., "Exendin–4 Is a High Potency Agonist and Truncated Exendin–(9–39)–amide an Antagonist at the Glucagon–like Peptide 1–(7–36)–amide Receptor of Insulin–secreting β–Cells," *J. Biol. Chem.* 268(26):19650–55 (1993) (previously submitted on Aug. 20, 2002).
International Search Report, International Application No. PCT/US03/16699 (Aug. 2003).
Tourrel et al., "Persistent Improvement of Type 2 Diabetes in the Goto–Kakizaki Rat Model by Expansion of the β–Cell Mass During the Prediabetic Period with Glucagon–Like Peptide–1 or Exendin–4," *Diabetes* 51:1443–52 (2002).
Bhavsar et al., "Inhibition of Gastric Emptying and of Food Intake Appear to be Independently Controlled in Rodents," 25$^{th}$ Annual Meeting, Nov. 11–16, 1995, San Diego, California, *Soc. Neurosci.*, 21:460 (Abstract) (188.8).
D'Alessio et al., "Elimination of the Action of Glucagon–like Peptide 1 Causes an Impairment of Glucose Tolerance after Nutrient Ingestion by Healthy Baboons," *J. Clin. Invest.*, 97(1):133–38 (1996).
Daniel et al., "Use of Glucagon in the Treatment of Acute Diverticultis," *British Medical Journal*, 3:720–2 (1974).
Eissele et al., "Rat Gastric Somatostatin and Gastrin Release: Interactions of Exendin–4 and Truncated Glucagon–Like Peptide–1 (GLP–1) Amide," *Life Sci.*, 55(8):629–34 (1994).
Eng, "Prolonged Effect of Exendin–4 on Hyperglycemia of db/db Mice," *Diabetes*, 45(Supp 2):152A (abstract 554) (1996).
Eng et al., "Purification and Structure of Exendin–3, a New Pancreatic Secretagogue Isolated from *Heloderma horridum* Venom," *J. Biol. Chem.*, 265(33):20259–62 (1990).
Eng et al., "Isolation and Characterization of Exendin–4, an Exendin–3 Analogue, from *Heloderma suspectum* Venom," *J. Biol. Chem.*, 267(11):7402–5 (1992).
Glauser et al.,"Intravenous Glucagon in the Management of Esophageal Food Obstruction," *J. Am. Coll. Emer. (JACEP)*, 8(6):228–231 (1979).

(Continued)

Primary Examiner—Karen Cochrane Carlson
Assistant Examiner—Samuel Wei Liu
(74) Attorney, Agent, or Firm—Arnold & Porter, LLP

(57) ABSTRACT

Novel exendin and exendin agonist compound formulations and dosages and methods of administration thereof are provided. These compositions and methods are useful in treating diabetes and conditions that would be benefited by lowering plasma glucose or delaying and/or slowing gastric emptying or inhibiting food intake.

42 Claims, 25 Drawing Sheets

OTHER PUBLICATIONS

Goke et al., "Exendin–4 Is a High Potency Agonist and Truncated Exendin–(9–39)–amide an Antagonist at the Glucagon–like Peptide 1–(7–36)–amide Receptor of Insulin–secreting β–Cells," *J. Biol. Chem.*, 268(26):19650–55 (1993).

Kolligs et al., "Reduction of the Incretin Effect in Rats by the Glucagon–Like Peptide 1 Receptor Antagonist Exendin(9–39) Amide," *Diabetes*, 44:16–19 (1995).

Montrose–Rafizadeh et al., Structure–function Analysis of Exendin–4 /.

O'Halloran et al., "Glucagon–like Peptide–1 (7–36)–NH$_2$: a Physiological Inhibitor of Gastric Acid Secretion in Man," *J. Endocrinol.*, 126(1):169–73 (1990).

Ørskov et al., "Biological Effects and Metabolic Rates of Glucagonlike Peptide–1 7–36 Amide and Glucagonlike Peptide–1 7–37 in Healthy Subjects Are Indistinguishable," *Diabetes*, 42:658–61 (1993).

Raufman et al., "Exendin–3, a Novel Peptide from *Heloderma horridum* Venom, Interacts with Vasoactive Intestinal Peptide Receptors and a Newly Described Receptor on Dispersed Acini from Guinea Pig Pancreas," *J. Biol. Chem.*, 266(5):2897–902 (1991).

Raufman et al., "Truncated Glucagon–like Peptide–1 Interacts with Exendin Receptors in Dispersed Acini from Guinea Pig Pancreas", *J. Biol. Chem.* 267(30):21432–37 (1992).

Schepp et al., "Exendin–4 and Exendin–(9–39)NH$_2$: Agonist and Antagonist, Respectively, at the Rat Parietal Cell Receptor for Glucagon–like Peptide–1–(7–36)NH$_2$," *Eur. J. Pharm.*, 269:183–91 (1994).

Schjoldager et al., "GLP–1 (Glucagon–like Peptide 1) and Truncated GLP–1, Fragments of Human Proglucagon, Inhibit Gastric Acid Secretion in Humans," *Digest. Dis. Sci.*, 34(5):703–8 (1989).

Stower et al., "A Trial of Glucagon in the Treatment of Painful Biliary Tract Disease," *Brit. J. Surg.*, 69:591–2 (1982).

Thorens et al., "Cloning and Functional Expression of the Human Islet GLP–1 Receptor," *Diabetes*, 42(11):1678–82 (1993).

Thorens, "Expression Cloning of the Pancreatic β Cell Receptor for the Gluco–incretin Hormone Glucagon–like Peptide 1," *P. Natl. Acad. Sci. USA*, 89:8641–45 (1992).

Turton et al., "A Role for Glucagon–like Peptide–1 in the Central Regulation of Feeding," *Nature*, 379(6560):69–72 (1996).

Wang et al., "Glucagon–like Peptide–1 Is a Physiological Incretin in Rat," *J. Clin. Invest.*, 95:417–21 (1995).

Wettergren et al., "Truncated GLP–1 (Proglucagon 78–107–Amide) Inhibits Gastric and Pancreatic Functions in Man," *Digest. Dis. Sci.*, 38(4):665–73 (1993).

Willms et al., "Gastric Emptying, Glucose Responses, and Insulin Secretion after a Liquid Test Meal: Effects of Exogenous Glucagon–Like Peptide–1 (GLP–1)–(7–36) Amide in Type 2 (Noninsulin–Dependent) Diabetic Patients," *J. Clin. Endocrinol. Metab.*, 81(1):327–32 (1996).

* cited by examiner

EXENDIN-3

His Ser Asp Gly Thr Phe Thr Ser Asp Leu Ser Lys Gln Met Glu Glu
1          5                    10                  15
Glu Ala Val Arg Leu Phe Ile Glu Trp Leu Lys Asn Gly Gly Pro Ser
            20              25                  30
Ser Gly Ala Pro Pro Pro Ser$_2$NH
        35

Fig. 1

EXENDIN-4

His Gly Glu Gly Thr Phe Thr Ser Asp Leu Ser Lys Gln Met Glu Glu
             5                   10                  15
Glu Ala Val Arg Leu Phe Ile Glu Trp Leu Lys Asn Gly Gly Pro Ser
            20              25                  30
Ser Gly Ala Pro Pro Pro Ser-NH$_2$
        35

Fig. 2

GLP-1 (GLP-1[7-36] NH$_2$)

His Ala Glu Gly Thr Phe Thr Ser Asp Val Ser Ser Tyr Leu Glu Gly
            5                            10                     15
Gln Ala Ala Lys Glu Phe Ile Ala Trp Leu Val Lys Gly Arg-NH$_2$
        20                 25               30

Fig. 3

Male rats (350-400g) fasted overnight were cannulated in the trachea and femoral artery under anesthesia.
Blood was drawn from the arterial line before and after (5, 15, 30, 45, 60 and 75 min) 20μg of exendin-4 dissolved in 50μL saline was administered into the trachea of each rat. Plasma exendin-4 levels were determined with an immunoradiometric assay.

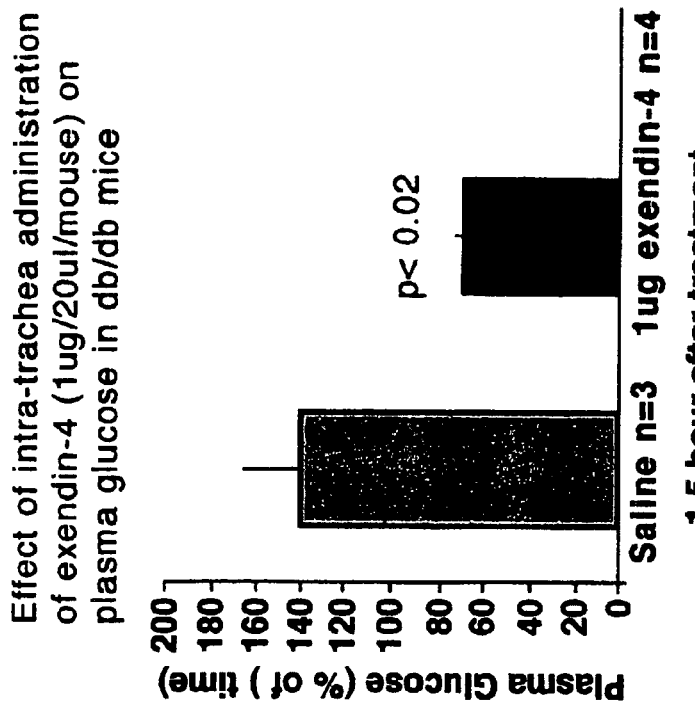
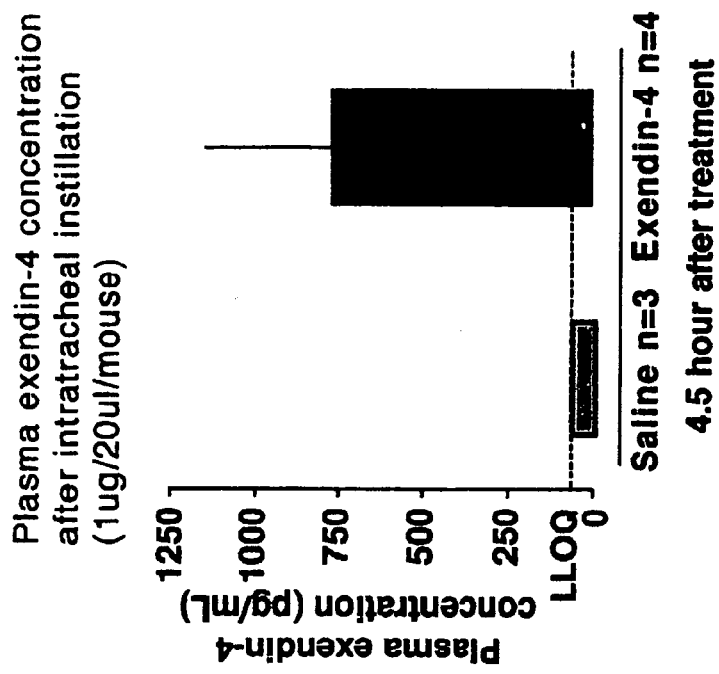
Male db/db mice (approx 50g) were fasted for 2h, and the trachea was intubated under anesthesia. The animals were bled (75 μL, orbital sinus) before and after 20 μL of saline or 1μg exendin-4 dissolved in saline was administered into the trachea of each animal.

Plasma exendin-4 concentrations in rat exposed to aerosolized exendin-4(8ng/ml) for 10 minutes

Male rats (approximately 350g each) fasted overnight were placed in a 2 litre chamber and exposed to aerosolized exendin-4 for 10 minutes.

Exendin-4 was nebulized at a rate of 0.2mg/min at a flow rate of 5L/min.

The concentration of aerosolized exendin-4 was estimated from samples of chamber atmosphere drawn during the course of the experiment.

Fig. 8

Effect of 10 minutes of exposure to aerosolized exendin-4 (8ug/ml) on plasma glucose in db/db mice Plasma glucose (% of 0 time)

$p < 0.0001$ saline n=11    exendin-4 n=11

1 hour after treatment

Fig. 9A

Plasma exendin-4 concentration after 10 minute exposure to aerosolized saline or exendin-4 (8ng/ml atmosphere)

Plasma exendin-4 (pg/ml)

saline n=11    exendin-4 n=11

1 hour after treatment

Fig. 9B

Harlan Sprague Dawley rats 311-365g, nonfasted, were dosed with 0, 1, 100µg of exendin-4 in 2µl of saline by application in to the nostrils.
Blood samples from anesthetized (Hurricane) tail tip were collected at 0, 3,10, 20, 30 and 60 min after dosing for exendin-4 plasma level measured by IRMA.

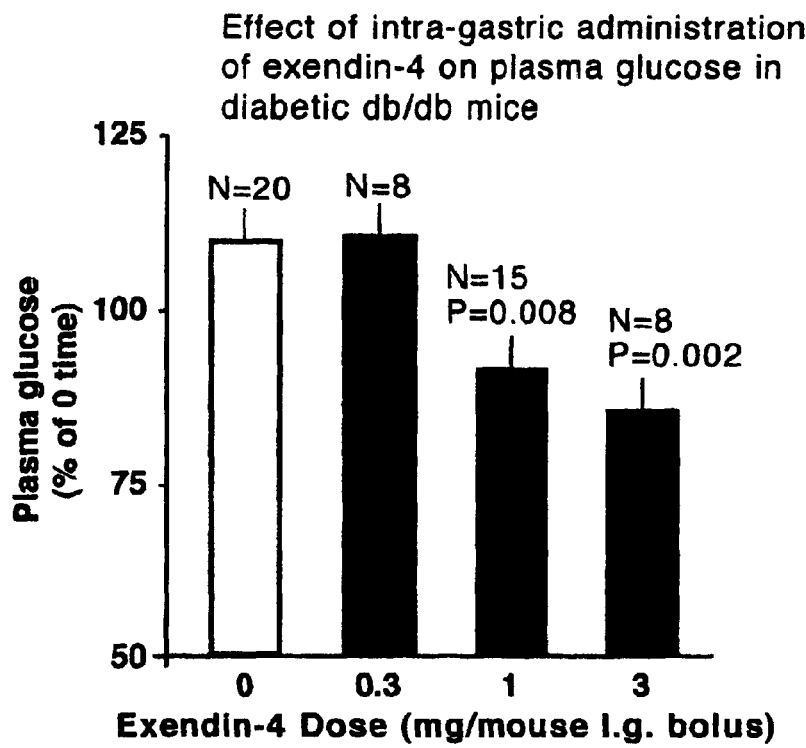

Male db/db mice (approx 50g) were fasted for 2h and bled (40μl, orbital sinus) before and 1h after 200 μl of saline or exendin-4 dissolved in saline was administered i.g. into each animal.

*Sublingual*

Sublingual application of exendin-4 (100μg/5 μL/animal) to diabetic db/db mice led to a 15% decrease in plasma glucose concentration one hour after treatment. A 30% increase was observed for the control group receiving saline. The mean exendin-4 plasma level at 60min was 4520±1846 pg/mL (see Figure 8).

Fig. 11

Plasma Concentration after Sublingual Administration of AC2993 in Rats

Dose-was given in 3μL saline under the tongue in HSD rats (~300g) briefly anesthetized with metophane.

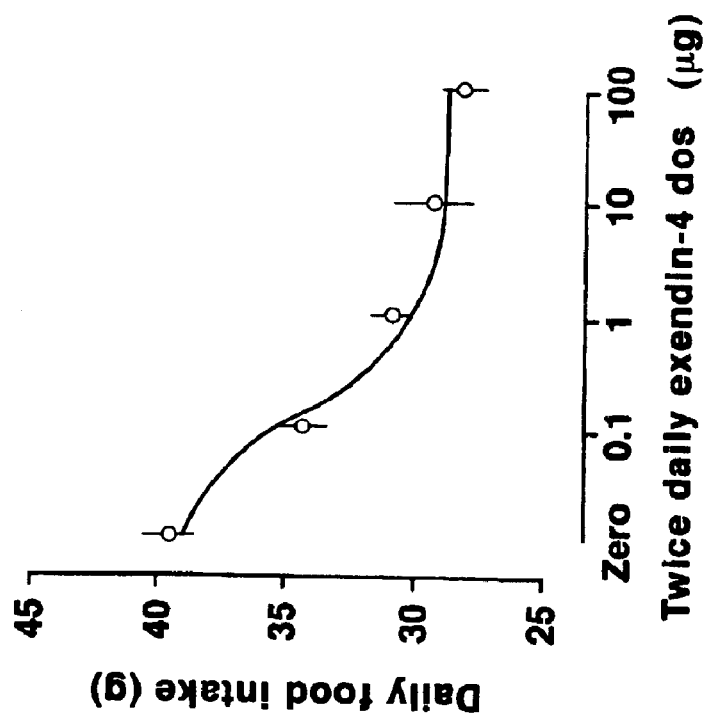
Fig. 13A2
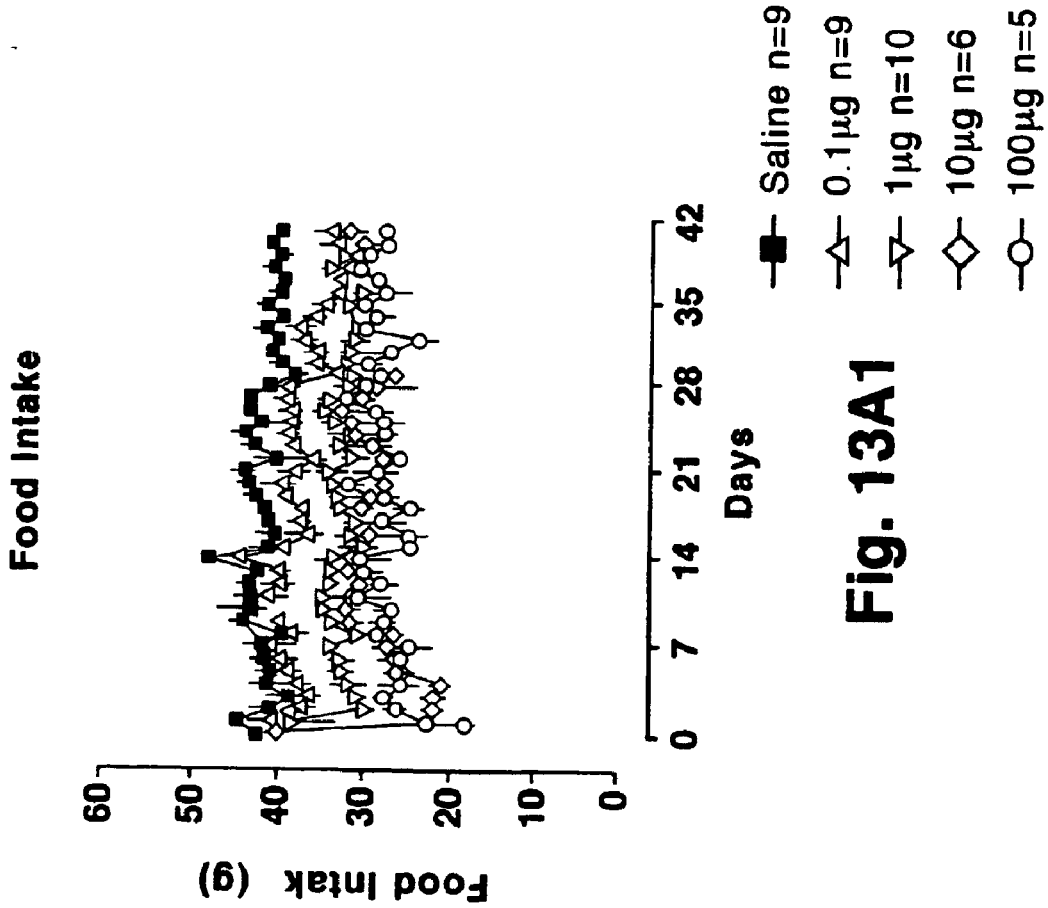
Fig. 13A1

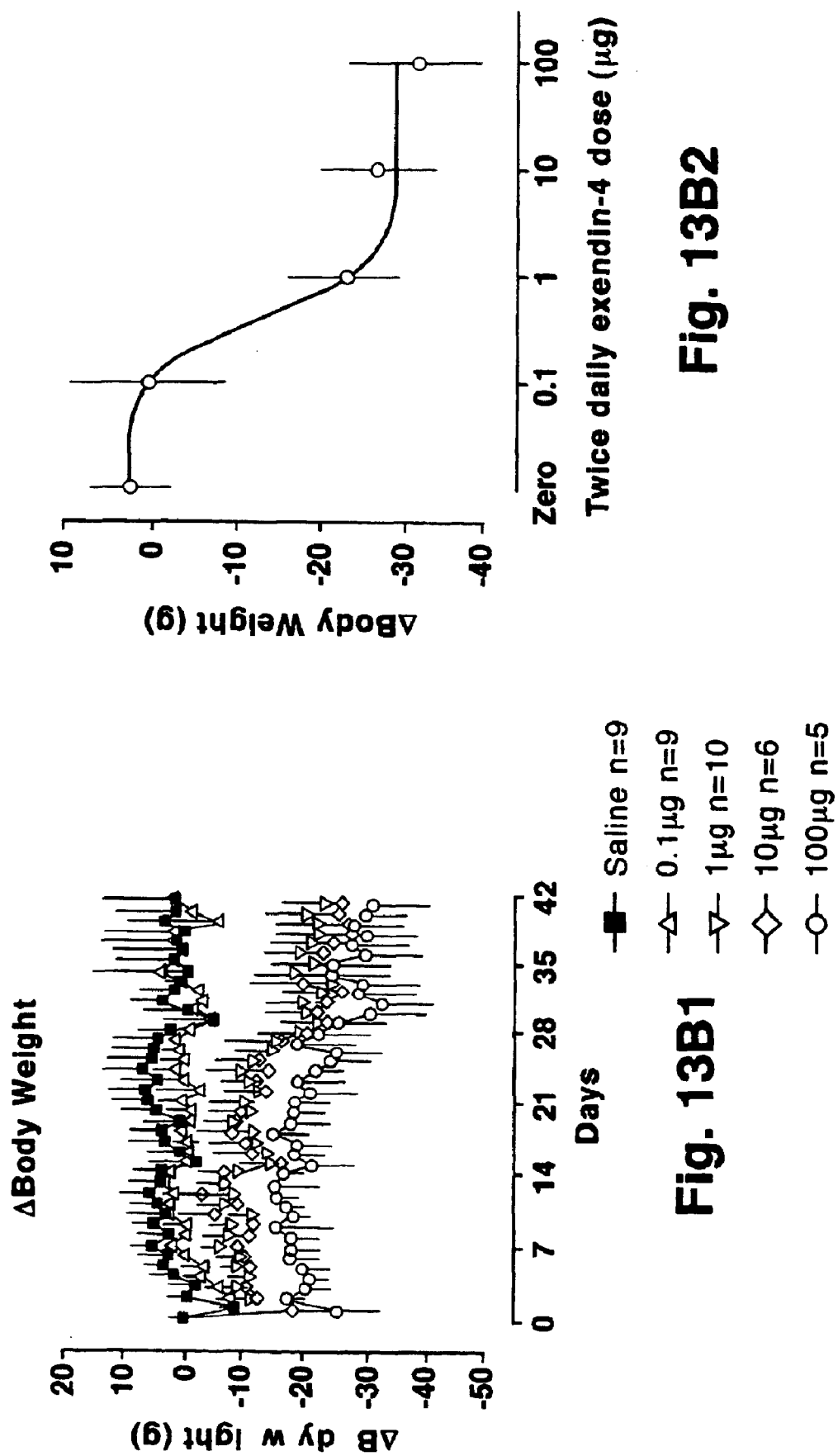
Fig. 13B2
Fig. 13B1

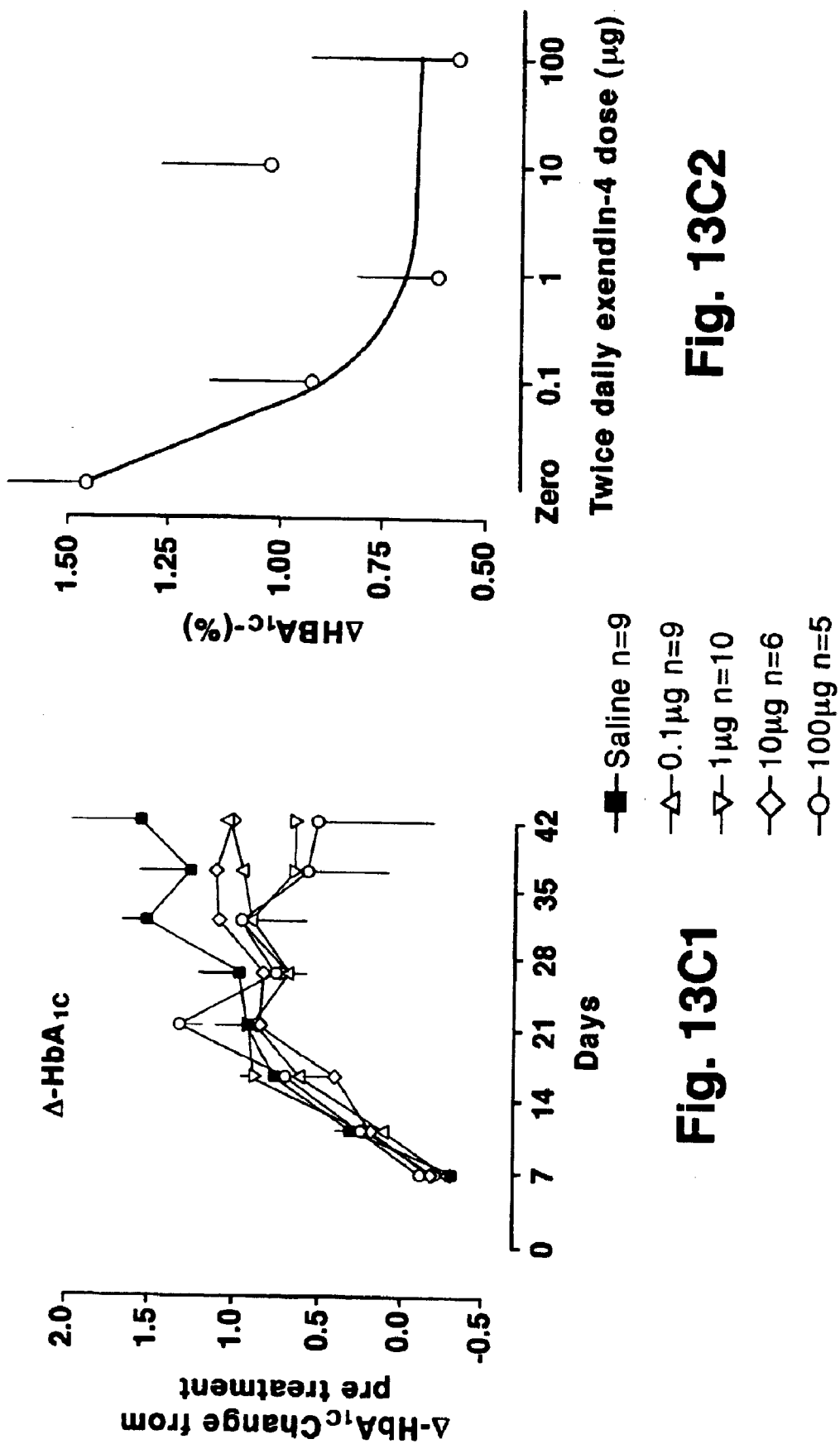
Fig. 13C2
Fig. 13C1

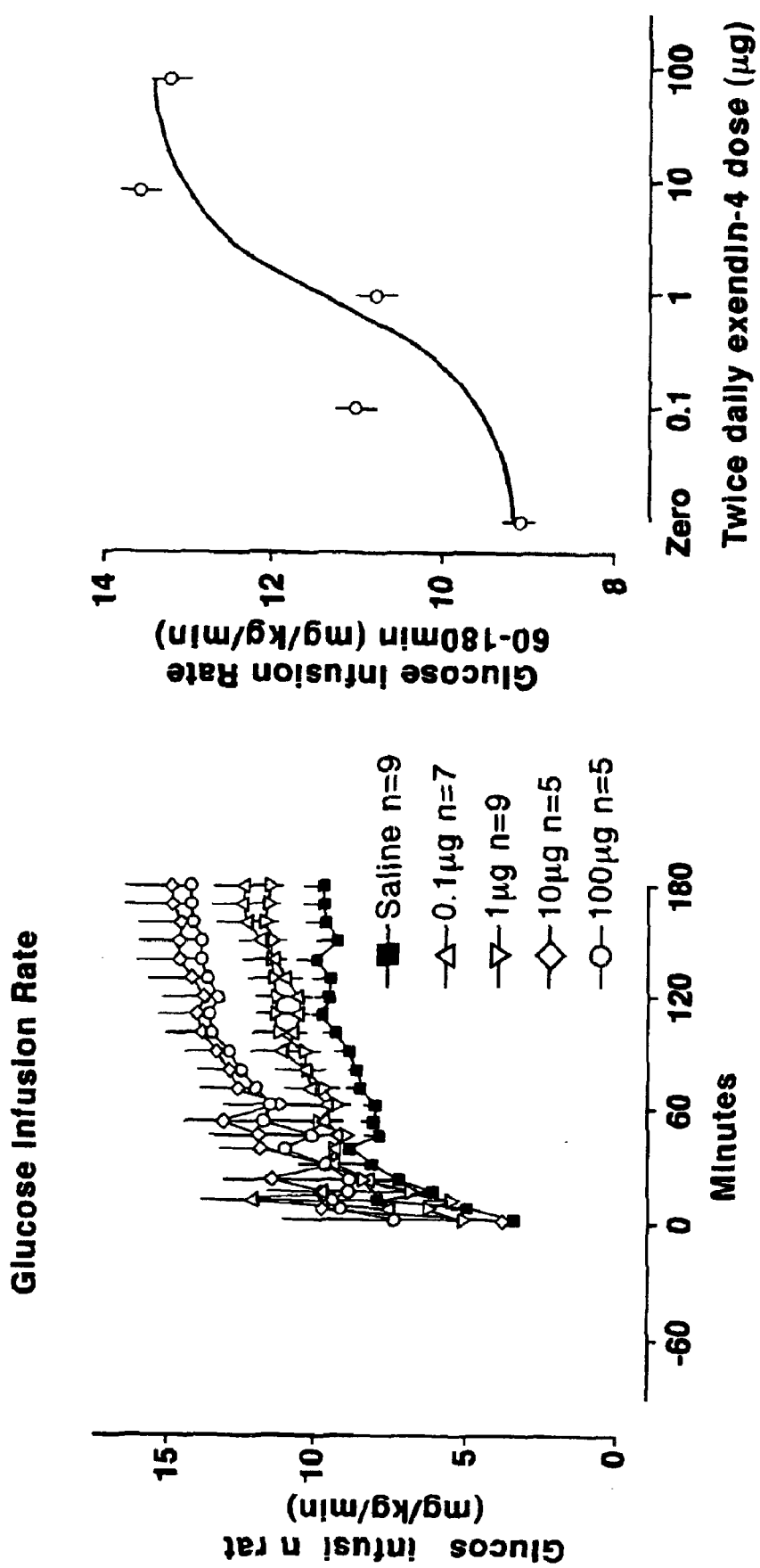
Fig. 14B2
Fig. 14B1

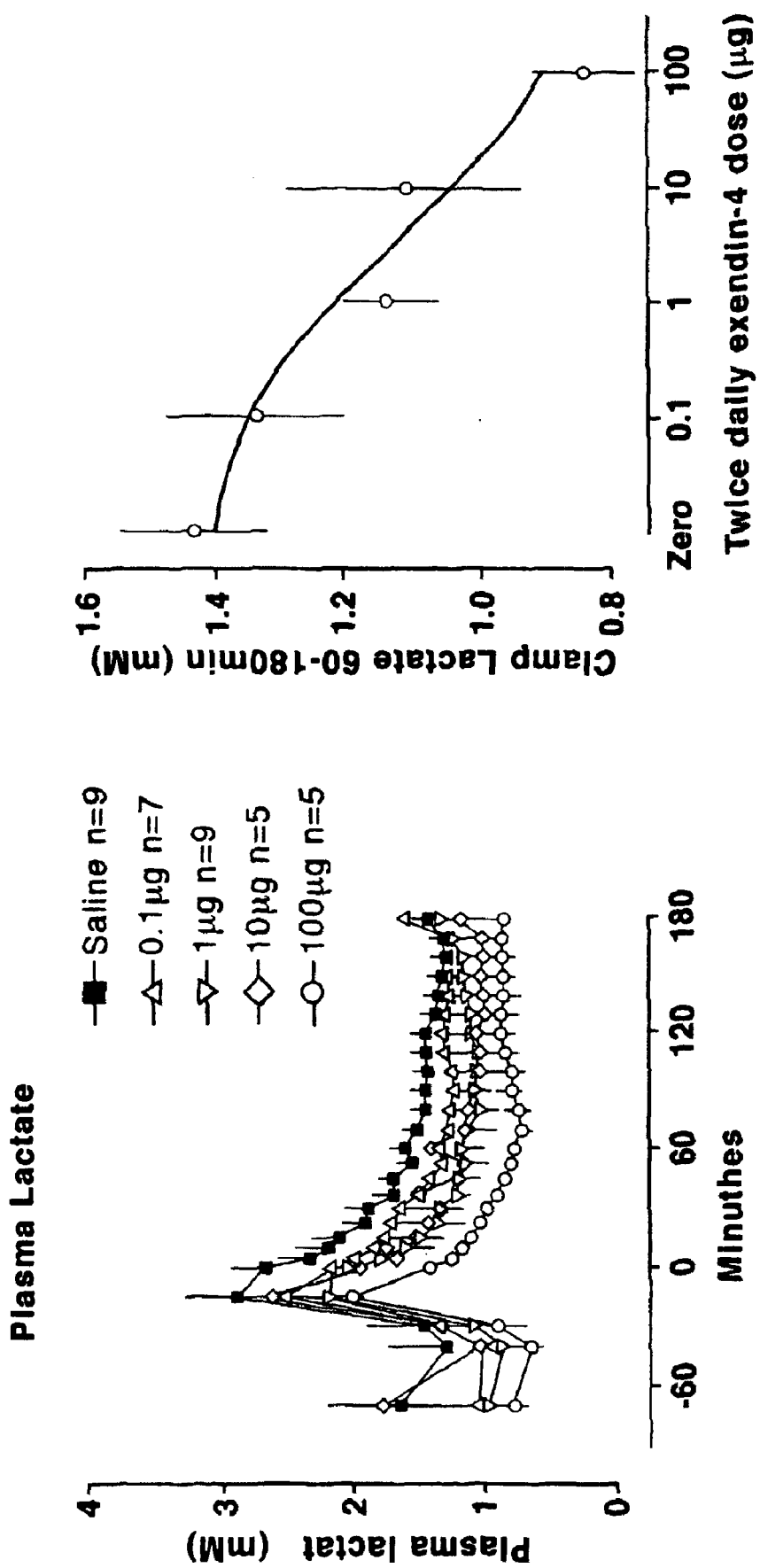

Xaa₁ Xaa₂ Xaa₃ Gly Thr Xaa₄ Xaa₅ Xaa₆ Xaa₇ Xaa₈ Ser Lys Gln Xaa₉ Glu Glu Ala Val Arg Leu
Xaa₁₀ Xaa₁₁ Xaa₁₂ Xaa₁₃ Leu Lys Asn Gly Gly Xaa₁₄ Ser Ser Gly Ala Xaa₁₅ Xaa₁₆ Xaa₁₇ Xaa₁₈-Z

| [SEQ. ID. NO.] | Xaa₁ | Xaa₂ | Xaa₃ | Xaa₄ | Xaa₅ | Xaa₆ | Xaa₇ | Xaa₈ | Xaa₉ | Xaa₁₀ | Xaa₁₁ | Xaa₁₂ | Xaa₁₃ | Xaa₁₄ | Xaa₁₅ | Xaa₁₆ | Xaa₁₇ | Xaa₁₈ |
|---|---|---|---|---|---|---|---|---|---|---|---|---|---|---|---|---|---|---|
| 9  | His | Gly | Glu  | Phe  | Thr | Ser | Asp | Leu  | Leu  | Phe  | Ile | Glu | Phe | Pro | Pro | Pro | Pro | Ser |
| 10 | His | Gly | Glu  | Phe  | Thr | Ser | Asp | Leu  | Leu  | Phe  | Ile | Glu | Trp | Pro | Pro | Pro | Pro | Ser |
| 11 | His | Gly | Glu  | Phe  | Thr | Ser | Asp | Leu  | Met  | Phe  | Ile | Glu | Phe | Pro | Pro | Pro | Pro | Ser |
| 12 | Tyr | Gly | Glu  | Phe  | Thr | Ser | Asp | Leu  | Met  | Phe  | Ile | Glu | Trp | Pro | Pro | Pro | Pro | Tyr |
| 13 | His | Gly | Glu  | Phe  | Thr | Ser | Asp | Leu  | Leu  | Phe  | Ile | Glu | Trp | Pro | Pro | Pro | Pro | Ser |
| 14 | His | Gly | Asp  | Phe  | Thr | Ser | Asp | Leu  | Met  | Phe  | Ile | Glu | Trp | Pro | Pro | Pro | Pro | Ser |
| 15 | His | Gly | Glu  | naph | Thr | Ser | Asp | Leu  | Met  | Phe  | Ile | Glu | Trp | Pro | Pro | Pro | Pro | Ser |
| 16 | His | Gly | Glu  | Phe  | Ser | Ser | Asp | Leu  | Met  | Phe  | Ile | Glu | Trp | Pro | Pro | Pro | Pro | Ser |
| 17 | His | Gly | Glu  | Phe  | Ser | Thr | Glu | Leu  | Leu  | Phe  | Ile | Glu | Trp | Pro | Pro | Pro | Pro | Ser |
| 18 | His | Gly | Glu  | Phe  | Thr | Ser | Asp | Leu  | Leu  | Met  | Ile | Glu | Trp | Pro | Pro | Pro | Pro | Ser |
| 19 | His | Gly | Glu  | Phe  | Thr | Ser | Asp | Leu  | Leu  | Phe  | Ile | Glu | Trp | Pro | Pro | Pro | Pro | Ser |
| 20 | His | Gly | Glu  | Phe  | Thr | Ser | Asp | pGly | Met  | Phe  | Ile | Glu | Trp | Pro | Pro | Pro | Pro | Ser |
| 21 | His | Gly | Glu  | Phe  | Thr | Ser | Asp | pGly | Leu  | Phe  | Ile | Glu | Phe | Pro | Pro | Pro | Pro | Ser |
| 22 | His | Gly | Glu  | Phe  | Thr | Ser | Asp | Leu  | pGly | Phe  | Ile | Glu | Trp | Pro | Pro | Pro | Pro | Ser |
| 23 | His | Gly | Glu  | Phe  | Thr | Ser | Asp | Leu  | pGly | Phe  | Ile | Glu | Phe | Pro | Pro | Pro | Pro | Ser |
| 24 | His | Gly | Glu  | Phe  | Thr | Ser | Asp | Leu  | Met  | naph | Ile | Glu | Trp | Pro | Pro | Pro | Pro | Ser |
| 25 | His | Gly | Glu  | Phe  | Thr | Ser | Asp | Leu  | Met  | Phe  | Val | Glu | Trp | Pro | Pro | Pro | Pro | Ser |

Fig. 15A

| [SEQ. ID. NO.] | Xaa1 | Xaa2 | Xaa3 | Xaa4 | Xaa5 | Xaa6 | Xaa7 | Xaa8 | Xaa9 | Xaa10 | Xaa11 | Xaa12 | Xaa13 | Xaa14 | Xaa15 | Xaa16 | Xaa17 | Xaa18 |
|---|---|---|---|---|---|---|---|---|---|---|---|---|---|---|---|---|---|---|
| 26 | His | Gly | Glu | Phe | Thr | Ser | Asp | Leu | Leu | Phe | Val | Glu | Phe | Pro | Pro | Pro | Pro | Ser |
| 27 | His | Gly | Glu | Phe | Thr | Ser | Asp | Leu | Met | Phe | tBuG | Glu | Trp | Pro | Pro | Pro | Pro | Ser |
| 28 | His | Gly | Glu | Phe | Thr | Ser | Asp | Leu | Leu | Phe | tBuG | Glu | Phe | Pro | Pro | Pro | Pro | Ser |
| 29 | His | Gly | Glu | Phe | Thr | Ser | Asp | Leu | Met | Phe | Ile | Asp | Trp | Pro | Pro | Pro | Pro | Ser |
| 30 | His | Gly | Glu | Phe | Thr | Ser | Asp | Leu | Met | Phe | Ile | Glu | Phe | Pro | Pro | Pro | Pro | Ser |
| 31 | His | Gly | Glu | Phe | Thr | Ser | Asp | Leu | Met | Phe | Ile | Glu | Trp | tPro | tPro | tPro | tPro | Ser |
| 32 | His | Gly | Glu | Phe | Thr | Ser | Asp | Leu | Met | Phe | Ile | Glu | Trp | Pro | tPro | tPro | tPro | Ser |
| 33 | His | Gly | Glu | Phe | Thr | Ser | Asp | Leu | Met | Phe | Ile | Glu | Trp | hPro | hPro | hPro | hPro | Ser |
| 34 | His | Gly | Glu | Phe | Thr | Ser | Asp | Leu | Met | Phe | Ile | Glu | Phe | Pro | hPro | hPro | hPro | Ser |
| 35 | His | Gly | Glu | Phe | Thr | Ser | Asp | Leu | Leu | Phe | Ile | Glu | Trp | tPro | tPro | tPro | tPro | Ser |
| 36 | His | Gly | Glu | Phe | Thr | Ser | Asp | Leu | Met | Phe | Ile | Glu | Phe | hPro | hPro | hPro | hPro | Ser |
| 37 | His | Gly | Glu | Phe | Thr | Ser | Asp | Leu | Leu | Phe | Ile | Glu | Phe | MeAla | MeAla | MeAla | MeAla | Ser |
| 38 | His | Gly | Glu | Phe | Thr | Ser | Asp | Leu | Met | Phe | Ile | Glu | Trp | Pro | MeAla | MeAla | MeAla | Ser |
| 39 | His | Gly | Glu | Phe | Thr | Ser | Asp | Leu | Leu | Phe | Ile | Glu | Phe | MeAla | MeAla | MeAla | MeAla | Ser |

Fig. 15B

EXENDIN AGONIST FORMULATIONS AND METHODS OF ADMINISTRATION THEREOF

RELATED APPLICATIONS

This application claims priority from International Application No. PCT/US00/00902, filed Jan. 14, 2000, which claims priority from U.S. Provisional Application 60/116, 380, entitled "Novel Exendin Agonist Formulations and Methods of Administration Thereof," filed Jan. 14, 1999, and U.S. Provisional Application 60/175,365, entitled "Use of Exendins and Agonists Thereof for Modulation of Triglyceride Levels and Treatment of Dyslipidemia," filed Jan. 10, 2000, the contents of which are hereby incorporated by reference in their entireties.

FIELD OF THE INVENTION

The present invention relates to novel exendin and peptide exendin agonist formulations, dosages, and dosage formulations that are bioactive and are deliverable via injectable and non-injectable routes, for example, via the respiratory tract, the mouth, and the gut. These formulations and dosages and methods of administration are useful in the treatment of diabetes, including Type I and II diabetes, in the treatment of disorders which would be benefited by agents which lower plasma glucose levels, and in the treatment of disorders which would be benefited by the administration of agents useful in delaying and/or slowing gastric emptying or reducing food intake.

BACKGROUND

The following description includes information that may be useful in understanding the present invention. It is not an admission that any of the information provided herein is prior art to the presently claimed inventions, or relevant, nor that any of the publications specifically or implicitly referenced are prior art.

The exendins are peptides that are found in the salivary secretions of the Gila monster and the Mexican Beaded Lizard, reptiles that are indigenous to Arizona and Northern Mexico. Exendin-3 [SEQ ID. NO. 1: His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-$NH_2$] is present in the salivary secretions of *Heloderma a horridum* (Mexican Beaded Lizard), and exendin-4 [SEQ. ID. NO. 2: His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-$NH_2$] is present in the salivary secretions of *Heloderma suspectum* (Gila monster)(Eng, J., et al., *J. Biol. Chem.*, 265:20259–62, 1990; Eng, J., et al., *J. Biol. Chem.*, 267:7402–05, 1992). The amino acid sequence of exendin-3 is shown in FIG. 1. The amino acid sequence of exendin-4 is shown in FIG. 2. Exendin-4 was first thought to be a (potentially toxic) component of the venom. It now appears that exendin-4 is devoid of toxicity, and that it instead is made in salivary glands in the Gila monster.

The exendins have some sequence similarity to several members of the glucagon-like peptide family, with the highest homology, 53%, being to GLP-1 [7–36]$NH_2$ [SEQ ID NO. 189] (Goke, et al., J. Biol. Chem., 268:19650–55, 1993). GLP-1 [7–36] $NH_2$ is also known as proglucagon [78–107], or simply "GLP-1" as used most often herein. GLP-1 has an insulinotropic effect, stimulating insulin secretion from pancreatic beta cells. GLP-1 has also been reported to inhibit glucagon secretion from pancreatic alpha-cells (Ørsov, et al., Diabetes, 42:658–61, 1993; D'Alessio, et al., J. Clin. Invest., 97:133–38, 1996). The amino acid sequence of GLP-I is shown in FIG. 3. GLP-1 has been reported to inhibit gastric emptying (Willms B, et al., J Clin Endocrinol Metab 81 (1): 327–32, 1996; Wettergren A, et al., Dig Dis Sci 38 (4): 665–73, 1993), and gastric acid secretion (Schjoldager BT, et al., Dig Dis Sci 34 (5): 703–8, 1989; O'Halloran DJ, et al., J Endocrinol 126 (1): 169–73, 1990; Wettergren A, et al, Dig Dis Sci 38 (4): 665–73, 1993)). GLP-1[7–37], which has an additional glycine residue at its carboxy terminus, also stimulates insulin secretion in humans (Ørsov, et al., Diabetes, 42: 658–61, 1993). A transmembrane G-protein adenylate-cyclase-coupled receptor said to be responsible at least in part for the insulinotropic effect of GLP-1 has reportedly been cloned from a beta-cell line (Thorens, Proc. Natl. Acad. Sci. USA 89: 8641–45, 1992).

GLP-1 has been the focus of significant investigation in recent years due to reported actions such as the amplification of stimulated insulin production (Byrne M M, Goke B. Lessons from human studies with glucagon-like peptide-1: Potential of the gut hormone for clinical use. In: Fehmann H C, Goke B. Insulinotropic Gut Hormone Glucagon-Like Peptide 1. Basel, Switzerland: Karger, 1997:219–33), the inhibition of gastric emptying (Wettergren A, et al., Truncated GLP-1 (proglucagon 78–107-amide) inhibits gastric and pancreatic functions in man, *Dig. Dis. Sci.* 1993 April; 38 (4): 665–73), the inhibition of glucagon secretion (Creutzfeldt WOC, et al., Glucagonostatic actions and reduction of fasting hyperglycemia by exogenous glucagon-like peptide I(7-36) amide in type I diabetic patients, *Diabetes Care* 1996;19(6):580–6), and a purported role in appetite control (Turton M D, et al., A role for glucagon-like peptide-1 in the central regulation of feeding, *Nature* 1996 January; 379(6560):69–72). GLP-1 has also been reported to restore islet glucose sensitivity in aging rats, restoring their glucose tolerance to that of younger rats (Egan J M, et al., Glucagon-like peptide-1 restores acute-phase insulin release to aged rats, Diabetologia 1997 June 40(Suppl 1):A130). The short duration of biological action of GLP-1 in vivo is one feature of the peptide that has hampered its development as a therapeutic agent.

Pharmacological studies have demonstrated both similarities and differences between exendin-4 and GLP-1. Exendin-4 reportedly can act at GLP-1 receptors on insulin-secreting βTC1 cells, at dispersed acinar cells from guinea pig pancreas, and at parietal cells from stomach. The peptide is also reported to stimulate somatostatin release and inhibit gastrin release in isolated stomachs (Goke, et al., *J. Biol. Chem.* 268:19650–55, 1993; Schepp, et al., *Eur. J. Pharmacol.*, 69:183–91, 1994; Eissele, et al., *Life Sci.*, 55:629–34, 1994). Exendin-3 and exendin-4 were reportedly found to stimulate CAMP production in, and amylase release from, pancreatic acinar cells (Malhotra, R., et al., *Regulatory Peptides*, 41:149–56, 1992; Raufman, et al., *J. Biol. Chem.* 267;21432–37, 1992; Singh, et al., *Regul. Pent.* 53:47–59, 1994). Exendin-4 also has a significantly longer duration of action than GLP-1. For example, in one experiment, glucose lowering by exendin-4 in diabetic mice was reported to persist for several hours, and, depending on dose, for up to 24 hours (Eng J. Prolonged effect of exendin-4 on hyperglycemia of db/db mice, *Diabetes* 1996 May; 45(Suppl 2):152A (abstract 554)). Based on their insulinotropic activities, the use of exendin-3 and exendin-4 for the treatment of diabetes mellitus and the prevention of hyperglycemia has been proposed (Eng, U.S. Pat. No. 5,424, 286).

C-terminally truncated exendin peptides such as exendin-4[9-39], a carboxyamidated molecule, and fragments 3-39 through 9-39 have been reported to be potent and selective antagonists of GLP-1 (Goke, et al., *J. Biol. Chem.*, 268:19650–55, 1993; Raufman, J. P., et al., *J. Biol. Chem.* 266:2897–902, 1991; Schepp, W., et al., *Eur. J. Pharm.* 269:183–91, 1994; Montrose-Rafizadeh, et al., Diabetes, 45(Suppl. 2):152A, 1996). Exendin-4[9-39] is said to block endogenous GLP-1 in vivo, resulting in reduced insulin secretion. Wang, et al., *J. Clin. Invest.*, 95:417–21, 1995; D'Alessio, et al., *J. Clin. Invest.*, 97:133–38, 1996). A receptor apparently responsible for the insulinotropic effect of GLP-1 in rats has reportedly been cloned from rat pancreatic islet cell (Thorens, B., *Proc. Natl. Acad. Sci. USA* 89:8641–8645, 1992). Exendins and exendin-4[9-39] are said to bind to the cloned rat GLP-1 receptor (rat pancreatic β-cell GLP-1 receptor (Fehmann HC, et al., *Peptides* 15 (3): 453–6, 1994) and human GLP-1 receptor (Thorens B, et al., *Diabetes* 42 (11): 1678–82, 1993)). In cells transfected with the cloned GLP-1 receptor, exendin-4 is reportedly an agonist, i.e., it increases cAMP, while exendin [9-39] is identified as an antagonist, i.e., it blocks the stimulatory actions of exendin-4 and GLP-1. Id.

Exendin-4 [9-39] is also reported to act as an antagonist of the full length exendins, inhibiting stimulation of pancreatic acinar cells by exendin-3 and exendin-4 (Raufman, et al., J. Biol. Chem. 266:2897–902, 1991; Raufman, et al., J. Biol. Chem., 266:21432–37, 1992). It is also reported that exendin [9-39] inhibits the stimulation of plasma insulin levels by exendin-4, and inhibits the somatostatin release-stimulating and gastrin release-inhibiting activities of exendin-4 and GLP-1 (Kolligs, F., et al., Diabetes, 44:16–19, 1995; Eissele, et al., Life Sciences, 55:629–34, 1994). Exendin [9-39] has been used to investigate the physiological relevance of central GLP-1 in control of food intake (Turton, M. D. et al. Nature 379:69–72, 1996). GLP-1 administered by intracerebroventricular (ICV) injection inhibits food intake in rats. This satiety-inducing effect of GLP-1 delivered ICV is reported to be inhibited by ICV injection of exendin [9-39] (Turton, supra). However, it has been reported that GLP-1 does not inhibit food intake in mice when administered by peripheral injection (Turton, M. D., Nature 379:69–72, 1996; Bhavsar, S. P., Soc. Neurosci. Abstr. 21:460 (188.8), 1995).

The results of an investigation of whether exendins are the species homolog of mammalian GLP-1 was reported by Chen and Drucker who cloned the exendin gene from the Gila monster (J. Biol. Chem. 272(7):4108–15 (1997)). The observation that the Gila monster also has separate genes for proglucagons (from which GLP-1 is processed), that are more similar to mammalian proglucagon than exendin, indicates that exendins are not species homologs of GLP-1.

Agents that serve to delay gastric emptying have found a place in medicine as diagnostic aids in gastrointestinal radiological examinations. For example, glucagon is a polypeptide hormone that is produced by the alpha cells of the pancreatic islets of Langerhans. It is a hyperglycemic agent that mobilizes glucose by activating hepatic glycogenolysis. It can to a lesser extent stimulate the secretion of pancreatic insulin. Glucagon is used in the treatment of insulin-induced hypoglycemia, for example, when administration of glucose intravenously is not possible. However, as glucagon reduces the motility of the gastro-intestinal tract it is also used as a diagnostic aid in gastrointestinal radiological examinations. Glucagon has also been used in several studies to treat various painful gastrointestinal disorders associated with spasm. Daniel, et al. (Br. Med. J., 3:720, 1974) reported quicker symptomatic relief of acute diverticulitis in patients treated with glucagon compared with those who had been treated with analgesics or antispasmodics. A review by Glauser, et al. (*J. Am. Coll. Emergency Physns*, 8:228, 1979) described relief of acute esophageal food obstruction following glucagon therapy. In another study, glucagon significantly relieved pain and tenderness in 21 patients with biliary tract disease compared with 22 patients treated with placebo (M. J. Stower, et al., *Br. J. Surg.*, 69:591–2, 1982).

Methods for regulating gastrointestinal motility using amylin agonists are described in commonly owned International Application No. PCT/US94/10225, published Mar. 16, 1995.

Methods for regulating gastrointestinal motility using exendin agonists are described in commonly owned U.S. patent application Ser. No. 08/908,867, filed Aug. 8, 1997 entitled "Methods for Regulating Gastrointestinal Motility," which application is a continuation-in-part of U.S. patent application Ser. No. 08/694,954 filed Aug. 8, 1996.

Methods for reducing food intake using exendin agonists are described in commonly owned U.S. patent application Ser. No. 09/003,869, filed Jan. 7, 1998, entitled "Use of Exendin and Agonists Thereof for the Reduction of Food Intake," which claims the benefit of U.S. Provisional Application No. 60/034,905 filed Jan. 7, 1997, No. 60/055,404 filed Aug. 7, 1997, No. 60/065,442 filed Nov. 14, 1997 and No. 60/066,029 filed Nov. 14, 1997.

Exendins have also been reported to have inotropic and diuretic effects, as set forth in commonly owned International Application No. PCT/US99/02554, filed Feb. 5, 1999, claiming the benefit of Provisional Application No. 60/075, 122, filed Feb. 13, 1998.

Novel exendin agonist compounds are described in commonly owned PCT Application Serial No. PCT/US98/16387 filed Aug. 6, 1998, entitled "Novel Exendin Agonist Compounds," which claims the benefit of U.S. patent application Ser. No. 60/055,404, filed Aug. 8, 1997.

Other novel exendin agonists are described in commonly owned PCT Application Serial No. PCT/US98/24210, filed Nov. 13, 1998, entitled "Novel Exendin Agonist Compounds," which claims the benefit of U.S. Provisional Application No. 60/065,442 filed Nov. 14, 1997.

Still other novel exendin agonists are described in commonly owned PCT Application Serial No. PCT/US98/24273, filed Nov. 13, 1998, entitled "Novel Exendin Agonist Compounds," which claims the benefit of U.S. Provisional Application No. 60/066,029 filed Nov. 14, 1997.

Since the appearance of the first therapeutically active peptides and proteins produced by genetic engineering, there has been an ever-increasing demand to be able to deliver these drugs by routes other than parenteral. This has been thwarted, however, by the very properties of peptides and proteins that set them apart from the small drug molecules widely in use today. These properties include molecular size, susceptibility to proteolytic breakdown, rapid plasma clearance, peculiar dose-response curves, immunogenicity, biocompatibility, and the tendency of peptides and proteins to undergo aggregation, adsorption, and denaturation.

It is generally understood that the administration of peptide drugs by routes other than subcutaneous or intravenous injection, or intravenous infusion, is often not practical because of, for example, in the case of oral administration, both enzymatic degradation and non-absorption in the gastrointestinal tract. Thus, there continues to exist a need for the development of alternative methods to the inconvenient, sometimes painful, injection for administration of peptide drugs, such as exendins and the peptide exendin agonist analogs referenced above. In addition to formulations and dosages useful in the administration of exendins and exendin agonists by injection, formulations, dosage formulations, and methods that solve these problems and that are useful in the non-injection delivery of therapeutically effective amounts of exendin and exendin agonists are described and claimed herein.

The contents of the above-identified articles, patents, and patent applications, and all other documents mentioned or cited herein, are hereby incorporated by reference in their entirety. Applicants reserve the right to physically incorporate into this application any and all materials and information from any such articles, patents, patent applications, or other documents mentioned or cited herein.

SUMMARY OF THE INVENTION

According to one aspect, the present invention provides novel exendin and exendin agonist compound formulations and dosages thereof exhibiting advantageous properties that include effects in slowing gastric emptying and lowering plasma glucose levels. Thus, this aspect of the invention includes formulations of exendins and exendin agonists that comprise an exendin or exendin agonist mixed together with a buffer (preferably an acetate buffer), an iso-osmolality modifier (preferably mannitol), and optionally containing a preservative (preferably m-cresol), said formulation having a pH of between about 3.0 and about 7.0 (preferably between about 4.0 and about 5.0). By an "exendin agonist" is meant a compound that mimics one or more effects of exendin, for example, by binding to a receptor where exendin causes one or more of these effects, or by activating a signaling cascade by which exendin causes one or more of these effects. Exendin agonists include exendin agonist peptides, such as analogs and derivatives of exendin-3 and exendin-4 that have one or more desired activities of exendin. Various exendin agonist analogs are identified or referenced herein.

Additional exendin and exendin agonist formulations within the scope of the invention include a parenteral liquid dosage form, a lyophilized unit-dosage form, a lyophilized multi-use dosage form, and modifications of these dosage forms that are useful in the oral, nasal, buccal, sublingual, intra-tracheal, and pulmonary delivery of exendins and exendin agonists.

Thus, the invention includes parenteral liquid dosage forms that comprise approximately 0.005 to about 0.4%, more specifically from about 0.005 to about 0.02%, or from about 0.005 to about 0.05% (w/v), respectively of the active ingredient in an aqueous system along with approximately 0.02 to 0.5% (w/v) of an acetate, phosphate, citrate or glutamate or similar buffer either alone or in combination to obtain a pH of the final composition of approximately 3.0 to 7.0, more specifically from about pH 4.0 to about 6.0, or from about 4.0 to 5.0, as well as either approximately 1.0 to 10% (w/v) of a carbohydrate or polyhydric alcohol iso-osmolality modifier (preferably mannitol) or up to about 0.9% saline or a combination of both leading to an isotonic or an iso-osmolar solution in an aqueous continuous phase. Approximately 0.005 to 1.0% (w/v) of an anti-microbial preservative selected from the group consisting of m-cresol, benzyl alcohol, methyl, ethyl, propyl and butyl parabens and phenol is also present if the formulation is packaged in a multi-use container. A sufficient amount of water for injection is added to obtain the desired concentration of solution. Sodium chloride, as well as other excipients, may also be present, if desired. Such excipients, however, must maintain the overall stability of the active ingredient. Useful polyhydric alcohols include such compounds as sorbitol, mannitol, glycerol, and polyethylene glycols (PEGs). The polyhydric alcohols and the carbohydrates will also be effective in stabilizing protein against denaturation caused by elevated temperature and by freeze-thaw or freeze-drying processes. Suitable carbohydrates include galactose, arabinose, lactose or any other carbohydrate which does not have an adverse affect on a diabetic patient, if intended for that use, i.e., the carbohydrate is not metabolized to form large concentrations of glucose in the blood. Preferably, the peptides of the present invention are admixed with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Mannitol is the preferred polyhydric alcohol.

The lyophilized unit-dose formulations of the present invention are also stable, but need not be isotonic and/or iso-osmolar. They include active ingredient(s), a bulking agent to facilitate cake formation (which may also act as a tonicifer and/or iso-osmolality modifier upon reconstitution to either facilitate stability of the active ingredient and/or lessen the pain on injection), and may also include a surfactant that benefits the properties of the cake and/or facilitates reconstitution. The lyophilized unit-dose formulations of the present invention include approximately 0.005 to about 0.4%, more specifically from about 0.005 to about 0.02%, or 0.005 to 0.05% (w/v) of the active ingredient. It may not be necessary to include a buffer in the formulation and/or to reconstitute the lyophile with a buffer if the intention is to consume the contents of the container within the stability period established for the reconstituted active ingredient. If a buffer is used, it may be included in the lyophile or in the reconstitution solvent. Therefore, the formulation and/or the reconstitution solvent may contain individually or collectively approximately 0.02 to 0.5% (w/v) of an acetate, phosphate, citrate or glutamate buffer either alone or in combination to obtain a pH of the final composition of approximately 3.0 to 7.0, more specifically from about pH 4.0 to about 6.0, or from about 4.0 to 5.0. The bulking agent may consist of either approximately 1.0 to 10% (w/v) of a carbohydrate or polyhydric alcohol iso-osmolality modifier (as described above) or up to 0.9% saline or a combination of both leading to a isotonic or iso-osmolar solution in the reconstituted aqueous phase. A surfactant, preferably about 0.1 to about 1.0% (w/v) of polysorbate 80 or other non-ionic detergent, may be included. As noted above, sodium chloride, as well as other excipients, may also be present in the lyophilized unit-dosage formulation, if desired. The liquid formulation of the invention prior to lyophilization will be substantially isotonic and/or iso-osmolar either before lyophilization or to enable formation of isotonic and/or iso-osmolar solutions after reconstitution.

The invention also includes lyophilized and liquid multi-dose formulations. As with the parenteral liquid and lyophilized unit-dosage formulations described above, the lyophilized multi-unit-dosage form should contain a bulking agent to facilitate cake formation. A preservative is included to facilitate multiple use by the patient. These dosage forms include approximately 0.005 to about 0.4%, more specifically from about 0.005 to about 0.02%, or from about 0.005 to 0.05% (w/v), respectively of the active ingredient. If a buffer is used, it may be included in the lyophile or in the reconstitution solvent, and the formulation and/or the reconstitution solvent may contain individually or collectively approximately 0.02 to 0.5% (w/v) of an acetate, phosphate, citrate or glutamate buffer either alone or in combination to obtain a pH of the final composition of approximately 3.0 to 7.0, more specifically from about pH 4.0 to about 6.0, or from about 4.0 to 5.0. The bulking agent may consist of either approximately 1.0 to 10% (w/v) of a carbohydrate or a polyhydric alcohol iso-osmolality modifier (preferably mannitol) or up to 0.9% saline, or a combination of both, leading to an isotonic or iso-osmolar solution in the reconstituted aqueous phase. A surfactant, preferably about 0.1 to about 1.0% (w/v) of polysorbate 80 or other non-ionic detergent, may be included. Approximately 0.005 to 1.0% (w/v) of an anti-microbial preservative selected from the group consisting of m-cresol, benzyl alcohol, methyl, ethyl, propyl and butyl parabens and phenol (preferably m-cresol) is also present if the formulation is packaged in a multi-use container. Sodium chloride, as well as other excipients, may also be present, if desired. The liquid formulation of the invention should be substantially isotonic and/or iso-osmolar either before lyophilization or to enable formation of isotonic and/or iso-osmolar solutions after reconstitution.

The invention further includes solid dosage forms useful for oral, buccal, sublingual, intra-tracheal, nasal, and pulmonary delivery. The formulations that best support pulmonary and/or intra-tracheal dosage forms may be either preserved or unpreserved liquid formulations and/or dry powder formulations. The preserved or unpreserved liquid formulations will be essentially identical to the formulations described above under preserved or unpreserved liquid parenteral formulations. The pH of the solution should be about 3.0 to 7.0, more specifically from about 4.0 to 6.0, or from about 4.0 to 5.0, with a pH greater than or equal to about 5.0 being most preferred to reduce the potential for bronchoconstriction. The dry powder formulations may contain a bulking agent and/or salts to facilitate particle size formation and appropriate particle size distribution. A surfactant and/or salts may also benefit the properties of the particle morphology and/or facilitate tissue uptake of the active ingredient. Dry powder dosage forms can range from 1% to 100% (w/w), respectively of the active ingredient. It may not be necessary to include a bulking agent and/or salts to facilitate particle size formation and/or distribution. The bulking agent and/or salts may consist of either approximately 0 to 99% (w/w) of a carbohydrate or polyhydric alcohol or approximately 0 to 99% salt or a combination of both leading to the preferred particle size and distribution. A surfactant, preferably about 0.1 to about 1.0% (W/w) of polysorbate 80 or other non-ionic detergent, may be included. Sodium chloride, as well as other excipients, may also be present, if desired. Such excipients, however, will maintain the overall stability of the active ingredient and facilitate the proper level of hydration.

Also within the scope of the invention is the formulation comprising up to 50 mg/ml of an exendin or an exendin agonist in 30 mM acetate buffer (pH about 4.5) and mannitol, with or without a preservative.

Further within the scope of the invention are preferred dosages for exendins and exendin agonists when given by injection, and when given by other routes. Thus, formulations for exendin and exendin agonists having comparable potency are provided for the administration by injection of from about 0.1 to about 0.5 $\mu$g per kilogram, given one to three times per day. Typically, for the patient with diabetes who weighs in the range from about 70 kilograms (average for the type 1 diabetic) to about 90 kilograms (average for the type 2 diabetic), for example, this will result in the total administration of about 10 to about 120 $\mu$g per day in single or divided doses. If administered in divided doses, the doses are preferably administered two or three times per day, and more preferably, two times per day.

In a preferred injection procedure, the exendin or exendin agonist is administered parenterally, more preferably by injection, for example, by peripheral injection. Preferably, about 1 $\mu$g–30 $\mu$g to about 1 mg of the exendin or exendin agonist is administered per day. More preferably, about 1–30 $\mu$g to about 500 $\mu$g, or about 1–30 $\mu$g to about 50 $\mu$g of the exendin or exendin agonist is administered per day. Most preferably, depending upon the weight of the subject and the potency of the compound administered, about 3 $\mu$g to about 50 $\mu$g of the exendin or exendin agonist is administered per day. Preferred doses based upon patient weight for compounds having approximately the potency of exendin-4 range from about 0.005 $\mu$g/kg per dose to about 0.2 $\mu$g/kg per dose. More preferably, doses based upon patient weight for compounds having approximately the potency of exendin-4 range from about 0.02 $\mu$g/kg per dose to about 0.1 $\mu$g/kg per dose. Most preferably, doses based upon patient weight for compounds having approximately the potency of exendin-4 range from about 0.05 $\mu$g/kg per dose to about 0.1 $\mu$g/kg per dose. These doses are administered from 1 to 4 times per day, preferably from 1 to 2 times per day. Doses of exendins or exendin agonists will normally be lower if given by continuous infusion. Doses of exendins or exendin agonists will normally be higher if given by non-injection methods, such as oral, buccal, sublingual, nasal, pulmonary or skin patch delivery.

Oral dosages according to the present invention will include from about 50 to about 100 times the active ingredient, e.g., from about 500 to about 12,000 $\mu$g per day in single or divided doses, preferably from about 500 to about 5,000 $\mu$g per day. Pulmonary dosages according to the present invention will include from about 10 to about 100 times the active ingredient, e.g., from about 100 to about 12,000 $\mu$g per day in single or divided doses, preferably about 500 to 1000 $\mu$g per day. Nasal, buccal and sublingual dosages according to the present invention will also include from about 10 to about 100 times the active ingredient, e.g., from about 100 to about 12,000 $\mu$g per day in single or divided doses.

Preferred dosages for nasal administration are from about 10–1000 to about 1200–12,000 $\mu$g per day, for buccal administration from about 10–1000 to about 1200–12,000 $\mu$g per day, and for sublingual administration from about 10–1000 to about 1200–8,000 $\mu$g per day. Sublingual dosages are preferably smaller than buccal dosages. Administration dosages for exendin agonists having less than or greater than the potency of exendin-4 are increased or decreased as appropriate from those described above and elsewhere herein.

Also included within the scope of the present invention are methods of administration of said novel exendin agonist compound formulations and dosages by delivery means alternative to subcutaneous injection or intravenous infusion, including, for example, by nasal delivery, pulmonary delivery, oral delivery, intra-tracheal delivery, sublingual delivery, and buccal delivery.

According to another aspect, the present invention provides novel exendin agonist compound formulations and dosages, and methods for the administration thereof, that are useful in treating diabetes (including type 1 and type 2 diabetes), obesity, and other conditions that will benefit from the administration of a therapy that can slow gastric emptying, lowering plasma glucose levels, and reduce food intake.

The invention also includes methods for treatment of subjects in order to increase insulin sensitivity by administering an exendin or an exendin agonist. The exendin and exendin agonist formulations and dosages described herein may be used to increase the sensitivity of a subject to endogenous or exogenous insulin.

In one preferred aspect, the exendin or exendin agonist used in the methods of the present invention is exendin-3 [SEQ ID NO. 1]. In another preferred aspect, said exendin is exendin-4 [SEQ ID NO. 2). Other preferred exendin agonists include exendin-4 (1-30) [SEQ ID NO. 6: His Gly Glu Gly Thr Phe Thr Ser Asp Leu Ser Lys Gln Met Glu Glu Glu Ala Val Arg Leu Phe Ile Glu Trp Leu Lys Asn Gly Gly], exendin-4 (1-30) amide [SEQ ID NO. 7: His Gly Glu Gly Thr Phe Thr Ser Asp Leu Ser Lys Gln Met Glu Glu Glu Ala Val Arg Leu Phe Ile Glu Trp Leu Lys Asn Gly Gly-$NH_2$], exendin-4 (1-28) amide [SEQ ID NO., 40: His Gly Glu Gly Thr Phe Thr Ser Asp Leu Ser Lys Gln Met Glu Glu Glu Ala Val Arg Leu Phe Ile Glu Trp Leu Lys Asn-$NH_2$], $^{14}$Leu, $^{25}$Phe exendin-4 [SEQ ID NO. 9: His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-$NH_2$], $^{4}$Leu, $^{25}$Phe exendin-4 (1-28) amide [SEQ ID NO. 41: His Gly Glu Gly Thr Phe Thr Ser Asp Leu Ser Lys Gln Leu Glu Glu Glu Ala Val Arg Leu Phe Ile Glu Phe Leu Lys Asn-$NH_2$], and $^{14}$Leu, $^{22}$Ala, $^{25}$Phe exendin-4 (1-28) amide [SEQ ID NO. 8: His Gly Glu Gly Thr Phe Thr Ser Asp Leu Ser Lys Gln Leu Glu Glu Glu Ala Val Arg Leu Ala Ile Glu Phe Leu Lys Asn-$NH_2$].

Other features and advantages of the invention will be apparent from the following description of the preferred embodiments thereof, and from the claims.

In accordance with the present invention and as used herein, the following terms are defined to have the following meanings, unless explicitly stated otherwise. "Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

BRIEF DESCRIPTION OF THE DRAWINGS

FIG. 1 depicts the amino acid sequence for exendin-3 [SEQ ID NO. 1].

FIG. 2 depicts the amino acid sequence for exendin-4 [SEQ ID NO. 2].

FIG. 3 depicts the amino acid sequence for GLP-1[7-36] $NH_2$ (GLP-1) [SEQ ID NO. 189].

FIG. 5a depicts the plasma exendin-4 concentration after intra-tracheal instillation in db/db mice.

FIG. 5b depicts the effect of intra-tracheal administration of exendin-4 on plasma glucose in db/db mice.

FIG. 8 depicts plasma exendin-4 concentrations in rats exposed to aerosolized exendin-4.

FIG. 9a depicts the effect of ten minutes of exposure to aerosolized exendin-4 on plasma glucose in db/db mice.

FIG. 9b depicts the plasma exendin-4 concentration after ten minutes of exposure of db/db mice to aerosolized exendin-4.

FIG. 11 depicts the effect of intra-gastric administration of exendin-4 on plasma glucose in db/db mice.

FIG. 13 depicts the effect of exendin-4 (administered i.p. twice daily) on food intake (a), change in body weight (b) (initial body weight 441±39 g), or change in hemoglobin $A_{1c}$ (c) (7.68±0.20% at 0 weeks). Dose-responses (right panels) are for the means over the last 2 of 6 weeks treatment.

FIG. 15 depicts the amino acid sequences for certain exendin agonist compounds useful in the present invention [SEQ ID NOs. 9–39].

DETAILED DESCRIPTION OF THE INVENTION

Exendins and Exendin Agonists

Figure 4:
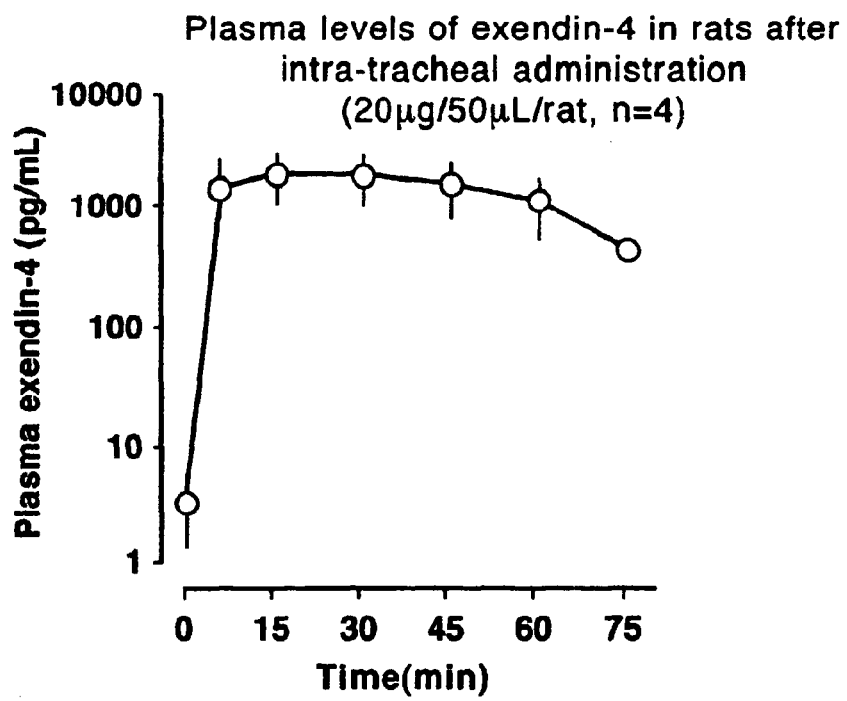
FIG. 4 depicts the plasma levels of exendin-4 in rats after intra-tracheal administration.

Exendin-3 and Exendin-4 are naturally occurring peptides isolated from the salivary secretions of the Gila monster and the Mexican Beaded Lizard. Animal testing of exendin-4 has shown that its ability to lower blood glucose persists for several hours. Exendin-4, a 39-amino acid polypeptide, is synthesized using solid phase synthesis as described herein, and this synthetic material has been shown to be identical to that of native exendin-4.

Various aspects of the nonclinical pharmacology of exendin-4 have been studied. In the brain, exendin-4 binds principally to the area postrema and nucleus tractus solitarius region in the hindbrain and to the subfornical organ in the forebrain. Exendin-4 binding has been observed in the rat and mouse brain and kidney. The structures to which exendin-4 binds in the kidney are unknown.

A number of other experiments have compared the biologic actions of exendin-4 and GLP-1 and demonstrated a more favorable spectrum of properties for exendin-4. A single subcutaneous dose of exendin-4 lowered plasma glucose in db/db (diabetic) and ob/ob (diabetic obese) mice by up to 40%. In Diabetic Fatty Zucker (ZDF) rats, 5 weeks of treatment with exendin-4 lowered $HbA_{1c}$ (a measure of glycosylated hemoglobin used to evaluate plasma glucose levels) by up to 41%. Insulin sensitivity was also improved by 76% following 5 weeks of treatment in obese ZDF rats. In glucose intolerant primates, dose-dependent decreases in plasma glucose were also observed. See also Example 6, which describes the results of an experiment indicating that exendin is more potent and/or effective than GLP-1 in amplifying glucose-stimulated insulin release. Example 8, furthermore, describes work showing that the ability of exendin-4 to lower glucose in vivo was 3430 times more potent than that of GLP-1.

An insulinotropic action of exendin-4 has also been observed in rodents, improving insulin response to glucose by over 100% in non-fasted. Harlan Sprague Dawley (HSD) rats, and by up to –10-fold in non-fasted db/db mice. Higher pretreatment plasma glucose concentrations were associated with greater glucose-lowering effects. Thus the observed glucose lowering effect of exendin-4 appears to be glucose-dependent, and minimal if animals are already euglycemic. Exendin-4 treatment is also associated with improvement in glycemic indices and in insulin sensitivity, as described in Examples 9 and 13.

Exendin-4 dose dependently slowed gastric emptying in HSD rats and was 90-fold more potent than GLP-1 for this action. Exendin-4 has also been shown to reduce food intake in NIH/Sw (Swiss) mice following peripheral administration, and was at least 1000 times more potent than GLP-1 for this action. Exendin-4 reduced plasma glucagon concentrations by approximately 40% in anesthetized ZDF rats during hyperinsulinemic, hyperglycemic clamp conditions, but did not affect plasma glucagon concentrations during euglycemic conditions in normal rats. See Example 4. Exendin-4 has been shown to dose-dependently reduce body weight in obese ZDF rats, while in lean ZDF rats, the observed decrease in body weight appears to be transient.

Through effects on augmenting and restoring insulin secretion, as well as inhibiting glucagon secretion, exendin-4 will be useful in people with type 2 diabetes who retain the ability to secrete insulin. Its effects on food intake, gastric emptying, other mechanisms that modulate nutrient absorption, and glucagon secretion also support the utility of exendin-4 in the treatment of, for example, obesity, type 1 diabetes, and people with type 2 diabetes who have reduced insulin secretion.

The toxicology of exendin-4 has been investigated in single-dose studies in mice, rats, and monkeys, repeated-dose (up to 28 consecutive daily doses) studies in rats and monkeys and in vitro tests for mutagenicity and chromosomal alterations. To date, no deaths have occurred, and there have been no observed treatment-related changes in hematology, clinical chemistry, or gross or microscopic tissue changes. Exendin-4 was demonstrated to be non-mutagenic, and did not cause chromosomal aberrations at the concentrations tested (up to 5000 µg/mL). In support of the investigation of the nonclinical pharmacokinetics and metabolism of exendin-4, a number of immunoassays have been developed. A radioimmunoassay with limited sensitivity (–100 pM) was used in initial pharmacokinetic studies. A two-site IRMA assay for exendin-4 was subsequently validated with a lower limit of quantitation of 15 pM. See Examples 5 and 7. The bioavailability of exendin-4, given subcutaneously, was found to be approximately 50–80% using the radioimmunoassay. This was similar to that seen following intraperitoneal administration (48–60%). Peak plasma concentrations ($C_{max}$) occurred between 30 and 43 minutes ($T_{max}$). Both $C_{max}$ and AUC values were monotonically related to dose. The apparent terminal half-life for exendin-4 given subcutaneously was approximately 90–110 minutes. This was significantly longer than the 14–41 minutes seen following intravenous dosing. Similar results were obtained using the IRMA assay. Degradation studies with exendin-4 compared to GLP-1 indicate that exendin-4 is relatively resistant to degradation.

Investigation of the structure activity relationship (SAR) to evaluate structures that may relate to the antidiabetic activity of exendin, for its stability to metabolism, and for improvement of its physical characteristics, especially as it pertains to peptide stability and to amenability to alternative delivery systems, has led to the discovery of exendin agonist peptide compounds. Exendin agonists include exendin peptide analogs in which one or more naturally occurring amino acids are eliminated or replaced with another amino acid(s). Preferred exendin agonists are agonist analogs of exendin-4. Particularly preferred exendin agonists those described in International Application No. PCT/US98/16387, filed Aug. 6, 1998, entitled, "Novel Exendin Agonist Compounds," which claims the benefit of United States Provisional Application No. 60/055,404, filed Aug. 8, 1997, including compounds of the formula (I) [SEQ ID NO. 3]:

$Xaa_1$ $Xaa_2$ $Xaa_3$ Gly Thr $Xaa_4$ $Xaa_5$ $Xaa_6$ $Xaa_7$ $Xaa_8$ Ser Lys Gln $Xaa_9$ Glu Glu Glu Ala Val Arg Leu $Xaa_{10}$ $Xaa_{11}$ $Xaa_{12}$ $Xaa_{13}$ Leu Lys Asn Gly Gly $Xaa_{14}$ Ser Ser Gly Ala $Xaa_{15}$ $Xaa_{16}$ $Xaa_{17}$ $Xaa_{18}$-Z wherein $Xaa_1$ is His, Arg or Tyr; $Xaa_2$ is Ser, Gly, Ala or Thr; $Xaa_3$ is Asp or Glu; $Xaa_4$ is Phe, Tyr or naphthylalanine; $Xaa_5$ is Thr or Ser; $Xaa_6$ is Ser or Thr; $Xaa_7$ is Asp or Glu; $Xaa_8$ is Leu, Ile, Val, pentylglycine or Met; $Xaa_9$ is Leu, Ile, pentylglycine, Val or Met; $Xaa_{10}$ is Phe, Tyr or naphthylalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —NH$_2$; with the proviso that the compound is not exendin-3 or exendin-4.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds include those listed in FIG. 1 having amino acid sequences of SEQ ID NOs. 9 to 39.

Preferred exendin agonist compounds include those wherein $Xaa_1$ is His or Tyr. More preferably, $Xaa_1$ is His.

Preferred are those compounds wherein $Xaa_2$ is Gly.

Preferred are those compounds wherein $Xaa_9$ is Leu, pentylglycine, or Met.

Preferred compounds include those wherein $Xaa_{13}$ is Trp or Phe.

Also preferred are compounds where $Xaa_4$ is Phe or naphthylalanine; $Xaa_{11}$ is Ile or Val and $Xaa_{14}$, $Xaa_{15}$, $Xaa_{16}$ and $Xaa_{17}$ are independently selected from Pro, homoproline, thioproline or N-alkylalanine. Preferably N-alkylalanine has a N-alkyl group of 1 to about 6 carbon atoms.

According to an especially preferred aspect, $Xaa_{15}$, $Xaa_{16}$ and $Xaa_{17}$ are the same amino acid reside.

Preferred are compounds wherein $Xaa_{18}$ is Ser or Tyr, more preferably Ser.

Preferably Z is —NH$_2$.

According to one aspect, preferred are compounds of formula (I) wherein $Xaa_1$ is His or Tyr, more preferably His; $Xaa_2$ is Gly; $Xaa_4$ is Phe or naphthylalanine; $Xaa_9$ is Leu, pentylglycine or Met; $Xaa_{10}$ is Phe or naphthylalanine; $Xaa_{11}$ is Ile or Val; $Xaa_{14}$, $Xaa_{15}$, $Xaa_{16}$ and $Xaa_{17}$ are independently selected from Pro, homoproline, thioproline or N-alkylalanine; and $Xaa_{18}$ is Ser or Tyr, more preferably Ser. More preferably Z is —$NH_2$.

According to an especially preferred aspect, especially preferred compounds include those of formula (I) wherein: $Xaa_1$ is His or Arg; $Xaa_2$ is Gly; $Xaa_3$ is Asp or Glu; $Xaa_4$ is Phe or napthylalanine; $Xaa_5$ is Thr or Ser; $Xaa_6$ is Ser or Thr; $Xaa_7$ is Asp or Glu; $Xaa_8$ is Leu or pentylglycine; $Xaa_9$ is Leu or pentylglycine; $Xaa_{10}$ is Phe or naphthylalanine; $Xaa_{11}$ is Ile, Val or t-butyltylglycine; $Xaa_{12}$ is Glu or Asp; $Xaa_{13}$ is Trp or Phe; $Xaa_{14}$, $Xaa_{15}$, $Xaa_{16}$, and $Xaa_{17}$ are independently Pro, homoproline, thioproline, or N-methylalanine; $Xaa_{18}$ is Ser or Tyr: and Z is —OH or —$NH_2$; with the proviso that the compound does not have the formula of either SEQ. ID. NOS. 1 or 2. More preferably, Z is —$NH_{12}$. Especially preferred compounds include those having the amino acid sequence of SEQ ID NOs. 9, 10, 21, 22, 23, 26, 28, 34, 35 and 39.

According to an especially preferred aspect, provided are compounds where $Xaa_9$ is Leu, Ile, Val or pentylglycine, more preferably Leu or pentylglycine, and $Xaa_{13}$ is Phe, Tyr or naphthylalanine, more preferably Phe or naphthylalanine. These compounds will exhibit advantageous duration of action and be less subject to oxidative degradation, both in vitro and in vivo, as well as during synthesis of the compound.

Exendin agonist compounds also include those described in International Application No. PCT/US98/24210, filed Nov. 13, 1998, entitled, "Novel Exendin Agonist compounds," which claims the benefit of U.S. Provisional Application No. 60/065,442, filed Nov. 14, 1997, including compounds of the formula (II) [SEQ ID NO. 4]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg or Tyr;
$Xaa_2$ is Ser, Gly, Ala or Thr;
$Xaa_3$ is Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Ala, Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is —OH,
—$NH_2$,
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$Ser Ser-$Z_2$,
Gly Gly $Xaa_{31}$ Ser Ser Gly-$Z_2$,
Gly Gly $Xaa_{31}$Ser Ser Gly Ala-$Z_2$,
Gly Gly $Xaa_{31}$Ser Ser Gly Ala $Xaa_{36}$-$Z_2$,
Gly Gly $Xaa_{31}$ Ser Ser Gly Ala $Xaa_{36}$ $Xaa_{37}$-$Z_2$ or
Gly Gly $Xaa_{31}$Ser Ser Gly Ala $Xaa_{36}$ $Xaa_{37}$ $Xaa_{38}$-$Z_2$;
$Xaa_{31}$, $Xaa_{36}$, $Xaa_{37}$ and $Xaa_{38}$ are independently Pro, homoproline, 3Hyp, 4Hyp, thioproline,
N-alkylglycine, N-alkylpentylglycine or
N-alkylalanine; and
$Z_2$ is —OH or —$NH_2$;
provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms.

Preferred exendin agonist compounds include those wherein $Xaa_1$ is His or Tyr. More preferably $Xaa_1$ is His.

Preferred are those compounds wherein $Xaa_2$ is Gly.

Preferred are those compounds wherein $Xaa_{14}$ is Leu, pentylglycine or Met.

Preferred compounds are those wherein $Xaa_{25}$ is Trp or Phe.

Preferred compounds are those where $Xaa_6$ is Phe or naphthylalanine; $Xaa_2 2$ is Phe or naphthylalanine and $Xaa_{23}$ is Ile or Val.

Preferred are compounds wherein $Xaa_{31}$, $Xaa_{36}$, $Xaa_{37}$ and $Xaa_{38}$ are independently selected from Pro, homoproline, thioproline and N-alkylalanine.

Preferably $Z_1$, is —$NH_2$.

Preferable $Z_2$ is —$NH_2$.

According to one aspect, preferred are compounds of formula (II) wherein $Xaa_1$ is His or Tyr, more preferably His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. More preferably $Z_1$ is —$NH_2$.

According to an especially preferred aspect, especially preferred compounds include those of formula (II) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or nephthylalaine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_2$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$ $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$, are Ala. Especially preferred compounds include those having the amino acid sequence of SEQ. ID. NOS. 40–61.

According to an especially preferred aspect, provided are compounds where $Xaa_{14}$ is Leu, Ile, Val or pentylglycine, more preferably Leu or pentylglycine, and $Xaa_{25}$ is Phe, Tyr or naphthylalanine, more preferably Phe or naphthylalanine. These compounds will be less susceptive to oxidative degration, both in vitro and in vivo, as well as during synthesis of the compound.

Exendin agonist compounds also include those described in International Patent Application No. PCT/US98/24273, filed Nov. 13, 1998, entitled, "Novel Exendin Agonist Compounds," which claims the benefit of U.S. Provisional Application No. 60/066,029, filed Nov. 14, 1997, including compounds of the formula (III)[SEQ ID NO. 5]:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg, Tyr, Ala, Norval, Val or Norleu;
$Xaa_2$ is Ser, Gly, Ala or Thr;
$Xaa_3$ is Ala, Asp or Glu;
$Xaa_4$ is Ala, Norval, Val, Norleu or Gly;
$Xaa_5$ is Ala or Thr;
$Xaa_6$ is Phe, Tyr or naphthylalanine;
$Xaa_7$ is Thr or Ser;
$Xaa_8$ is Ala, Ser or Thr;
$Xaa_9$ is Ala, Norval, Val, Norleu, Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_26$ is Ala or Leu;
$Xaa_{27}$ is Ala or Lys;
$Xaa_{28}$ is Ala or Asn;
$Z_1$ is —OH,
  —$NH_2$,
  Gly-$Z_2$,
  Gly Gly-$Z_2$,
  Gly Gly $Xaa_{31}$-$Z_2$,
  Gly Gly $Xaa_{31}$ Ser-$Z_2$,
  Gly Gly $Xaa_{31}$ Ser Ser-$Z_2$,
  Gly Gly $Xaa_{31}$ Ser Ser Gly-$Z_2$,
  Gly Gly $Xaa_{31}$ Ser Ser Gly Ala-$Z_2$,
  Gly Gly $Xaa_{31}$ Ser Ser Gly Ala $Xaa_{36}$-$Z_2$,
  Gly Gly $Xaa_{31}$ Ser Ser Gly Ala $Xaa_{36}$ $Xaa_{37}$-$Z_2$,
  Gly Gly $Xaa_{31}$ Ser Ser Gly Ala $Xaa_{36}$ $Xaa_{37}$ $Xaa_{38}$-$Z_2$ or
  Gly Gly $Xaa_{31}$ Ser Ser Gly Ala $Xaa_{36}$ $Xaa_{37}$ $Xaa_{38}$ $Xaa_{39}$-$Z_2$;
wherein
  $Xaa_{31}$, $Xaa_{36}$, $Xaa_{37}$ and $Xaa_{38}$ are independently Pro, homoproline, 3Hyp, 4Hyp, thioproline,
  N-alkylglycine, N-alkylpentylglycine or N-alkylalanine; and
$Z_2$ is —OH or —$NH_2$;
provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala.

Preparation of Compounds

The compounds that constitute active ingredients of the formulations and dosages of the present invention may be prepared using standard solid-phase peptide synthesis techniques and preferably an automated or semiautomated peptide synthesizer. The preparation of exendin-3 and exendin-4 is described in Examples 1 and 2 below. The preparation of additional exendin agonist peptide analogs is described in Examples 13–198 below.

Typically, using automated or semiautomated peptide synthesis techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu (Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid, and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10 μ, 2.2×25 cm; Vydac, Hesperia, Calif.) may be used to isolate peptides, and purity may be determined using a C4, C8 or C18 analytical column (5 μ, 0.46×25 cm; Vydac). Solvents (A=0.1% TFA/water and B=0.1% TFA/CH$_3$CN) may be delivered to the analytical column at a flow rate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20–24 h). Hydrolysates may be derivatized and analyzed by standard methods (Cohen, et al., *The Pico Tag Method: A Manual of Advanced Techniques for Amino Acid Analysis*, pp. 11–52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried and on a VG-Trio machine.

Peptide active ingredient compounds useful in the formulations and dosages of the invention may also be prepared using recombinant DNA techniques, using methods now known in the art. See, e.g., Sambrook et al., *Molecular Cloning: A Laboratory Manual,* 2d Ed., Cold Spring Harbor (1989).

Utility

The formulations and dosages described herein are useful in view of their pharmacological properties. In particular, the formulations and dosages of the invention are effective as exendins and exendin agonists, and possess activity as agents to lower blood glucose, and to regulate gastric motility and to slow gastric emptying, as evidenced by the ability to reduce post-prandial glucose levels in mammals.

Formulation and Administration

Exendin and exendin agonist formulations and dosages of the invention are useful in view of their exendin-like effects, and may conveniently be provided in the form of formulations suitable for parenteral (including intravenous, intramuscular and subcutaneous) administration. Also described herein are formulations and dosages useful in alternative delivery routes, including oral, nasal, buccal, sublingual and pulmonary.

Compounds useful in the invention can be provided as parenteral compositions for injection or infusion. Generally, they can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 3.0 to about 7.0, more specifically from about 4.0 to 6.0, and preferably from about 4.0 to about 5.0. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The exendin and exendin agonist compounds can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethane sulfonic acid, benzene sulfonic acid, p-toluenesulfonic acid, cyclohexyl sulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another-ion on a suitable ion exchange resin.

Generally, carriers or excipients can also be used to facilitate administration of the dosages of the present invention. Examples of carriers and excipients include calcium carbonate, calcium phosphate, various sugars such as lactose, or types of starch, cellulose derivatives, gelatin, vegetable oils, polyethylene glycols and physiologically compatible solvents.

If desired, solutions of the above dosage compositions may be thickened with a thickening agent such as methylcellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

In general, formulations and dosage compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

Other pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

For use by the physician, the compounds will be provided in dosage unit form containing an amount of an exendin agonist, with or without another therapeutic agent, for example, a glucose-lowering agent, a gastric emptying modulating agent, a lipid lowering agent, or a food intake inhibitor agent. Therapeutically effective amounts of an exendin agonist for use in the control of blood glucose or in the control of gastric emptying and in conditions in which gastric emptying is beneficially slowed or regulated are those that decrease post-prandial blood glucose levels, preferably to no more than about 8 or 9 mM or such that blood glucose levels are reduced as desired. In diabetic or glucose intolerant individuals, plasma glucose levels are higher than in normal individuals. In such individuals, beneficial reduction or "smoothing" of post-prandial blood glucose levels may be obtained. As will be recognized by those in the field, an effective amount of therapeutic agent will vary with many factors including the patient's physical condition, the blood sugar level or level of inhibition of gastric emptying to be obtained, or the desired level of food intake reduction, and other factors.

Such pharmaceutical compositions are useful in causing increased insulin sensitivity in a subject and may be used as well in disorders, such as diabetes, where sensitivity to insulin is beneficially increased.

A form of repository or "depot" slow release preparation may be used so that therapeutically effective amounts of the preparation are delivered into the bloodstream over many hours or days following transdermal injection or other form of delivery.

The effective daily doses of the compounds are described. The exact dose to be administered may be determined by the attending clinician and may be further dependent upon the efficacy of the particular exendin or exendin agonist compound used, as well as upon the age, weight and condition of the individual. The optimal mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

The invention includes formulations of exendins and exendin agonists that comprise an exendin or exendin agonist mixed together with a buffer (preferably an acetate buffer), an iso-osmolality modifier (preferably mannitol), and optionally containing a preservative (preferably m-cresol), said formulation having a pH of between about 3.0 and about 7.0 (preferably between about 4.0 and about 5.0).

The formulation which best supports a parenteral liquid dosage form is one in which the active ingredient(s) is stable with adequate buffering capacity to maintain the pH of the solution over the intended shelf life of the product. The dosage form should be either an isotonic and/or an iso-osmolar solution to either facilitate stability of the active ingredient or lessen the pain on injection or both. Devices that deliver very small injection volumes, however, may not require that the formulation be either isotonic and/or iso-osmolar. If the dosage form is packaged as a unit-dose, then a preservative may be included but is not required. If, however, the dosage form is packaged in a multi-use container, then a preservative is necessary.

These dosage forms include approximately 0.005 to about 0.4%, more specifically from about 0.005 to about 0.02%, or from about 0.005 to about 0.05% (w/v), respectively of the active ingredient in an aqueous system along with approximately 0.02 to 0.5% (w/v) of an acetate, phosphate, citrate or glutamate or similar buffer either alone or in combination to obtain a pH of the final composition of approximately 3.0 to 7.0, more specifically from about pH 4.0 to about 6.0, or from about 4.0 to 5.0, as well as either approximately 1.0 to 10% (w/v) of a carbohydrate or polyhydric alcohol iso-osmolality modifier (preferably mannitol) or up to about 0.9% saline or a combination of both leading to an isotonic or an iso-osmolar solution in an aqueous continuous phase. Approximately 0.005 to 1.0% (w/v) of an anti-microbial preservative selected from the group consisting of m-cresol, benzyl alcohol, methyl ethyl, propyl and butyl parabens and phenol is also present if the formulation is packaged in a multi-use container. A sufficient amount of water for injection is added to obtain the desired concentration of solution. Sodium chloride, as well as other excipients, may also be present, if desired. Such excipients, however, must maintain the overall stability of the active ingredient.

Polyhydric alcohols and carbohydrates share the same feature in their backbones, i.e., —CHOH—CHOH—. The polyhydric alcohols include such compounds as sorbitol, mannitol, glycerol, and polyethylene glycols (PEGs). These compounds are straight-chain molecules. The carbohydrates, such as mannose, ribose, trehalose, maltose, glycerol, inositol, glucose and lactose, on the other hand, are cyclic molecules that may contain a keto or aldehyde group. These two classes of compounds will also be effective in stabilizing protein against denaturation caused by elevated temperature and by freeze-thaw or freeze-drying processes. Suitable carbohydrates include galactose, arabinose, lactose or any other carbohydrate which does not have an adverse affect on a diabetic patient, i.e., the carbohydrate is not metabolized to form large concentrations of glucose in the blood. Such carbohydrates are well known in the art as suitable for diabetics.

Preferably, the peptides of the present invention are admixed with a polyhydric alcohol such as sorbitol, mannitol, inositol, glycerol, xylitol, and polypropylene/ ethylene glycol copolymer, as well as various polyethylene glycols (PEGS) of molecular weight 200, 400, 1450, 3350, 4000, 6000, and 8000). Mannitol is the preferred polyhydric alcohol.

The liquid formulation of the invention should be substantially isotonic and/or iso-osmolar. An isotonic solution may be defined as a solution that has a concentration of electrolytes, or a combination of electrolytes and non-electrolytes that will exert equivalent osmotic pressure as that into which it is being introduced, here for example in the case of parenteral injection of the formulation, a mammalian tissue. Similarly, an iso-osmolar solution may be defined as a solution that has a concentration of non-electrolytes that will exert equivalent osmotic pressure as that into which it is being introduced. As used herein, "substantially isotonic" means within ±20% of isotonicity, preferably within ±10%. As used herein, "substantially iso-osmolar" means within ±20% of iso-osmolality, preferably within ±10%. The formulated product for injection is included within a container, typically, for example, a vial, cartridge, prefilled syringe or disposable pen.

The formulation which best support a unit-dose parenteral lyophilized dosage form is one in which the active ingredient is reasonably stable, with or without adequate buffering capacity to maintain the pH of the solution over the intended shelf life of the reconstituted product. The dosage form should contain a bulking agent to facilitate cake formation. The bulking agent may also act as a tonicifer and/or iso-osmolality modifier upon reconstitution to either facilitate stability of the active ingredient and/or lessen the pain on injection. As noted above, devices that deliver very small injection volumes may not require the formulation to be isotonic and/or iso-osmolar. A surfactant may also benefit the properties of the cake and/or facilitate reconstitution.

These dosage forms include approximately 0.005 to about 0.4%, more specifically from about 0.005 to about 0.02%, or 0.005 to 0.05% (w/v) of the active ingredient. It may not be necessary to include a buffer in the formulation and/or to reconstitute the lyophile with a buffer if the intention is to consume the contents of the container within the stability period established for the reconstituted active ingredient. If a buffer is used, it may be included in the lyophile or in the reconstitution solvent. Therefore, the formulation and/or the reconstitution solvent may contain individually or collectively approximately 0.02 to 0.5% (w/v) of an acetate, phosphate, citrate or glutamate buffer either alone or in combination to obtain a pH of the final composition of approximately 3.0 to 7.0, more specifically from about pH 4.0 to about 6.0, or from about 4.0 to 5.0. The bulking agent may consist of either approximately 1.0 to 10% (w/v) of a carbohydrate or polyhydric alcohol iso-osmolality modifier (as described above) or up to 0.9% saline or a combination of both leading to a isotonic or iso-osmolar solution in the reconstituted aqueous phase. A surfactant, preferably about 0.1 to about 1.0% (w/v) of polysorbate 80 or other non-ionic detergent, may be included. As noted above, sodium chloride, as well as other excipients, may also be present in the lyophilized unit-dosage formulation, if desired. Such excipients, however, must maintain the overall stability of the active ingredient. The formulation will be lyophilized within the validation parameters identified to maintain stability of the active ingredient.

The liquid formulation of the invention before lyophilization should be substantially isotonic and/or iso-osmolar either before lyophilization or to enable formation of isotonic and/or iso-osmolar solutions after reconstitution. The formulation should be used within the period established by shelf-life studies on both the lyophilized form and following reconstitution. The lyophilized product is included within a container, typically, for example, a vial. If other containers are used such as a cartridge, pre-filled syringe, or disposable pen, the reconstitution solvent may also be included.

As with the parenteral liquid and lyophilized unit-dosage formulations described above, the formulation which best supports a multi-dose parenteral lyophilized dosage form is one in which the active ingredient is reasonably stable with adequate buffering capacity to maintain the pH of the solution over the intended "in-use" shelf-life of the product. The dosage form should contain a bulking agent to facilitate cake formation. The bulking agent may also act as a tonicifer and/or iso-osmolality modifier upon reconstitution to either facilitate stability of the active ingredient or lessen the pain on injection or both. Again, devices that deliver very small injection volumes may not require the formulation to be either isotonic and/or iso-osmolar. A preservative is, however, necessary to facilitate multiple use by the patient.

These dosage forms include approximately 0.005 to about 0.4%, more specifically from about 0.005 to about 0.02%, or from about 0.005 to 0.05% (w/v), respectively of the active ingredient. It may not be necessary to include a buffer in the formulation and/or to reconstitute the lyophile with a buffer if the intention is to consume the contents of the container within the stability period established for the reconstituted active ingredient. If a buffer is used, it may be included in the lyophile or in the reconstitution solvent. Therefore, the formulation and/or the reconstitution solvent may contain individually or collectively approximately 0.02 to 0.5% (w/v) of an acetate, phosphate, citrate or glutamate buffer either alone or in combination to obtain a pH of the final composition of approximately 3.0 to 7.0, more specifically from about pH 4.0 to about 6.0, or from about 4.0 to 5.0. The bulking agent may consist of either approximately 1.0 to 10% (w/v) of a carbohydrate or a polyhydric alcohol iso-osmolality modifier (preferably mannitol) or up to 0.9% saline, or a combination of both, leading to an isotonic or iso-osmolar solution in the reconstituted aqueous phase. A surfactant, preferably about 0.1 to about 1.0% (w/v) of polysorbate 80 or other non-ionic detergent, may be included. Approximately 0.005 to 1.0% (w/v) of an antimicrobial preservative selected from the group consisting of m-cresol, benzyl alcohol, methyl, ethyl, propyl and butyl parabens and phenol (preferably m-cresol) is also present if the formulation is packaged in a multi-use container. Sodium chloride, as well as other excipients, may also be present, if desired. Again, however, such excipients must maintain the overall stability of the active ingredient. The formulation should be lyophilized within the validation parameters identified to maintain stability of the active ingredient. The liquid formulation of the invention should be substantially isotonic and/or iso-osmolar either before lyophilization or to enable formation of isotonic and/or iso-osmolar solutions after reconstitution. The formulation should be used within the period established by shelf-life studies on both the lyophilized form and following reconstitution. The lyophilized product is included within a container, typically, for example, a vial. If other containers are used such as a cartridge, pre-filled syringe or disposable pen, the reconstitution solvent may also be included.

The formulations that best support oral, nasal, pulmonary and/or intra-tracheal dosage forms may be either preserved or unpreserved liquid formulations and/or dry powder or, for oral administration, solid formulations. The preserved or unpreserved liquid formulations will be essentially identical to the formulations described above under preserved or unpreserved liquid parenteral formulations. The pH of the solution should be about 3.0 to 7.0, with a pH greater than or equal to about 5.0 being most preferred to reduce the potential for bronchoconstriction. The dry powder formulations may contain a bulking agent and/or salts to facilitate particle size formation and appropriate particle size distribution. A surfactant and/or salts may also benefit the properties of the particle morphology and/or facilitate tissue uptake of the active ingredient.

These dry powder dosage forms can range from 1% to 100% (w/w), respectively of the active ingredient. It may not be necessary to include a bulking agent and/or salts to facilitate particle size formation and/or distribution. The bulking agent and/or salts may consist of either approximately 0 to 99% (w/w) of a carbohydrate or polyhydric alcohol or approximately 0 to 99% salt or a combination of both leading to the preferred particle size and distribution. A surfactant, preferably about 0.1 to about 1.0% (w/w) of polysorbate 80 or other non-ionic detergent, may be included. Sodium chloride, as well as other excipients, may also be present, if desired. Such excipients, however, must maintain the overall stability of the active ingredient and facilitate the proper level of hydration. The formulations that best support nasal and/or intra-tracheal dosage forms may be either preserved or unpreserved liquid dosage formulations described previously.

Dissolvable gels and/or patches may be used to facilitate buccal delivery. The gels may be prepared from various types of starch and/or cellulose derivatives.

Sublingual delivery may be best supported by liquid formulations similar to those described above as parenteral liquid or parenteral lyophilized formulations after reconstitution except without the need for the dosage form to be an isotonic and/or iso-osmolar solution. Solid dosage forms may be similar to oral solid dosage forms except that they must be readily dissolvable under the tongue.

Oral delivery may be best supported by a liquid (gel cap) formulation that is similar to the parenteral liquid formulation except that the solution may be more concentrated and may contain additional additives to facilitate uptake of the active ingredient by the small intestine. Solid dosage forms will contain inert ingredients along with the active ingredient to facilitate tablet formation. These ingredients may include polyhedral alcohols (such as mannitol), carbohydrates, or types of starch, cellulose derivatives, and/or other inert, physiologically compatible materials. The tablet may be enterically coated to minimize digestion in the stomach and thereby facilitate dissolution and uptake further along the alimentary canal.

The invention also includes preferred dosages for exendins and exendin agonists when given by injection, and when given by other routes. Thus, formulations for exendin and exendin agonists having comparable potency are prepared for the administration by injection and include from about 0.1 to about 0.5 µg per kilogram, given one to three times per day. Typically, for the patient with diabetes who weighs in the range from about 70 kilograms (average for the type 1 diabetic) to about 90 kilograms (average for the type 2 diabetic), for example, this will result in the total administration of about 10 to about 120 µg per day in single or divided doses. If administered in divided doses, the doses are preferably administered two or three times per day, and more preferably, two times per day.

In a preferred injection procedure, the exendin or exendin agonist is administered parenterally, more preferably by injection, for example, by peripheral injection. Preferably, about 1–30 µg to about 1 mg of the exendin or exendin agonist is administered per day. More preferably, about 1–30 µg to about 500 µg, or about 1–30 µg to about 50 λg of the exendin or exendin agonist is administered per day. Most preferably, depending upon the weight of the subject and the potency of the compound administered, about 3 µg to about 50 µg of the exendin or exendin agonist is administered per day. Preferred doses based upon patient weight for compounds having approximately the potency of exendin-4 range from about 0.005 µg/kg per dose to about 0.2 µg/kg per dose. More preferably, doses based upon patient weight for compounds having approximately the potency of exendin-4 range from about 0.02 µg/kg per dose to about 0.1 µg/kg per dose. Most preferably, doses based upon patient weight for compounds having approximately the potency of exendin-4 range from about 0.05 µg/kg per dose to about 0.1 µg/kg per dose. These doses are administered from 1 to 4 times per day, preferably from 1 to 2 times per day. Doses of exendins or exendin agonists will normally be lower if given by continuous infusion. Doses of exendins or exendin agonists will normally be higher if given by non-injection methods, such as oral, buccal, sublingual, nasal, pulmonary or skin patch delivery.

Oral dosages according to the present invention will include from about 50 to about 100 times the active ingredient, i.e., from about 500 to about 12,000 µg per day in single or divided doses, preferably from about 500 to about 5,000 µg per day. Pulmonary dosages according to the present invention will include from about 10 to about 100 times the active ingredient, i.e., from about 100 to about 12,000 µg per day in single or divided doses, preferably about 500 to 1000 µg per day. Nasal, buccal and sublingual dosages according to the present invention will also include from about 10 to about 100 times the active ingredient, i.e., from about 100 to about 12,000 µg per day in single or divided doses.

Preferred dosages for nasal administration are from about 10–1000 to about 1200–12,000 µg per day, for buccal administration from about 10–1000 to about 1200–12,000 µg per day, and for sublingual administration from about 10–1000 to about 1200–8,000 µg per day. Sublingual dosages are preferably smaller than buccal dosages. Administration dosages for exendin agonists having less than or greater than the potency of exendin-4 are increased or decreased as appropriate from those described above and elsewhere herein.

Clinical Studies

As described in Example 10 below, a double blind, placebo-controlled single ascending dose study examining the safety, tolerability, and pharmacokinetics of subcutaneous exendin-4 in healthy volunteers has been completed. Five single subcutaneous doses of exendin-4 (0.01, 0.05, 0.1, 0.2 or 0.3 µg/kg) were studied in 40 healthy male volunteers in the fasting state. Maximum plasma exendin-4 concentrations were achieved between one and two hours post-dose with little difference among the doses examined. Examination of the data indicated a dose dependent increase for $C_{max}$. There were no serious adverse events reported in this study.

In the healthy male volunteers that participated in this study, exendin-4 was well tolerated at subcutaneous doses up to and including 0.1 µg/kg. A decrease in plasma glucose concentration was also observed at this dose. At doses of 0.2 µg/kg and higher, the most commonly observed adverse events were headache, nausea, vomiting, dizziness, and postural hypotension. There was a transient fall in plasma glucose concentration following administration of doses of 0.05 µg/kg and above.

Example 12 below describes a further study of the dose-response relationship for the glucose-lowering effect of exendin-4 at doses less than 0.1 µg/kg. Fourteen subjects [mean (±SE) age 55±2; mean BMI (30.2±1.6 kg/m$^2$)] with type 2 diabetes treated with diet± oral hypoglycemic agents were studied following withdrawal of oral agents for 10–14 days. Assessments were made following randomized, subcutaneous injection of placebo, 0.01, 0.02, 0.05 and 0.1 µg/kg exendin-4 on separate days following an overnight fast. Injections were given immediately before ingestion of a standardized Sustacal® meal (7 kcal/kg) followed by collection of plasma glucose samples at frequent intervals during the subsequent 300 minutes.

The glycemic response was quantified as the time-weighted mean (±SE) change in plasma glucose concentration during the 5-hr period. The response ranged from a +42.0±7.9 mg/dL increment above the fasting glucose concentration for placebo compared to a 30.5±8.6 mg/dL decrement below the fasting glucose concentration with 0.1 µg/kg exendin-4.

The $ED_{50}$ for this glucose lowering effect was 0.038 µg/kg. Exendin-4 doses less than 0.1 µg/kg appeared to disassociate the glucose lowering effects from the gastrointestinal side effects. Example 12 shows that exendin-4 was not only well tolerated at doses less than 0.1 µg/kg, but that these doses substantially lowered postprandial plasma glucose concentrations ($ED_{50}$ of 0.038 µg/kg) in people with type 2 diabetes.

Alternate Routes of Delivery

The feasibility of alternate routes of delivery for exendin-4 has been explored by measuring exendin-4 in the circulation in conjunction with observation of a biologic response, such as plasma glucose lowering in diabetic animals, after administration. Passage of exendin-4 has been investigated across several surfaces, the respiratory tract (nasal, tracheal, and pulmonary routes) and the gut (sublingual, gavage and intraduodenal routes). Biologic effect and appearance of exendin-4 in blood have been observed with each route of administration via the respiratory tract, and with sublingual and gavaged peptide via the gastrointestinal tract.

Intra-tracheal Administration—As described herein, intra-tracheal administration of exendin-4 into fasted rats (20 µg/50 µL/animal) produced a rise in the mean plasma exendin-4 concentration to 2060±960 µg/mL within 5–10 minutes after administration. Elevated plasma exendin-4 concentrations were maintained for at least 1 hour after instillation (see FIG. 4). In diabetic db/db mice, intra-tracheal instillation of exendin-4 (1 µg/animal) lowered plasma glucose concentration by 30% while that in the vehicle control group increased by 41% 1.5 hours after treatment. In these animals the mean plasma concentration of exendin-4 was 777±365 µg/ml at 4.5 hours after treatment (see FIGS. 5a and 5b).

Figure 6B:
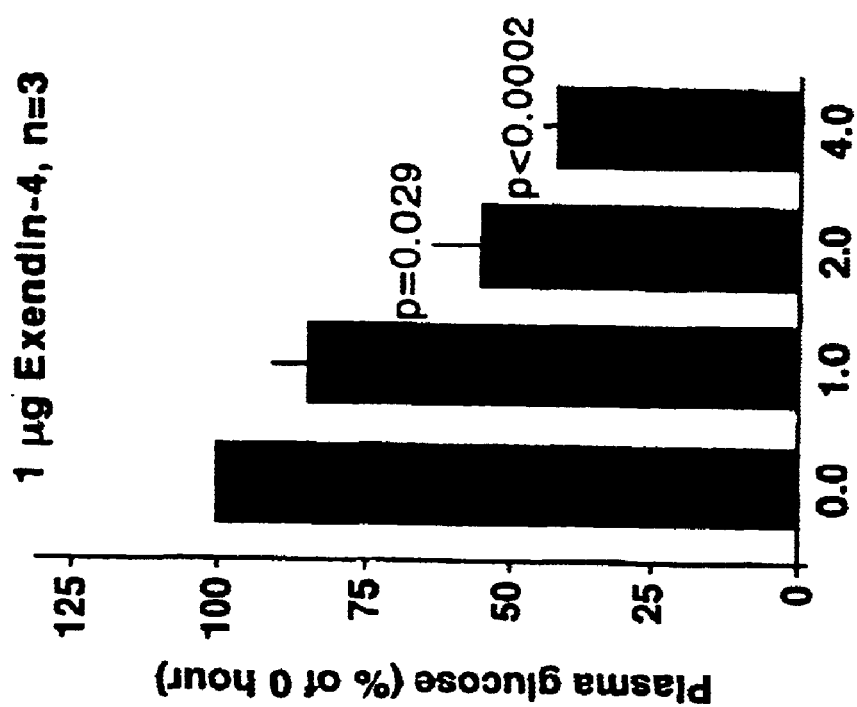
FIGS. 6a and 6b depict the effect of intra-tracheal administration of exendin-4 on plasma glucose in db/db mice.
Figure 6A:
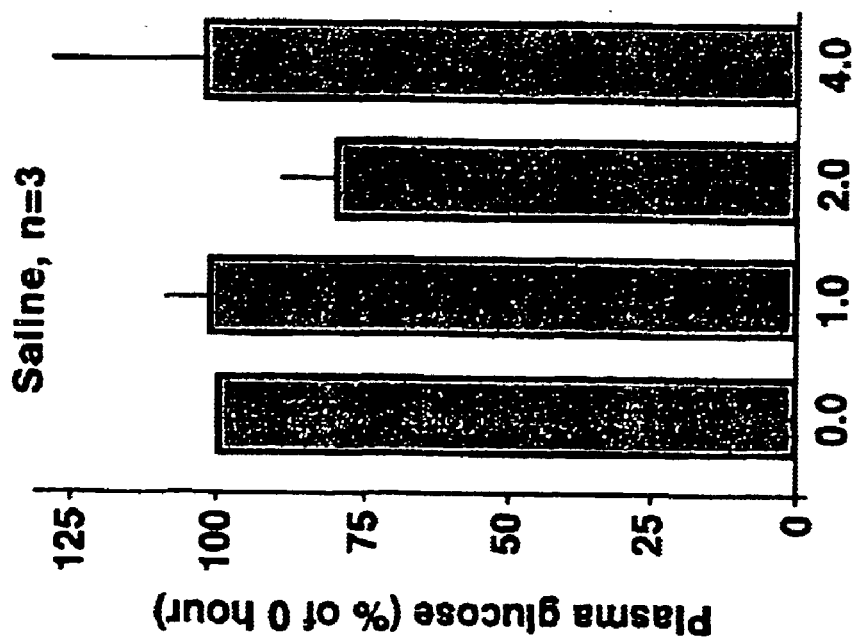

In diabetic ob/ob mice, intra-tracheal instillation of exendin-4 (1 µg/animal) decreased plasma glucose concentration to 43% of the pre-treatment level after 4 hours while that in the vehicle control group was not changed (see FIGS. 6a and 6b).

Figure 7B:
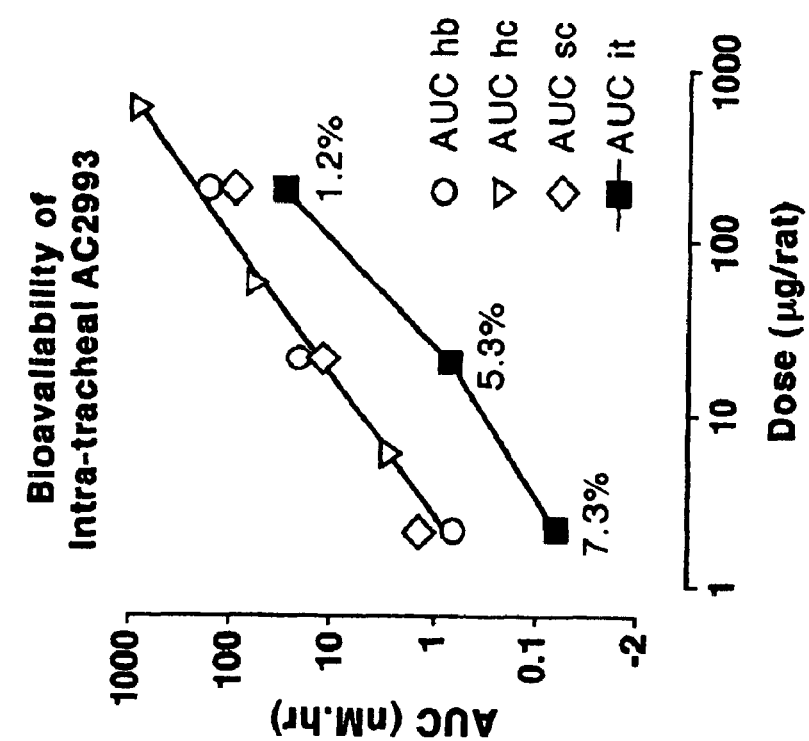
FIG. 7b depicts the bioavailability of exendin-4 following intra-tracheal instillation into rats.
Figure 7A:
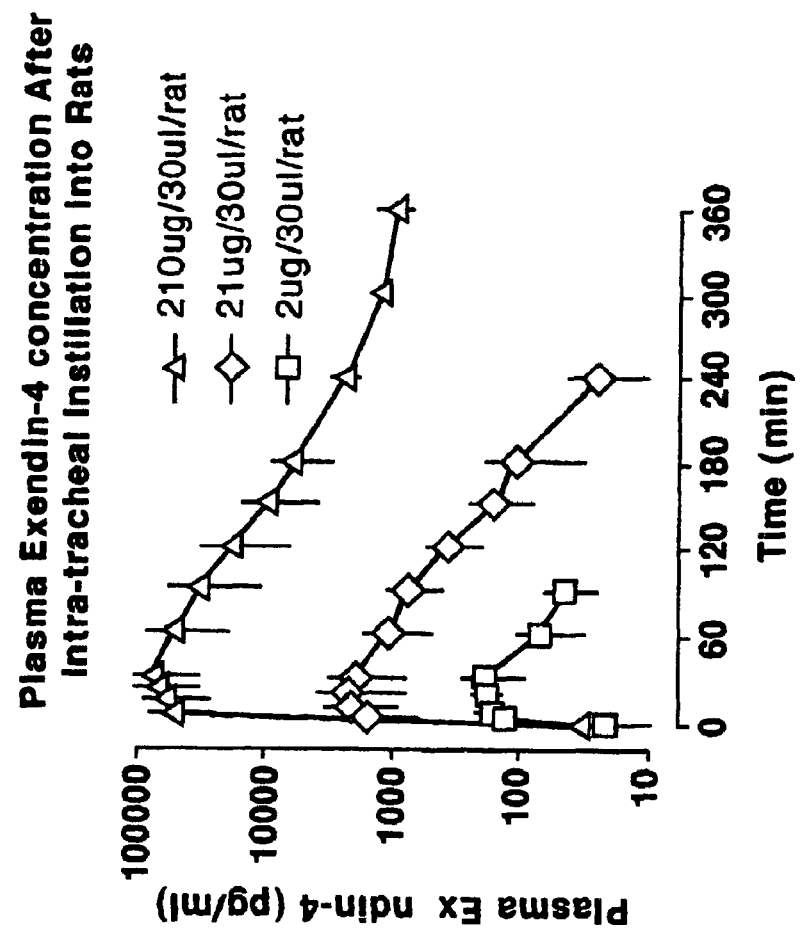
FIG. 7a depicts the plasma exendin-4 concentration after intra-tracheal instillation into rats.
Figure 10:
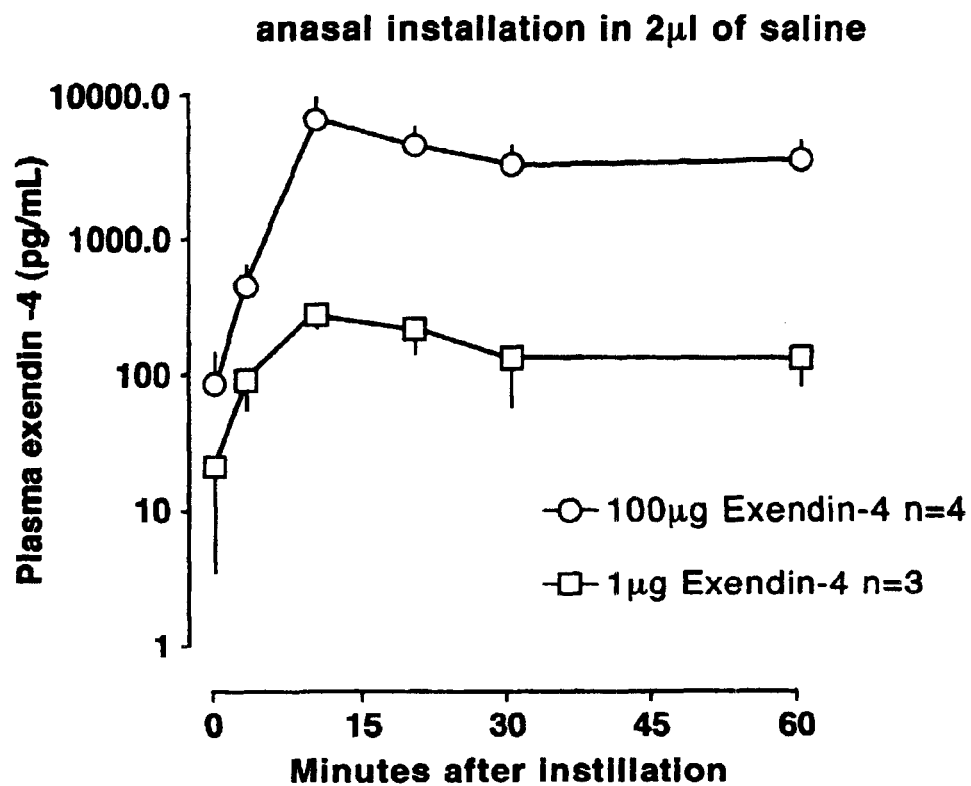
FIG. 10 depicts plasma exendin-4 concentrations in rats after intra-nasal administration of exendin-4.
Figure 12A:
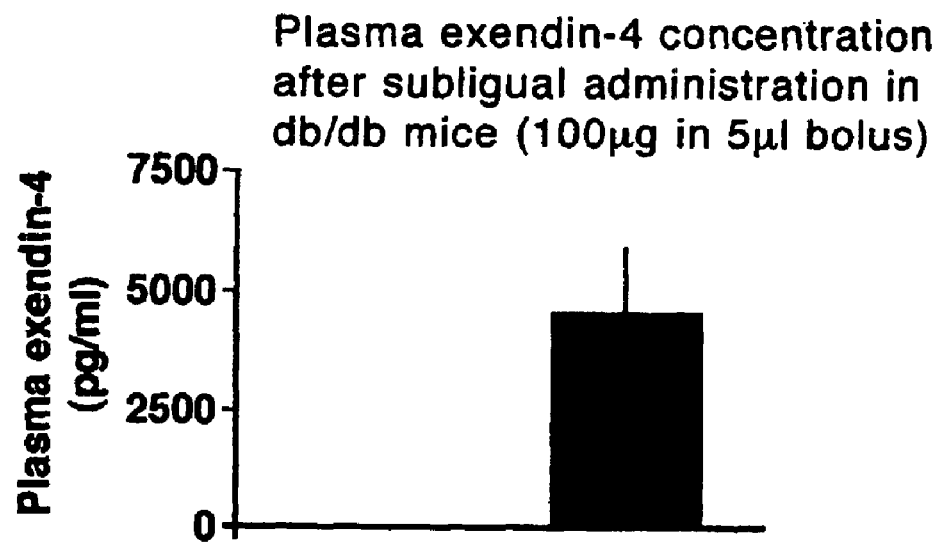
FIG. 12a depicts the plasma exendin-4 concentration after sublingual administration to db/db mice.
Figure 12B:
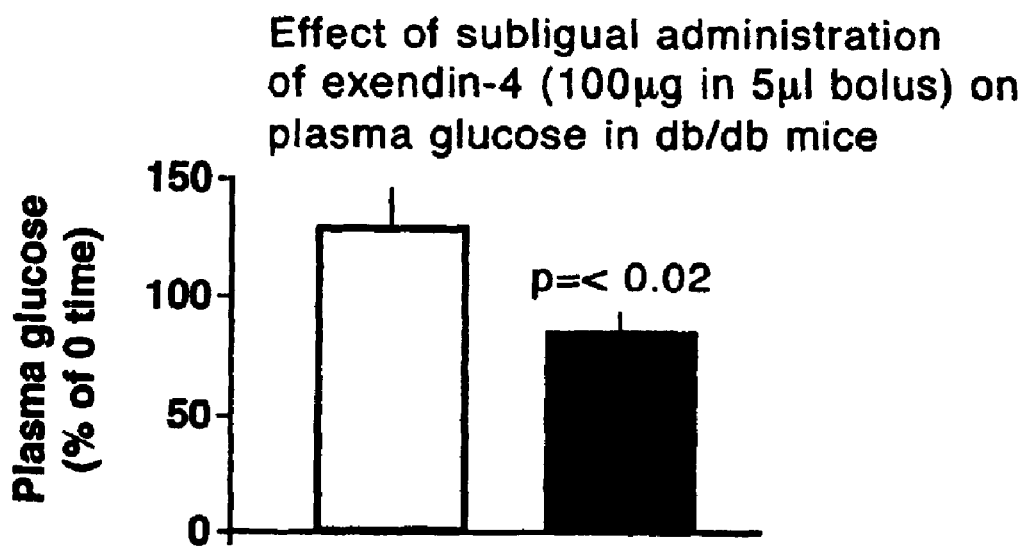
FIG. 12b depicts the effect of sublingual administration of exendin-4 on plasma glucose in db/db mice.
Figure 12C:
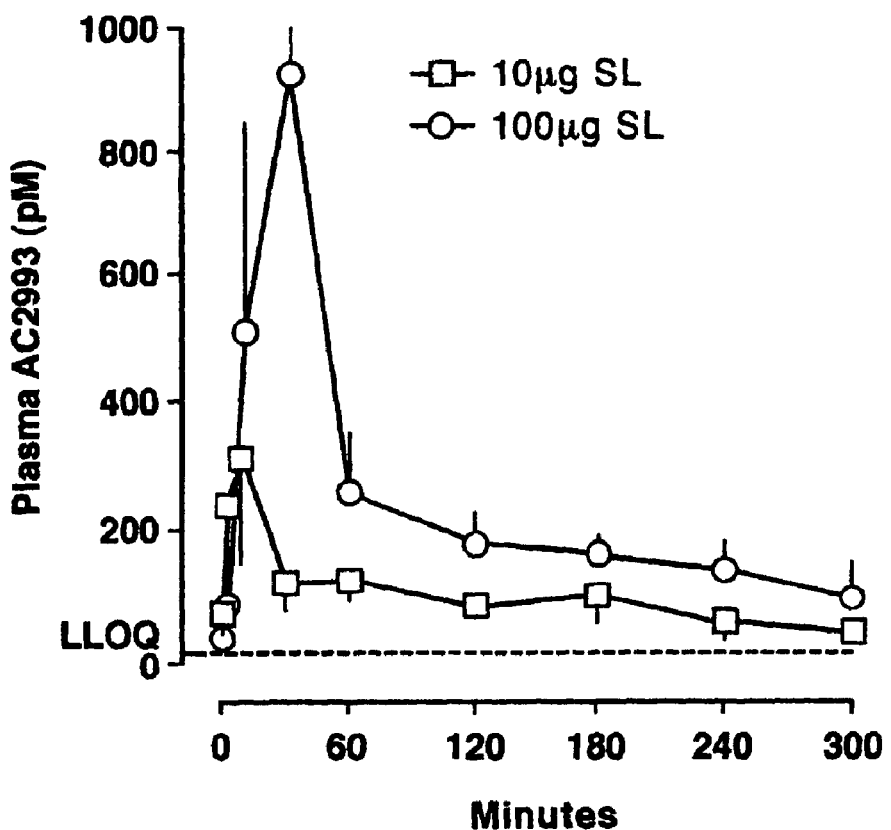
FIG. 12c depicts the plasma exendin-4 concentration after sublingual administration to rats.
Figure 12D:
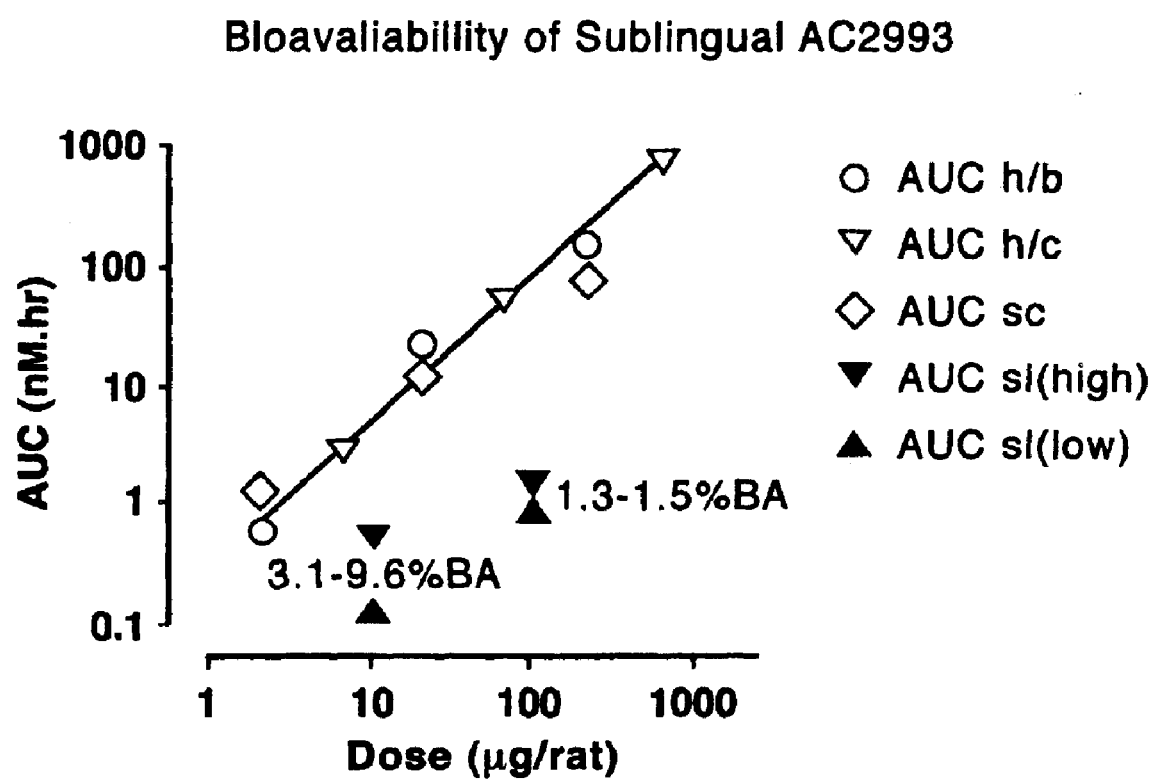
FIG. 12d depicts the bioavailability of exendin-4 after sublingual administration.
Figure 12E:
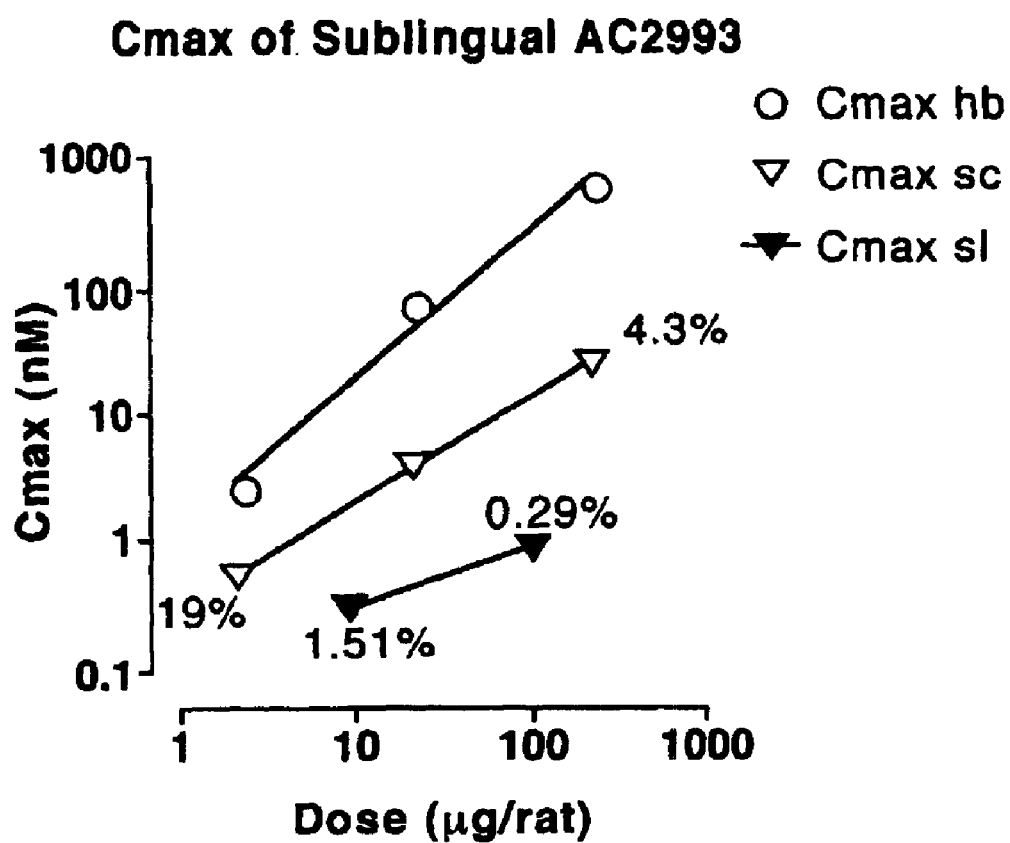
FIG. 12e depicts the Cmax of sublingual exendin-4.

Nine overnight-fasted male Sprague Dawley rats (age 96–115 days, weight 365–395, mean 385 g) were anesthetized with halothane, tracheotomized, and catheterized via the femoral artery. At t=O min, 30 µL of saline in which was dissolved 2.1 µg (n=3), 21 µg (n=3) or 210 µg of exendin-4 was instilled into the trachea beyond the level of intubation. Blood samples were taken after 5, 10, 20, 30, 60, 90, 120, 150, 180, 240, 300 and 360 min, centrifuged and plasma stored at −20° C. for subsequent immunoradiometric (IRMA) assay directed to N-terminal and C-terminal epitopes of the intact exendin-4 molecule. Following intra-tracheal administration, 61–74% of peak plasma concentration was observed within 5 min. Tmax occurred between 20 and 30 min after administration. AUC and Cmax were proportional to dose. At a dose of 2.1 µg (1.5 nmol/kg), resulting in plasma concentrations of ~50 pM (where glucose-lowering effects in man are observed), bioavailability was 7.3%. The coefficient of variation was 44%. At higher doses, bioavailability was slightly lower, and the CV was higher (see FIGS. 7a and 7b). Via the tracheal route of administration, the t½ (defined pragmatically as time for plasma to fall below 50% of Cmax) was 30–60 min for the lowest dose and 60–90 min for the 2 higher doses. In sum, biologically effective quantities of exendin-4 are rapidly absorbed via the trachea without evoking apparent respiratory distress. The respiratory tract is a viable route of administration of exendin-4.

Pulmonary Administration—Increased plasma concentrations of exendin-4 were detected in rats exposed to aerosolized exendin-4. Exposure of rats to approximately 8 ng of aerosolized exendin-4 per mL of atmosphere for 10 minutes resulted in peak plasma exendin-4 concentrations of 300–1900 pg/mL 5 minutes following treatment (see FIG. 8). Similar exposure of diabetic db/db mice to aerosolized exendin-4 lead to a 33% decrease in plasma glucose concentration after 1 hour, when a mean plasma exendin-4 concentration of 170±67 pg/mL was detected. Diabetic db/db mice in the control group exposed to aerosolized saline recorded no change in plasma glucose (see FIGS. 9*a* and 9*b*).

Nasal administration—Application of exendin-4 into the nasal cavity of rats led to a rise in plasma concentrations. Peak values of 300 pg/mL and 6757 pg/mL were detected 10 minutes after administration of 1 μg and 100 μg exendin-4 (dissolved in 2 μL saline), respectively (see FIG. 10).

Administration via the Gut—Male db/db mice (approximately 50 g body weight) were fasted for 2 h and before and after an intra- gastric administration of saline or exendin-4 (exendin-4). A 9% decrease in plasma glucose concentration was observed with 1 mg/200 μl/animal and a 15% decrease was observed with 3 mg/200 μl/animal, compared with a 10% incase plasma glucose in the controls one hour after treatment (see FIG. 11).

Sublingual Administration—Sublingual application of exendin-4 (100 μg/5 μL/animal) to diabetic db/db mice led to a 15% decrease in plasma glucose concentration one hour after treatment. A 30% increase was observed for the control group receiving saline. The mean exendin-4 plasma level at 60 minutes was 4520±1846 pg/mL (see FIGS. 12*a*, 12*b*, and 12*c*).

Eight Sprague Dawley rats (−300 g) were briefly anesthetized with metophane while a solution containing 10 μg/3 μL (n=4) or 100 μg/3 μL (n=4) was pipetted under the tongue. Blood samples were subsequently collected from the topically anesthetized tail and assayed for exendin-4 by IRMA. Plasma concentrations had begun to rise by 3 min after administration and were maximal 10 min and 30 min after administration (10 μg and 100 μg doses, respectively). Plasma exendin-4 concentration subsequently remained above the lower limit of quantitation (LLOQ) beyond 5 hours. Area-under-the-curve to the end of each experiment was calculated by the trapezoidal method. Two numbers were derived, one derived from total immunoreactivity, the other derived from the increment above the non-zero value present at t=0. These values were compared to historical intravenous bolus data in the same animal model to obtain, respectively, high and low estimates of bioavailability. For the 10 μg dose, sublingual bioavailability was 3.1–9.6%, and for a 100 μg dose, bioavailability was lower at 1.3–1.5%. Variability of AUC was greatest in the first hour after administration (CV 74% and 128% for 10 and 100 μg doses). For the S-hour integral, coefficient of variation of the AUC was 20% and 64%, respectively. Peak plasma concentration (Cmax) occurred as rapidly after sublingual administration as after subcutaneous administration (Tmax ~30 min). Cmax after sublingual administration of 10 μg exendin-4 was 1.5% that after an intravenous bolus, but 14.5% of that obtained after a subcutaneous bolus. Cmax after sublingual administration of 100 μg exendin-4 was only 0.29% of that observed after an intravenous bolus, and 6.1% of that obtained after a subcutaneous bolus (see FIGS. 12*d* and 12*e*). Thus, exendin-4 can be delivered at bioeffective doses via the sublingual route. Bioavailability and Cmax were greatest, $T_{max}$ was shortest, and variability of availability was least with the lowest sublingual dose. The lowest sublingual dose resulted in plasma concentrations similar to those that are predicted to be effective in lowering glucose in humans (−50–100 pM).

To assist in understanding the present invention the following Examples are included which describe the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Preparation of Exendin-3

His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-$NH_2$ [SEQ. ID. NO. 1]

The above amidated peptide was assembled on 4-(2'-4'-dimethoxyphenyl)-Fmoc aminomethyl phenoxy acetamide norleucine MBHA resin (Novabiochem, 0.55 mmole/g)

using Fmoc-protected amino acids (Applied Biosystems, Inc.). In general, single-coupling cycles were used throughout the synthesis and Fast Moc (HBTU activation) chemistry was employed. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis of Examples 1 and 2 were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (reverse phase-high performance liquid chromatography) (gradient 30% to 60% Solvent B in Solvent A over 30 minutes) of the lyophilized peptide gave product peptide having an observed retention time of 19.2 minutes.

EXAMPLE 2

Preparation of Exendin-4
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-$NH_2$ [SEQ. ID. NO. 2]
The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Exe din-3 as describe in Example 1. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 14.9 minutes. Electrospray Mass Spectrometry (M): calculated 4186.6; found 8186.0 to 4186.8 (four lots).

EXAMPLE 3

Exendin-4 is a Circulating, Meal-Related Peptide in the Gila Monster

This experiment investigated whether exendin-4 has a metabolic role in the Gila monster lizard itself. To investigate whether exendin-4 appeared in the blood of the Gila monster in response to feeding, blood was sampled from one animal fasted for 7 weeks, before and 30 min after ingestion of a small rat. Plasma was assayed for full-length exendin-4 using an immunoradiometric assay with monoclonal antibody pairs directed to epitopes at N- and C-termini of exendin-4. Fasting plasma exendin-4 concentration was 76 pg/mL, near the lower limit of quantitation. After eating, this value rose 300-fold to 23,120 pg/mL.

In a second experiment, serial samples were taken from two animals fasted five weeks before and after ingestion of one or two small rats (47–49 g). Plasma exendin-4 concentration rose 23- to 36-fold (to 4860, 8340 pg/mL) immediately after eating, consistent with a direct passage of exendin-4 from the salivary gland to blood. After eating a second rat (t=30 min), plasma exendin-4 concentration in one Gila rose further to 27,209 pg/mL. Plasma exendin-4 concentration decayed with a t½ of 5.00 and 5.33 hours, respectively. In conclusion, exendin-4, known to originate from the salivary gland of the Gila monster, appears in high concentration in the blood immediately after eating. This may represent a meal-related signal to inhibit further eating and promote nutrient storage.

EXAMPLE 4

Exendin-4 Decreases Glucagon Secretion During Hyperglycemic Clamps in Diabetic Fatty Zucker Rats Absolute or relative hyperglucagonemia is often a feature of type 1 and type 2 diabetes mellitus, and the suppression of excessive glucagon secretion is a potential benefit of therapy using glucagonostatic agents. In this Example, the effect of exendin-4 on glucagon secretion in male anaesthetized Diabetic Fatty Zucker (ZDF) rats was examined. Using an hyperinsulinemic hyperglycemic clamp protocol, factors tending to influence glucagon secretion were held constant. Plasma glucose was clamped at ~34 mM 60 min before beginning intravenous infusions of saline (n=7) or exendin-4 (0.21 μg+2.1 μg/mL/h; n=7). Plasma glucagon concentration measured before these infusions were similar in both groups (306±30 pM versus 252±32 pM, respectively; n.s.).

Mean plasma glucagon concentration in exendin-4 infused rats was nearly half of that in saline-infused rats in the final 60 minutes of the clamp (165±18 pM versus 298±26 pM, respectively; P<0.002). The hyperglycemic clamp protocol also enabled measurement of insulin sensitivity. Glucose infusion rate during the clamp was increased by 111±7% in exendin-4-treated versus control rats (P<0.001). In other words, exendin-4 exhibited a glucagonostatic effect in ZDF rats during hyperglycemic clamp studies, an effect that will be of therapeutic benefit in diabetic humans.

EXAMPLE 5

Pharmacokinetics of Exendin-4 In the Rat Following Intravenous, Subcutaneous and Intraperitoneal Administration This Example describes work to define the plasma pharmacokinetics of exendin-4 in rats (~350 g body weight each) following 2.1, 21, 210 μg/rat i.v. bolus, s.c. and i.p. administration and 2.1, 21, 210 μg/hr/rat i.v. infusion (3 hr). Serial samples of plasma (~120 μL) were assayed using a validated immunoradiometric assay (IRMA). This sandwich-type assay uses mouse-based monoclonal antibodies that react with exendin-4 but do not react with GLP-1 or tested metabolites of exendin-4 or GLP-1. The lower limit of quantitation was 15 pM (63 pg/mL). The estimated t½ for exendin-4 was 18–41 min for i.v. bolus, 28–49 for i.v. continuous, 90–216 min for s.c. and 125–174 min for i.p. injection. Bioavailability was 65–76% for s.c. and i.p. injection. Clearance determined from the i.v. infusion was 4–8 mL/min. Both $C_{max}$ and AUC values within each route of administration were proportional to dose. Volume of distribution was 457–867 mL. Clearance and bioavailability were not dose dependent. $C_{max}$ (or steady-state plasma concentration; $C_{ss}$) is shown in the table below

|  | Cmax or Css (nM) | | | |
| --- | --- | --- | --- | --- |
| Route Dose | Intravenous bolus | Intravenous infusion | Subcutaneous | Intraperitoneal |
| 2.1 μg | 2.9 ± 0.4 | 1.1 ± 0.1 | 0.56 ± 0.12 | 0.26 ± 0.04 |
| 21 μg | 70 ± 3 | 19 ± 1.9 | 4.1 ± 1.5 | 3.9 ± 1 |
| 210 μg | 645 ± 12 | 262 ± 60 | 28 ± 4 | 35 ± 6 |

EXAMPLE 6

Comparison of the Insulinotropic Actions of Exendin-4 and Glucagon-Like Peptide-1 (GLP-1) During an Intravenous Glucose Challenge in Rats This experiment compares the insulinotropic actions of synthetic exendin-4 and GLP-1 in vivo following an intravenous (i.v.) glucose challenge in rats. Sprague-Dawley rats (~400 g) were anesthetized with halothane and cannulated via the femoral artery and saphenous vein. Following a 90-min recovery period, saline or peptide (30 pmol/kg/min each) was administered i.v. (1 ml/h for 2 hours; n=4–5 for each group). Thirty min after infusion commenced, D-glucose (5.7 mmol/kg, 0.8 ml) was injected i.v. In saline-treated, exendin-4-treated and GLP-1-treated rats, plasma glucose concentrations were similar before injection (9.3±0.3, 9.7±0.3, 10.3±0.4 mM), increased by similar amounts after glucose injection (21.7, 21.3, 23.7 mM), and resulted in a similar 60-min glucose AUC (987±39, 907±30, 1096±68 mM·min, respectively). That is, the glycemic stimulus was similar in each treatment group. Plasma insulin concentration in saline-treated rats increased 3.3-fold with the glucose challenge (230±53 to a peak of 765±188 pM). With exendin-4 infusion, the increase in plasma insulin concentration was 6.8-fold (363±60 to 2486±365 pM). With GLP-1 the increase in plasma insulin concentration was 2.9-fold (391±27 to 1145±169 pM), which was similar to that obtained in saline-treated rats. The 60-min insulin AUC in saline-treated rats was 24±6 nM·min, was increased 2.8-fold in exendin-treated rats (67±8 nM·min; P<0.003 versus saline; P<0.02 versus GLP-1) and by 20% in GLP-1-treated rats (n.s. versus saline). Amplification of glucose-stimulated insulin release by exendin-4 was also tested at infusion rates of 3 and 300 pmol/kg/min and shown to be dose-dependent. Thus, exendin-4 is more potent and/or effective than GLP-1 in amplifying glucose-stimulated insulin release in intact rats.

EXAMPLE 7

Development and Validation of an Immunoradiometric Assay (IRMA) for the Quantitation of Exendin-4 IN Plasma and its Application to Preclinical Toxicity and Phase I Clinical Evaluations A sensitive and specific sandwich-type immunoradiometric (IRMA) assay was developed for quantitation of plasma exendin-4 concentration using synthetic exendin-4 as the immunogen. One mouse-derived monoclonal antibody recognizes a C-terminal epitope on exendin-4 (capture antibody) but does not cross-react with GLP-1. The second antibody (detector antibody labeled with $^{125}$I) recognizes an N-terminal epitope on exendin-4 and GLP-1, and requires a terminal histidine for binding. Thus, the assay as a whole does not detect GLP-[(7-36)NH2, GLP-1 (7-36)COOH or exendin (3-39). Assay validation in rat, monkey, dog, rabbit and human plasmas showed inter- and intra-assay coefficients of variation <20% and <10%, respectively, accuracy of ±15% with target low, mid and high controls, and lower and upper limits of quantitation of 62.8 and 2512 pg/mL, respectively. Plasma samples from 28-day subcutaneous toxicity evaluations of exendin-4 in rats and monkeys and a Phase I clinical study in normal subjects were evaluated using the IRMA. The $C_{max}$ values in the animals studies are shown in the table below. Human samples from subcutaneous administration of 0.05, 0.1, 0.2 and 0.3 μg/kg yielded $C_{max}$ values of 90, 224, 370 and 587 pg/mL.

|  | Cmax (pg/mL) | | |
| --- | --- | --- | --- |
| Dose (μg/kg) | 10 | 100 | 1000 |
| Rat | 7,000 | 127,000 | 1,180,000 |
| Monkey | 20,000 | 170,000 | 1,890,000 |

EXAMPLE 8

Comparison of GLP-1 Receptor Binding/Activating and Glucose-Lowering Effects Of GLP-1 and Exendin-4

Exendin-4 was synthesized by solid phase peptide synthesis techniques and compared to synthetic GLP-1 in terms of in vitro binding to, and activation of, GLP-1 receptors, and in vivo in terms of lowering plasma glucose in diabetic db/db mice. In a plasma membrane preparation of a rat insulinoma cell line (RINm5f) that expresses the GLP-1 receptor, the peptides were assayed for their ability to bind and displace radiolabeled GLP-1 and for their ability to stimulate the production of cAMP. The relative order of binding potency was found to be GLP-1>exendin-4. The relative order of cyclase activation was GLP-1=exendin-4. Affinities, as shown in the table below, differ over a 4- to 5-fold range. In contrast, in vivo glucose lowering potency differed over a 3430-fold range. Exendin-4 was 3430-fold more potent than GLP-1. The in vivo potency of exendin-4 does not match potency at the GLP-1 receptor, and is likely the culmination of an aggregate of properties.

|  | Binding IC50 (nM) | Cyclase EC50 (nM) | Glucose-lowering ED50 (μg) |
| --- | --- | --- | --- |
| GLP-1 | 0.15 | 0.28 | 20.6 |
| Exendin-4 | 0.66 | 0.30 | 0.006 |

EXAMPLE 9

Comparison of Glycemic Indices and Insulin Sensitivity in Pair-Fed and Exendin-4-Treated Diabetic Fatty Zucker Rats This Example tests whether the beneficial effects of exendin-4 in ZDF rats were secondary to changes in food intake. It compares effects obtained with exendin-4 to effects observed in saline-treated matched animals who consumed the same amount of food as was eaten by ZDF rats injected subcutaneously twice daily with 10 μg exendin-4. Plasma glucose and HbAlc were measured weekly for 6 weeks. One day after the last treatment, animals were anesthetized with halothane and subjected to an hyperinsulinemic (50 mU/kg/min) euglycemic clamp. Changes in HbAlc over 6 weeks differed between treatment groups (P<0.001 ANOVA), increasing in ad lib fed (n=5) and pair fed (n=5) rats, but decreasing in exendin-4-treated rats (n=5). Similarly, changes in plasma glucose differed between treatment groups (P<0.002 ANOVA), increasing in ad lib fed and pair fed ZDF rats, and decreasing in ZDF rats treated with exendin-4. In the final hour of a 3-hour clamp protocol, glucose infusion rate in exendin-4-treated rats tended to be higher than in pair fed (+105%) and ad lib fed (+20%) controls, respectively (10.14±1.43 n=5, 8.46±0.87 n=4, 4.93±2.02 mg/kg/min n=3; n.s. P=0.09 ANOVA). Another index of insulin sensitivity, plasma lactate concentration, differed significantly between treatment groups (P<0.02 ANOVA) and was lowest in exendin-4-treated rats. Thus, exendin-4 treatment is associated with improvement in glycemic indices and in insulin sensitivity that is partly, but not fully, matched in controls fed the same amount of food, indicating that improvements in metabolic control with exendin-4 in ZDF rats are at least partly due to mechanisms beyond caloric restriction.

EXAMPLE 10

Clinical Studies and the Stimulation of Endogenous Insulin Secretion By Subcutaneous Synthetic Exendin-4 In Healthy Overnight Fasted Volunteers In a double blind, placebo-controlled single ascending dose clinical trial to explore safety and tolerability and pharmacokinetics of synthetic exendin-4, exendin-4 formulated for subcutaneous injection was evaluated in healthy male volunteers while assessing effects upon plasma glucose and insulin concentrations. Five single subcutaneous doses of exendin-4 (0.01, 0.05, 0.1, 0.2 or 0.3 µg/kg) were studied in 40 healthy male volunteers in the fasting state. Maximum plasma exendin-4 concentrations were achieved between 1 and 2 hours post-dose with little difference among the doses examined. Examination of the data indicated a dose dependent increase for $C_{max}$. There were no serious adverse events reported in this study and in the healthy male volunteers that participated in this study, exendin-4 was well tolerated at subcutaneous doses up to and including 0.1 µg/kg. A decrease in plasma glucose concentration was also observed at this dose. At doses of 0.2 µg/kg and higher, the most commonly observed adverse events were headache, nausea, vomiting, dizziness, and postural hypotension. There was a transient fall in plasma glucose concentration following administration of doses of 0.05 µg/kg and above.

Forty healthy, lean (mean BMI (±SE) 22.7±1.2) subjects aged 18–40 years were randomly assigned to 5 groups. Within each group of 8 subjects, 6 were assigned to exendin-4 and 2 to placebo (PBO). Exendin-4 (0.01, 0.05, 0.1, 0.2 or 0.3 µg/kg) or placebo was administered following an overnight fast and plasma exendin-4, glucose and insulin concentrations monitored along with safety and tolerability. No safety issues were observed. Doses ≦0.1 µg/kg were tolerated as well as PBO whereas 0.2 and 0.3 µg/kg elicited a dose-dependent increase in nausea and vomiting. Peak plasma exendin-4 concentrations rose dose-dependently and following 0.1 µg/kg, exendin-4 immunoreactivity persisted for 360 min. Plasma glucose decreased following all doses, except 0.01 µg/kg, reached a nadir by 30 min and returned back to baseline within 180 min. Subjects receiving 0.3 µg/kg received a caloric beverage 30 minutes after dosing, precluding comparison of their data. Mean change in plasma glucose (0–180 min): 0.03±0.07, −0.07±0.08, −0.38±0.14, −0.85±0.13 and −0.83±0.23 mmol/L for PBO, 0.01, 0.05, 0.1, and 0.2 µg/kg respectively; P≦0.02 versus PBO. The lowest plasma glucose recorded was 3.4 mmol/L. Corresponding mean changes in plasma insulin (0–120 min) were 0.43±0.59, 2.37±0.58, 2.28±0.66, 4.91±1.23, and 14.00±3.34 µU/mL; P≦0.01 versus PBO for the 0.1 and 0.2 µg/kg groups. Thus, in healthy, overnight fasted volunteers, subcutaneous injection of exendin-4 (1) presented no safety issues, (2) was well-tolerated at doses ≦0.1 µg/kg, (3) led to exendin-4 immunoreactivity in plasma for up to 6 hrs, (4) increased plasma insulin and lowered plasma glucose in a dose-dependent manner without inducing hypoglycemia.

EXAMPLE 11

Effectiveness Of Alternate Delivery Of Exendin-4 In Rodents

This Example tested the delivery of exendin-4 by means alternative to injection, and examined its ability to traverse mucosal surfaces in sufficient quantities to exert biological effect. Changes in concentration of plasma glucose and of intact synthetic exendin-4 (measured by a 2-site immunoradiometric assay) were observed in db/db mice administered a saline solution containing differing doses of synthetic exendin-4 via the trachea, via an aerosol mist (pulmonary), via gavage (oral), and under the tongue (sublingual). The same routes of administration, as well as intraduodenally and nasally, were tested in rats, and bioavailability was calculated, for example, for sublingual and intra-tracheal routes. Exendin-4 administered via each of the above routes in mice resulted in significant glucose-lowering activity 1 to 4 hours after administration (db/db mice intra-tracheal P<0.02; ob/ob mice intra-tracheal P<0.0002; db/db mice aerosol P<0.0001; gavage P<0.002; sublingual P<0.02). Dose-dependent increases in plasma exendin-4 concentration were up to 777±365 pg/mL (db/db mice intra-tracheal); 170±67 pg/mL (db/db mice aerosol); 4520±1846 pg/mL (db/db mice sublingual). Similarly, in rats, exendin-4 concentrations were observed up to 68,682±38,661 pg/mL (intra-tracheal); 1900 pg/mL (pulmonary); 6757 pg/mL (nasal); 3,862±2,844 pg/mL (sublingual); but no apparent absorption or biological activity when delivered intraduodenally. Bioavailability of exendin-4 in saline was ~7.3% at lower doses when delivered via the trachea, where 61–74% of Cmax was observed within 5 min. Kinetics thereafter were similar to those observed after subcutaneous administration. Bioavailability of exendin-4 in saline delivered under the tongue was 3.1–9.6% at lower doses. These studies support the delivery of exendin-4 and peptide agonist analogs thereof in biologically effective quantities via convenient non-injectable routes.

EXAMPLE 12

A Single-Blind, Placebo Controlled Study On The Metabolic Effects Of A Range Of Doses Of Synthetic Exendin-4 Given By Subcutaneous Injection to People with Type 2 Diabetes Mellitus This Example describes the results of a two-part, single-blind, placebo controlled study to examine the metabolic effects of a range of doses of synthetic exendin-4 given by the subcutaneous route to subjects with Type II diabetes mellitus. The subjects involved in the study were individuals diagnosed with Type II diabetes and being controlled with diet and/or with oral hypoglycemic agents (OHAs) and with $HbA_{1c}$ concentration ≦7.0% but ≧12.0% at the screening visit.

The study commenced with a screening visit, after which the subjects taking OHAs were instructed to stop this medication and return to the clinic approximately 14 days later when the effects of the OHA dissipated. Subjects who participated in Part 1 arrived at the clinic the afternoon prior to the first dose and began the three or four scheduled dosing days. Each dosing event was scheduled to be 24 hours apart.

Following consent and screening, subjects were randomly assigned to receive synthetic exendin-4 or placebo. In the first portion of the study, six subjects were confined to an in-patient clinical research unit for three to four days and assigned to one of 4 treatment sequences, where they were to receive each of the following doses: placebo or synthetic exendin-4 at 0.1 or 0.01, or possibly 0.001 µg/kg. Doses were administered subcutaneously following an overnight fast. A standardize liquid meal was given 15 minutes after injection of the study medication. The table below illustrates the dosing schedule for Part 1:

|  | Day 1 | Day 2 | Day 3 | Day 4* |
|---|---|---|---|---|
| Subject 1 | Placebo | 0.1 µg/kg | 0.01 µg/kg | 0.001 µg/kg |
| Subject 2 | Placebo | 0.1 µg/kg | 0.01 µg/kg | 0.001 µg/kg |
| Subject 3 | 0.1 µg/kg | Placebo | 0.01 µg/kg | 0.001 µg/kg |
| Subject 4 | 0.1 µg/kg | Placebo | 0.01 µg/kg | 0.001 µg/kg |
| Subject 5 | 0.1 µg/kg | 0.01 µg/kg | Placebo | 0.001 µg/kg |
| Subject 6 | 0.1 µg/kg | 0.01 µg/kg | Placebo | 0.001 µg/kg |

*Will only be completed if an effect on glucose is observed on Day 3.

In the second part of the study, approximately three days after the completion of Part 1, eight subjects were also confined to an in-patient clinical research unit for four days. The subjects were different subjects from those who participated in Part 1. The study procedures and schedule of events during Part 2 were consistent with Part 1. The doses were determined after the effect on glucose in Part 1 was analyzed.

Because there was no significant effect seen at 0.01 µg/kg during Part 1, subjects were dosed according to the following schedule in Part 2:

|  | Day 1 | Day 2 | Day 3 | Day 4 |
|---|---|---|---|---|
| Group A | Placebo | 0.02 µg/kg | 0.05 µg/kg | 0.1 µg/kg |
| Group B | 0.02 µg/kg | 0.1 µg/kg | Placebo | 0.05 µg/kg |
| Group C | 0.05 µg/kg | Placebo | 0.1 µg/kg | 0.02 µg/kg |
| Group D | 0.1 µg/kg | 0.05 µg/kg | 0.02 µg/kg | Placebo |

Subjects who participated in Part 2 began their dosing following review of the data from Part 1 in the same manner. All subjects returned to the clinic 4 to 6 days after discharge from the in-patient unit for a safety reassessment.

The synthetic exendin-4 used for the study was a clear colorless sterile solution for subcutaneous injection, formulated in sodium acetate buffer (pH 4.5) and containing 4.3% mannitol as an iso-osmolality modifier. The strength of synthetic exendin-4 injection was 0.1 mg/mL. One mL of solution was supplied in 3 mL vials with rubber stoppers. Placebo solution was made from the same sterile formulation but without the drug substance, synthetic exendin-4.

Figure 16:
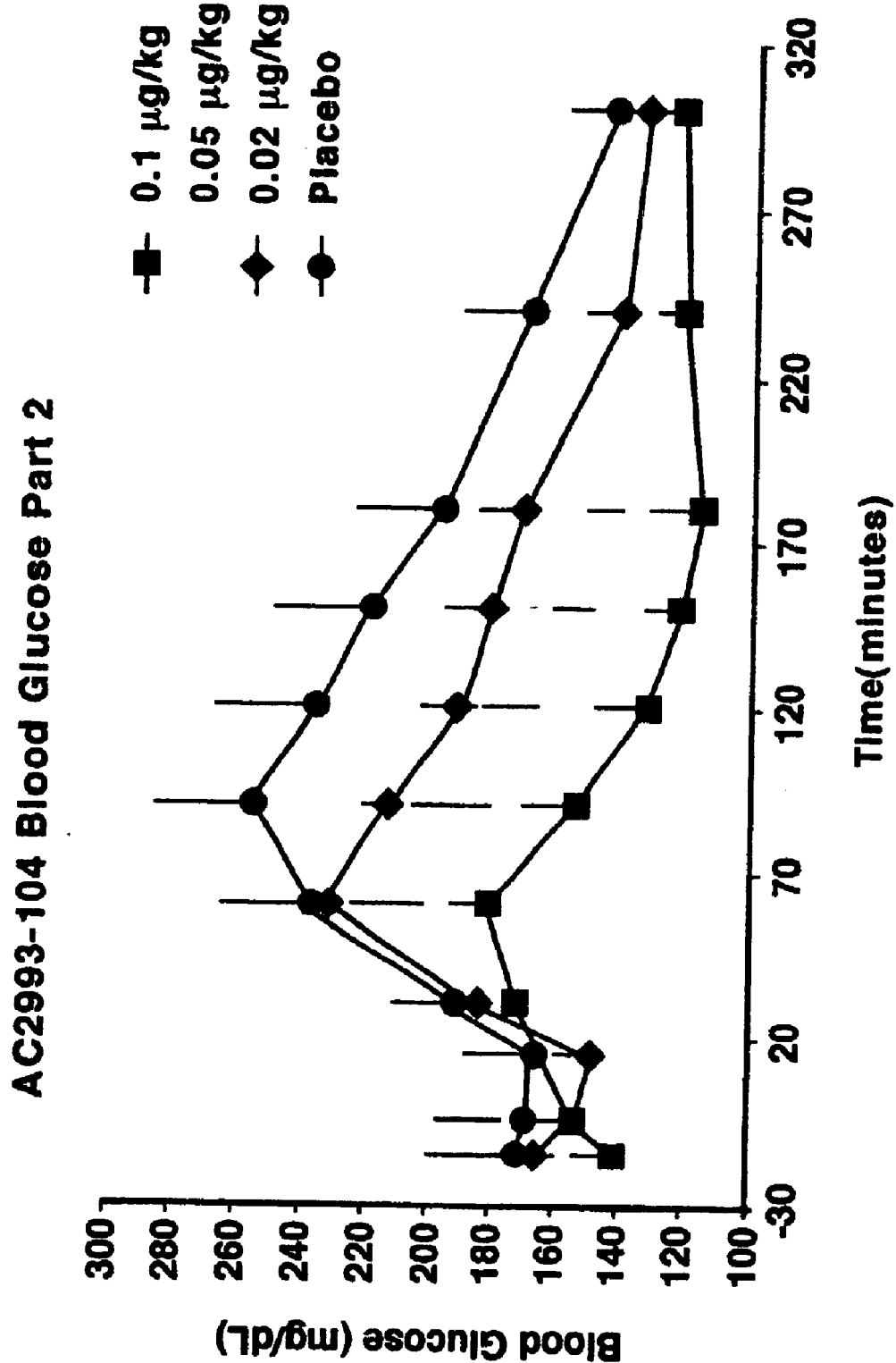
FIGS. 16 and 17 depict glucose-lowering results from the clinical study described in Example 12.
Figure 17:
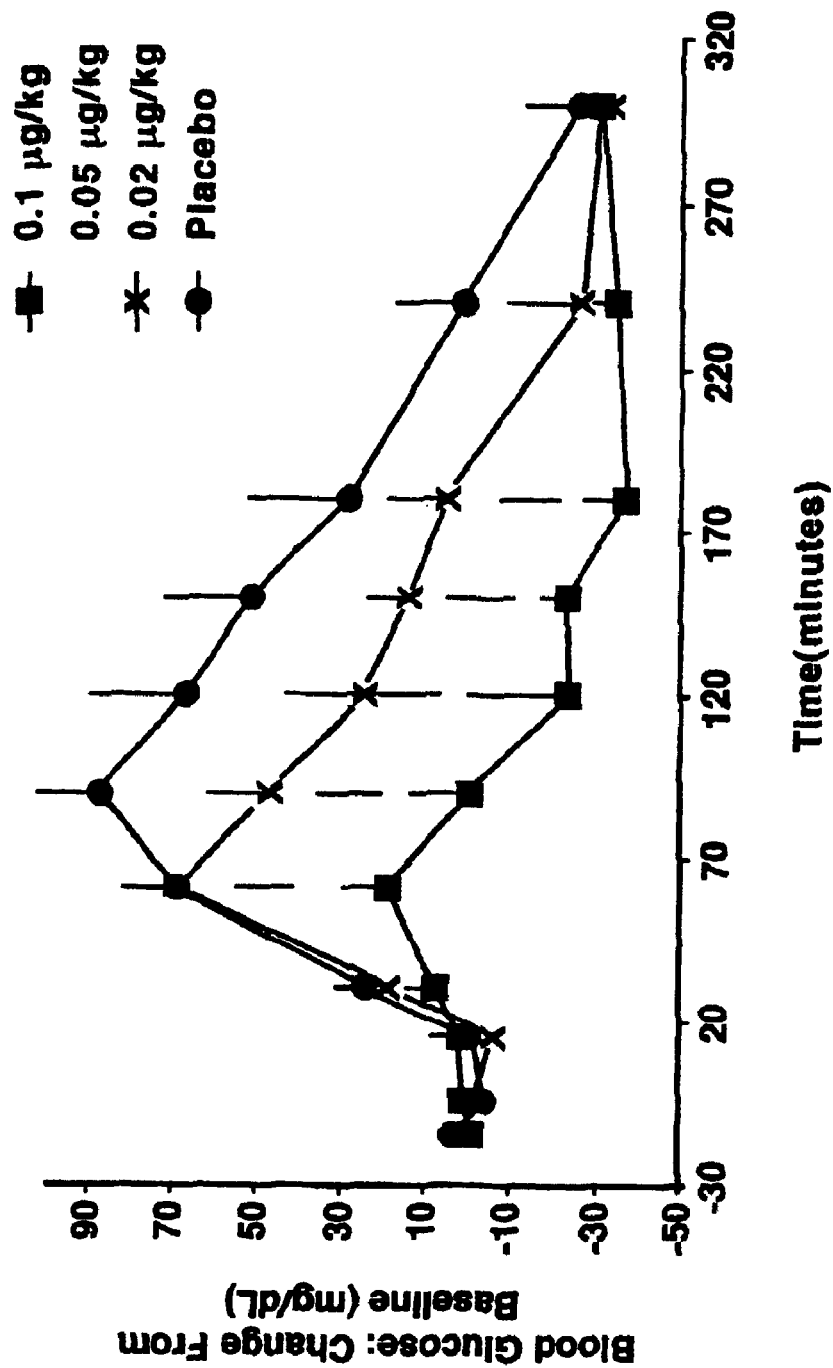

The results of the study are shown in FIGS. 16 and 17. They indicate the ability of various different doses of exendin-4 (0.02 µg/kg, 0.05 µg/kg, and 0.1 µg/kg) to lower blood glucose in people with Type 2 diabetes.

EXAMPLE 13

This Example describes an experiment to determine a dose-response for the insulin-sensitizing effects of exendin-4 and agonists thereof in Diabetic Fatty Zucker rats. The exendin-4 used in these studies was obtained from Bachem (Torrance, Calif.; Cat H8730, Lot 506189), American Peptides (Sunnyvale, Calif.; Cat 301577, Lot K1005ITI) and from in-house solid-phase synthesis (lot AR1374-11; peptide content 93.3%). Thirty nine male Diabetic fatty Zucker rats (ZDF)/Gmi$^{TM}$-(fa/fa) (age 116±20 days; weight 441±39 g) were assigned to 5 treatment groups: saline injections only (n=9), exendin-4 injections 0.1, 1, 10 or 100 µg (n=9, 10, 6, 5, respectively). Of these, 35 rats were used in hyperinsulinemic euglycemic clamp studies (n=9, 7, 9, 5, 5, respectively). Blood was sampled from the tip of the topically-anesthetized tail (Hurricaine brand of 20% topical benzocaine solution, Beutlich, Waukegan, Ill.) of conscious overnight-fasted rats before treatment and at weekly intervals for 5 weeks during treatment for analysis of hemoglobin $A_{1c}$ (DCA2000 latex immuno-agglutination inhibition, Bayer Diagnostics, Tarrytown, N.Y.). Body weight was measured daily.

After 6 weeks of treatment, −16 hours after the last exendin-4 (or saline) dose, and after an overnight fast, hyperinsulinemic euglycemic clamps (DeFronzo R A, Tobin J D, Andres R: Glucose clamp technique: a method for quantifying insulin secretion and resistance. *Amer J Physiol* 237:E214–23, 1979) were performed on halothane-anesthetized rats. Rats were thermoregulated, tracheotomized and catheterized via the saphenous vein for infusion of 20% D-glucose and insulin, and via the femoral artery for blood sampling and blood pressure monitoring (P23XL transducer, Spectramed, Oxnard, Calif.; universal amplifier, Gould, Valley View, Ohio; A/D conversion, DataTranslation, Wilmington, Del.). Insulin (Humulin-R, Eli Lilly, Indianapolis, Ind.) was infused at 50 mU/kg/min, beginning at t=−30 min and continued until t=+180 min. Glucose was infused at a variable rate to maintain euglycemia, determined by glucose sampling and analysis at 5 min intervals. (immobilized glucose oxidase method; YSI 2300-Stat Analyzer, Yellow Springs, Ohio). Mean plasma glucose during clamps was 103.9 mg/dL (mean coefficient of variation was 5.8%). Glucose infusion rate data for analysis were taken from t-60–180 min when responses had approached a steady state. Plasma lactate data, obtained from an immobilized lactate oxidase sensor incorporated in the glucose analyzer, were also collected.

Injections were given intraperitoneally at ~8 a.m. and 4 p.m., Monday through Friday, and at ~10 a.m. on Saturday and Sunday.

Pairwise statistical analyses were performed using Student's t-test routines (Instat v3.0, GraphPad Software, San Diego, Calif.) using $P<0.05$ as the level of significance. Dose-response analyses used 4-parameter logistic regression and general effects were tested using one-way ANOVA (Prism v3.0, GraphPad Software, San Diego, Calif.).

The results showed that in Diabetic Fatty Zucker rats treated with different doses of exendin-4 for 6 weeks, there was a dose-dependent reduction in food intake (ED50 0.14 µg±0.15 log; see FIG. 13*a*), and in body weight (ED50 0.42 µg±0.15 log; see FIG. 13*b*) of up to 27±2 g, representing a 5.6±0.5% decrease in body weight relative to saline-injected controls.

In this group of rats, the diabetic course appeared progressive, since hemoglobin $A_{1c}$ initially rose in all groups. Injection of exendin-4 nonetheless appeared to dose-dependently arrest and reverse the rise in hemoglobin $A_{1c}$ (see FIG. 13*c*). The exendin-4 dose-response for effect on hemoglobin $A_{1c}$ measured during the last 2 weeks of treatment was generally significant (P=0.05 ANOVA) and specifically at 1 μg and 100 g doses (P<0.005, P<0.02 respectively). A similar pattern was observed in relation to fasting plasma triglycerides in the last 2 weeks of treatment, where plasma concentrations were significantly reduced at all doses by between 51% and 65% (P<0.002 ANOVA).

Figure 14A:
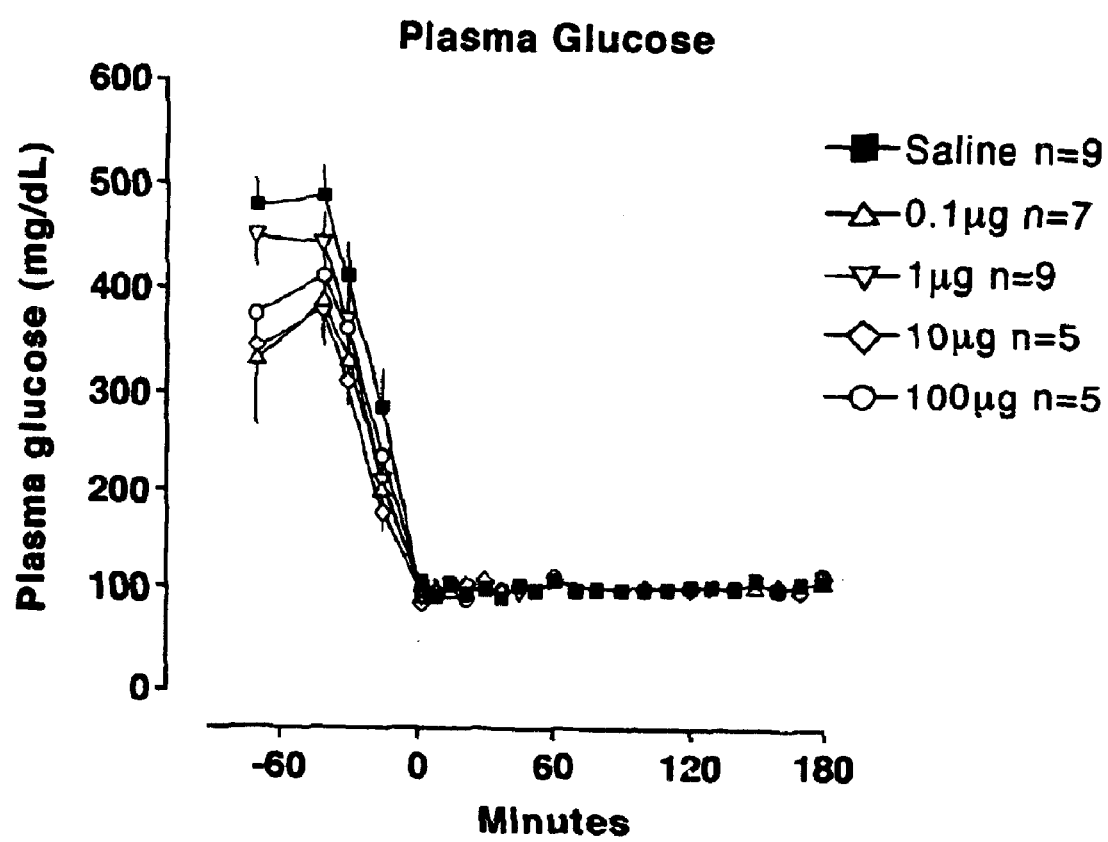
FIG. 14 depicts the plasma glucose concentration (a), glucose infusion rate required to maintain euglycemia (b) and plasma lactate concentration (c) in clamp procedures performed on ZDF rats previously treated for 6 weeks with the specified doses of exendin-4 (i.p. twice daily). Dose-responses for glucose infusion rate and plasma lactate concentration are based upon mean values obtained between 60 and 180 min of the clamp procedure.

Thirty five of the 39 rats entered into the study progressed to an hyperinsulinemic, euglycemic clamp ~16 hours after their last treatment. Initial fasting plasma glucose concentrations, higher in saline-treated (489±28 mg/dL) than exendin-treated rats, fell with insulin infusion and were subsequently clamped at similar plasma glucose concentrations (105.6 mg/dL at 60–180 min; mean coefficient of variation 4.6%; see FIG. 14a). Glucose infusion rate required to maintain euglycemia was dose-dependently increased by prior treatment with exendin-4 (ED50 1.0 μg±0.41 log; see FIG. 14b). Exendin-4 treatment increased glucose infusion rate by up to 48% relative to saline-treated controls.

Plasma lactate concentration before and during the clamp procedure was dose-dependently reduced by prior treatment with exendin-4 (ED50 4 μg±0.25 log; see FIG. 14c). This effect, representing up to a 42% reduction in mean plasma lactate concentration between 60 and 180 minutes of the clamp, appeared primarily due to a reduction in pre-clamp (basal) lactate concentration; increments in plasma lactate during hyperinsulinemia were similar in all treatment groups. There were no treatment-related differences in mean arterial pressure measured before or during clamp procedures.

The approximately 50% increase in insulin sensitivity observed after chronic administration of exendin-4 was both important and surprising in view of observations that exendin-4 has no acute effect in insulin-sensitive tissues in vitro (i.e. no effect on basal or insulin-stimulated incorporation of radiolabeled glucose into glycogen in isolated soleus muscle, or into lipid in isolated adipocytes; Pittner et al., unpublished). Although the possibility that the increase in insulin sensitivity may have resulted in some part from improved glycemic control and reduced glucose toxicity may not be overlooked, it has been reported that the increase in insulin sensitivity from various antidiabetic therapies, including those not classed as insulin sensitizing, is quite variable and it has been reported that acute treatment with GLP-1 appears not to immediately alter insulin sensitivity in humans (Orskov L, Holst J J, Moller J, Orskov C, Moller N, Alberti K G, Schmitz O: GLP-1 does not not acutely affect insulin sensitivity in healthy man. Diabetologia 39:1227–32, 1996; Ahren B, Larsson H, Holst J J: Effects of glucagon-like peptide-1 on islet function and insulin sensitivity in noninsulin-dependent diabetes mellitus. *J Clin Endocrinol Metab* 82:473–8, 1997; UK Prospective Diabetes Study Group: Intensive blood-glucose control with sulphonylureas or insulin compared with conventional treatment and risk of complications in patients with type 2 diabetes (UKPDS 33). *Lancet* 352:837–53, 1998). Thus chronic administration of exendin-4 appears to be associated with increases in insulin sensitivity that are as great as, if not greater than, those observed with other therapies, including insulin sensitizing drugs such as thiazolidinediones and metformin.

EXAMPLE 14

Preparation of Amidated Peptide having SEQ. ID. NO. 9

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. However, at some positions coupling was less efficient than expected and double couplings were required. In particular, residues $Asp_9$, $Thr_7$ and $Phe_6$ all required double coupling. Deprotection (Fmoc group removal) of the growing peptide chain using piperidine was not always efficient. Double deprotection was required at positions $Arg_{20}$, $Val_{19}$ and $Leu_{14}$. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 55%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 60% Solvent B in Solvent A over 30 minutes) of the lyophilized peptide gave product peptide having an observed retention time of 14.5 minutes. Electrospray Mass Spectrometry (M): calculated 4131.7; found 4129.3.

EXAMPLE 15

Preparation of Peptide having SEQ. ID NO. 10

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis were Solvent A (0.1% TFA in water) and Solvent B (0.1% TFA in ACN). Analytical RP-HPLC (gradient 25% to 75% Solvent B in Solvent A over 30 minutes) of the lyophilized peptide gave product peptide having an observed retention time of 21.5 minutes. Electrospray Mass Spectrometry (M): calculated 4168.6; found 4171.2.

EXAMPLE 16

Preparation of Peptide having SEQ ID NO. 11

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis were Solvent A (0.1% TFA in water) and Solvent B (0.1% TFA in ACN). Analytical RP-HPLC (gradient 30% to 60% Solvent B in Solvent A over 30 minutes) of the lyophilized peptide gave product peptide having an observed retention time of 17.9 minutes. Electrospray Mass Spectrometry (M): calculated 4147.6; found 4150.2.

EXAMPLE 17

Preparation of Peptide having SEQ ID NO. 12

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis were Solvent A (0.1% TFA in water) and Solvent B (0.1% TFA in ACN). Analytical RP-HPLC (gradient 35% to 65% Solvent B in Solvent A over 30 minutes) of the lyophilized peptide gave product peptide having an observed retention time of 19.7 minutes. Electrospray Mass Spectrometry (M): calculated 4212.6; found 4213.2.

EXAMPLE 18

Preparation of Peptide having SEQ ID NO. 13

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis were Solvent A (0.1% TFA in water) and Solvent B (0.1% TFA in ACN). Analytical RP-HPLC (gradient 30% to 50% Solvent B in Solvent A over 30 minutes) of the lyophilized peptide gave product peptide having an observed retention time of 16.3 minutes. Electrospray Mass Spectrometry (M): calculated 4262.7; found 4262.4.

EXAMPLE 19

Preparation of Peptide having SEQ ID NO. 14

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6

EXAMPLE 20

Preparation of Peptide having SEQ ID NO. 15

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4224.7.

EXAMPLE 21

Preparation of Peptide having SEQ ID NO. 16

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6

EXAMPLE 22

Preparation of Peptide having SEQ ID NO 17

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4186.6.

EXAMPLE 23

Preparation of Peptide having SEQ ID NO 18

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4200.7.

EXAMPLE 24

Preparation of Peptide having SEQ ID NO 19

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4200.7.

EXAMPLE 25

Preparation of Peptide having SEQ ID NO. 20

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4202.7.

EXAMPLE 26

Preparation of Peptide having SEQ ID NO. 21

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 27

Preparation of Peptide having SEQ ID NO. 22

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4184.6.

EXAMPLE 28

Preparation of Peptide having SEQ ID NO. 23

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 29

Preparation of Peptide having SEQ ID NO. 24

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4224.7.

EXAMPLE 30

Preparation of Peptide having SEQ ID NO. 25

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B. (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 31

Preparation of Peptide having SEQ ID NO. 26

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1 TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4115.5.

EXAMPLE 32

Preparation of Peptide Having SEQ ID NO. 27

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 14188.6.

EXAMPLE 33

Preparation of Peptide having SEQ ID NO. 28

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4131.6.

EXAMPLE 34

Preparation of Peptide having SEQ ID NO. 29

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 35

Preparation of Peptide having SEQ ID NO. 30

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 36

Preparation of Peptide having SEQ ID NO. 31

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Additional double couplings are required at the thioproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4266.8.

EXAMPLE 37

Preparation of Peptide having SEQ ID NO. 32

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Additional double couplings are required at the thioproline positions 38, 37 and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4246.8.

EXAMPLE 38

Preparation of Peptide having SEQ ID NO. 33

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Additional double couplings are required at the homoproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4250.8.

EXAMPLE 39

Preparation of Peptide having SEQ ID NO. 34

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Additional double couplings are required at the homoproline positions 38, 37, and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4234.8.

EXAMPLE 40

Preparation of Peptide having SEQ ID NO. 35

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Additional double couplings are required at the thioproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4209.8.

EXAMPLE 41

Preparation of Peptide having SEQ ID NO. 36

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Additional double couplings are required at the homoproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4193.7.

EXAMPLE 42

Preparation of Peptide having SEQ ID NO. 37

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Additional double couplings are required at the N-methylalanine positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3858.2.

EXAMPLE 43

Preparation of Peptide having SEQ ID NO. 38

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Additional double couplings are required at the N-methylalanine positions 38, 37 and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3940.3.

EXAMPLE 44

Preparation of Peptide having SEQ ID NO. 39

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 14. Additional double couplings are required at the N-methylalanine positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3801.1.

EXAMPLE 45

Preparation of C-Terminal Carboxylic Acid Peptides Corresponding to the Above C-terminal Amide Sequences The above peptides of Examples 1 to 30 are assembled on the so called Wang resin (p-alkoxybenzylalacohol resin (Bachem, 0.54 mmole/g)) using Fmoc-protected amino acids (Applied Biosystems, Inc.), cleaved from the resin, deprotected and purified in a similar way to Example 14. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLE 46

Preparation of Peptide having SEQ ID NO. 7
His Gly Glu Gly Thr Phe Thr Ser Asp Leu Ser Lys Gln Met Glu Glu Glu Ala Val Arg Leu Phe Ile Glu Trp Leu Lys Asn Gly Gly-NH$_2$ [SEQ ID NO. 7]
The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN). The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 50% Solvent B in Solvent A over 30 minutes) of the lyophilized peptide gave product peptide having an observed retention time of 18.9 minutes. Electrospray Mass Spectrometry (M): calculated 3408.0; found 3408.9.

EXAMPLE 47

Preparation of Peptide having SEQ ID NO. 40
His Gly Glu Gly Thr Phe Thr Ser Asp Leu Ser Lys Gln Met Glu Glu Glu Ala Val Arg Leu Phe Ile Glu Trp Leu Lys Asn-NH$_2$ [SEQ ID NO. 40]
The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 30% to 40% Solvent B in Solvent A over 30 minutes) of the lyophilized peptide gave product peptide having an observed retention time of 17.9 minutes. Electrospray Mass Spectrometry (M): calculated 3294.7; found 3294.8.

EXAMPLE 48

Preparation of Peptide having SEQ ID NO. 41
His Gly Glu Gly Thr Phe Thr Ser Asp Leu Ser Lys Gln Leu Glu Glu Glu Ala Val Arg Leu Phe Ile Glu Phe Leu Lys Asn-NH$_2$ [SEQ ID NO. 41]
The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 29% to 36% Solvent B in Solvent A over 30 minutes) of the lyophilized peptide gave product peptide having an observed retention time of 20.7 minutes. Electrospray Mass Spectrometry (M): calculated 3237.6; found 3240.

EXAMPLE 49

Preparation of Peptide having SEQ ID NO. 42
His Ala Glu Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 42]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 15.2 minutes. Electrospray Mass Spectrometry (M): calculated 3251.6; found 3251.5.

EXAMPLE 50

Preparation of Peptide having SEQ ID NO. 43
His Gly Glu Gly Ala Phe Thr Ser Asp Leu Ser Lys Gln Leu Glu Glu Glu Ala Val Arg Leu Phe Ile Glu Phe Leu Lys Asn-NH$_2$ SEQ ID NO. 43]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 13.1 minutes. Electrospray Mass Spectrometry (M): calculated 3207.6; found 3208.3.

EXAMPLE 51

Preparation of Peptide having SEQ ID NO. 44
His Gly Glu Gly Thr Ala Thr Ser Asp Leu Ser Lys Gln Leu Glu Glu Glu Ala Val Arg Leu Phe Ile Glu Phe Leu Lys Asn-NH$_2$ [SEQ ID NO 44]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 12.8 minutes. Electrospray mass Spectrometry (M): calculated 3161.5; found 3163.

EXAMPLE 52

Preparation of Peptide having SEQ ID NO. 45
His Gly Glu Gly Thr Phe Thr Ala Asp Leu Ser Lys Gln Leu Glu Glu Glu Ala Val Arg Leu Phe Ile Glu Phe Leu Lys Asn-NH$_2$ [SEQ ID NO. 45]

The above-identified amidated peptide was assembled on 4-(2-4-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 15.2 minutes. Electrospray Mass Spectrometry (M): calculated 3221.6; found 3222.7.

EXAMPLE 53

Preparation of Peptide having SEQ ID NO. 46
His Gly Glu Gly Thr Phe Thr Ser Asp Ala Ser Lys Gln Leu Glu Glu Glu Ala Val Arg Leu Phe Ile Glu Phe Leu Lys Asn-NH$_2$ [SEQ ID NO. 46]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 34% to 44% Solvent B in Solvent A over 30 minutes) of the lyophilized peptide gave product peptide having an observed retention time of 14.3 minutes. Electrospray Mass Spectrometry (M): calculated 3195.5; found 3199.4.

EXAMPLE 54

Preparation of Peptide having SEQ ID NO. 47
His Gly Glu Gly Thr Phe Thr Ser Asp Leu Ala Lys Gln Leu Glu Glu Glu Ala Val Arg Leu Phe Ile Glu Phe Leu Lys Asn-NH$_2$ [SEQ ID NO. 47]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 15.7 minutes. Electrospray Mass Spectrometry (M): calculated 3221.6; found 3221.6.

EXAMPLE 55

Preparation of Peptide having SEQ ID NO. 48
His Gly Glu Gly Thr Phe Thr Ser Asp Leu Ser Ala Gln Leu Glu Glu Glu Ala Val Arg Leu Phe Ile Glu Phe Leu Lys Asn-NH$_2$ [SEQ ID NO. 48]

The, above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 18.1 minutes. Electrospray Mass Spectrometry (M): calculated 3180.5; found 3180.9.

EXAMPLE 56

Preparation of Peptide having SEQ ID NO. 49

His Gly Glu Gly Thr Phe Thr Ser Asp Leu Ser Lys Ala Leu Glu Glu Glu Ala Val Arg Leu Phe Ile Glu Phe Leu Lys Asn-NH$_2$ [SEQ ID NO. 49]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 17.0 minutes. Electrospray Mass Spectrometry (M): calculated 3180.6; found 3182.8.

EXAMPLE 57

Preparation of Peptide having SEQ ID NO. 50

His Gly Glu Gly Thr Phe Thr Ser Asp Leu Ser Lys Gln Ala Glu Glu Glu Ala Val Arg Leu Phe Ile Glu Phe Leu Lys Asn-NH$_2$ [SEQ ID NO. 50]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 14.9 minutes. Electrospray Mass Spectrometry (M): calculated 3195.5; found 3195.9.

EXAMPLE 58

Preparation of Peptide having SEQ ID NO. 51

His Gly Glu Gly Thr Phe Thr Ser Asp Leu Ser Lys Gln Leu Ala Glu Glu Ala Val Arg Leu Phe Ile Glu Phe Leu Lys Asn-NH$_2$[SEQ ID NO. 51]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 17.9 minutes. Electrospray Mass Spectrometry (M): calculated 3179.6; found 3179.0.

EXAMPLE 59

Preparation of Peptide having SEQ ID NO. 52

His Gly Glu Gly Thr Phe Thr Ser Asp Leu Ser Lys Gln Leu Glu Ala Glu Ala Val Arg Leu Phe Ile Glu Phe Leu Lys Asn-NH$_2$ [SEQ ID NO. 52]

The above-identified amidated peptide was assembled on 4-(2'-4-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 14.3 minutes. Electrospray Mass Spectrometry (M): calculated 3179.6; found 3180.0.

EXAMPLE 60

Preparation of Peptide having SEQ ID NO. 53

His Gly Glu Gly Thr Phe Thr Ser Asp Leu Ser Lys Gln Leu Glu Glu Ala Ala Val Arg Leu Phe Ile Glu Phe Leu Lys Asn-NH$_2$[SEQ ID NO. 53]

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 13.7 minutes. Electrospray Mass Spectrometry (M): calculated 3179.6; found 3179.0.

EXAMPLE 61

Preparation of Peptide having SEQ ID NO. 54

His Gly Glu Gly Thr Phe Thr Ser Asp Leu Ser Lys Gln Leu Glu Glu Ala Ala Arg Leu Phe Ile Glu Phe Leu Lys Asn-NH$_2$ [SEQ ID NO. 54]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 14.0 minutes. Electrospray Mass Spectrometry (M): calculated 3209.6; found 3212.8.

EXAMPLE 62

Preparation of Peptide having SEQ ID NO. 55

His Gly Glu Gly Thr Phe Thr Ser Asp Leu Ser Lys Gln Leu Glu Glu Glu Ala Val Ala Leu Phe Ile Glu Phe Leu Lys Asn-NH$_2$ [SEQ ID NO. 55]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 14.3 minutes. Electrospray Mass Spectrometry (M): calculated 3152.5; found 3153.5.

EXAMPLE 63

Preparation of Peptide having SEQ ID NO. 56

His Gly Glu Gly Thr Phe Thr Ser Asp Leu Ser Lys Gln Leu Glu Glu Glu Ala Val Arg Ala Phe Ile Glu Phe Leu Lys Asn-NH$_2$ [SEQ ID NO. 56]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 12.1 minutes. Electrospray Mass Spectrometry (M): calculated 3195.5; found 3197.7.

EXAMPLE 64

Preparation of Peptide having SEQ ID NO. 57

His Gly Glu Gly Thr Phe Thr Ser Asp Leu Ser Lys Gln Leu Glu Glu Glu Ala Val Arg Leu Phe Ile Ala Phe Leu Lys Asn-NH$_2$ [SEQ ID NO. 57]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 10.9 minutes. Electrospray Mass Spectrometry (M): calculated 3179.6; found 3180.5.

EXAMPLE 65

Preparation of Peptide having SEQ ID NO. 58

His Gly Glu Gly Thr Phe Thr Ser Asp Leu Ser Lys Gln Leu Glu Glu Glu Ala Val Arg Leu Phe Ile Glu Ala Leu Lys Asn-NH$_2$ [SEQ ID NO. 58]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 17.5 minutes. Electrospray Mass Spectrometry (M): calculated 3161.5; found 3163.0.

EXAMPLE 66

Preparation of Peptide having SEQ ID NO. 59

His Gly Glu Gly Thr Phe Thr Ser Asp Leu Ser Lys Gln Leu Glu Glu Glu Ala Val Arg Leu Phe Ile Glu Phe Ala Lys Asn-NH$_2$ [SEQ ID NO. 59]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 19.5 minutes. Electrospray Mass Spectrometry (M): calculated 3195.5; found 3199.

EXAMPLE 67

Preparation of Peptide having SEQ ID NO. 60

His Gly Glu Gly Thr Phe Thr Ser Asp Leu Ser Lys Gln Leu Glu Glu Glu Ala Val Arg Leu Phe Ile Glu Phe Leu Ala Asn-NH$_2$ [SEQ ID NO. 60]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 14.5 minutes. Electrospray Mass Spectrometry (M): calculated 3180.5; found 3183.7.

EXAMPLE 68

Preparation of Peptide having SEQ ID NO. 61

His Gly Glu Gly Thr Phe Thr Ser Asp Leu Ser Lys Gln Leu Glu Glu Glu Ala Val Arg Leu Phe Ile Glu Phe Leu Lys Ala-NH$_2$ [SEQ ID NO. 61]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis were Solvent A (0.1% TFA in water) and Solvent B (0.1% TFA in ACN). Analytical RP-HPLC (gradient 34% to 44% Solvent B in Solvent A over 30 minutes) of the lyophilized peptide gave product peptide having an observed retention time of 22.8 minutes. Electrospray Mass Spectrometry (M): calculated 3194.6; found 3197.6.

EXAMPLE 69

Preparation of Peptide having SEQ ID NO. 62

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro-NH$_2$ [SEQ ID NO. 62]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4099.6.

EXAMPLE 70

Preparation of Peptide having SEQ ID NO. 63

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro-NH$_2$ [SEQ ID NO. 63]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4042.5.

EXAMPLE 71

Preparation of Peptide having SEQ ID NO. 64

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro-NH$_2$ [SEQ ID NO. 64]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4002.4.

EXAMPLE 72

Preparation of Peptide having SEQ ID NO. 65

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro-NH$_2$ [SEQ ID NO. 65]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3945.4.

EXAMPLE 73

Preparation of Peptide having SEQ ID NO, 66

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro-NH$_2$ [SEQ ID NO. 66]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3905.3.

EXAMPLE 74

Preparation of Peptide having SEQ ID NO. 67

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro-NH$_2$ [SEQ ID NO. 67]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3848.2.

EXAMPLE 75

Preparation of Peptide having SEQ ID NO. 68

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ ID NO. 68]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3808.2.

EXAMPLE 76

Preparation of Peptide having SEQ ID NO. 69

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala-NH$_2$ [SEQ ID NO. 69]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3751.1.

EXAMPLE 77

Preparation of Peptide having SEQ ID NO. 70

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly-NH$_2$ [SEQ ID NO. 70]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3737.1.

EXAMPLE 78

Preparation of Peptide having SEQ ID NO. 71

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly-NH$_2$ [SEQ ID NO. 71]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3680.1.

EXAMPLE 79

Preparation of Peptide having SEQ ID NO. 72

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser-NH$_2$ [SEQ ID NO. 72]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3680.1

EXAMPLE 80

Preparation of Peptide having SEQ ID NO. 73

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser-NH$_2$ [SEQ ID NO. 73]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3623.0.

EXAMPLE 81

Preparation of Peptide having SEQ ID NO. 74 His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser-NH$_2$ [SEQ ID NO. 74]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3593.0

EXAMPLE 82

Preparation of Peptide having SEQ ID NO. 75 His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser-NH$_2$ [SEQ ID NO. 75]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3535.9

EXAMPLE 83

Preparation of Peptide having SEQ ID NO. 76 His Gly Glu Gly Thr Phe Thr Ser Asp Leu Ser Lys Gln Met Glu Glu Glu Ala Val Arg Leu Phe Ile Glu Trp Leu Lys Asn Gly Gly Pro-NH$_2$ [SEQ ID NO. 76]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3505.94.

EXAMPLE 84

Preparation of Peptide having SEQ ID NO. 77
His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro-NH$_2$ [SEQ ID NO. 77]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3448.8.

EXAMPLE 85

Preparation of Peptide having SEQ ID NO. 78
His Gly Glu Gly Thr Phe Thr Ser Asp Leu Ser Lys Gln Leu Glu Glu Glu Ala Val Arg Leu Phe Ile Glu Phe Leu Lys Asn Gly Gly-NH$_2$ [SEQ ID NO. 78]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3351.7.

EXAMPLE 86

Preparation of Peptide having SEQ ID NO. 79
His Gly Glu Gly Thr Phe Thr Ser Asp Leu Ser Lys Gln Met Glu Glu Glu Ala Val Arg Leu Phe Ile Glu Trp Leu Lys Asn Gly-NH$_2$ [SEQ ID NO. 79]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3351.8.

EXAMPLE 87

Preparation of Peptide having SEQ ID NO. 80
His Gly Glu Gly Thr Phe Thr Ser Asp Leu Ser Lys Gln Leu Glu Glu Glu Ala Val Arg Leu Phe Ile Glu Phe Leu Lys Asn Gly-NH$_2$ [SEQ ID NO. 80]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3294.7.

EXAMPLE 88

Preparation of Peptide having SEQ ID NO. 81
His Gly Glu Gly Thr Phe Thr Ser Asp Leu Ser Lys Gln Met Glu Glu Glu Ala Val Arg Leu Phe Ile Glu Trp Leu Lys Asn Gly Gly tPro Ser Ser Gly Ala tPro tPro tPro-NH$_2$ [SEQ ID NO. 81]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Double couplings are required at residues 37,36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4197.1.

EXAMPLE 89

Preparation of Peptide having SEQ ID NO. 82
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala tPro tPro tPro-NH$_2$ [SEQ ID NO. 82]

The above-identified amidated peptide is assembled on 14-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4179.1.

EXAMPLE 90

Preparation of Peptide having SEQ ID NO. 83
His Gly Glu Gly Thr Phe Thr Ser Asp Leu Ser Lys Gln Met Glu Glu Glu Ala Val Arg Leu Phe Ile Glu Trp Leu Lys Asn Gly Gly NMeala Ser Ser Gly Ala Pro Pro-NH$_2$ [SEQ ID NO. 83]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide.
Electrospray Mass Spectrometry (M): calculated 3948.3.

EXAMPLE 91

Preparation of Peptide having SEQ ID NO. 84
His Gly Glu Gly Thr Phe Thr Ser Asp Leu Ser Lys Gln Met Glu Glu Glu Ala Val Arg Leu Phe Ile Glu Trp Leu Lys Asn Gly Gly NMeala Ser Ser Gly Ala NMeala Nmeala-NH$_2$ [SEQ ID NO. 84]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3840.1.

EXAMPLE 92

Preparation of Peptide having SEQ ID NO. 85
His Gly Glu Gly Thr Phe Thr Ser Asp Leu Ser Lys Gln Met Glu Glu Glu Ala Val Arg Leu Phe Ile Glu Trp Leu Lys Asn Gly Gly hPro Ser Ser Gly Ala hPro hPro-NH$_2$ [SEQ ID NO. 85]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4050.1.

EXAMPLE 93

Preparation of Peptide having SEQ ID NO. 86
His Gly Glu Gly Thr Phe Thr Ser Asp Leu Ser Lys Gln Met Glu Glu Glu Ala Val Arg Leu Phe Ile Glu Trp Leu Lys Asn Gly Gly hPro Ser Ser Gly Ala hPro-NH$_2$ [SEQ ID NO. 86]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. A double coupling is required at residue 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3937.1.

EXAMPLE 94

Preparation of Peptide having SEQ ID NO. 87
Arg Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ ID NO. 87]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3827.2.

EXAMPLE 95

Preparation of Peptide having SEQ ID NO. 88
His Gly Asp Gly Thr Phe Thr Ser Asp Leu Ser Lys Gln Met Glu Glu Glu Ala Val Arg Leu Phe Ile Glu Trp Leu Lys Asn Gly Gly-NH$_2$ [SEQ ID NO. 88]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3394.8.

EXAMPLE 96

Preparation of Peptide having SEQ ID NO. 89
His Gly Glu Gly Thr Naphthylala Thr Ser Asp Leu Ser Lys Gln Leu Glu Glu Glu Ala Val Arg Leu Phe Ile Glu Phe Leu Lys Asn-NH$_2$ [SEQ ID NO. 89]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3289.5.

EXAMPLE 97

Preparation of Peptide having SEQ ID NO. 90
His Gly Glu Gly Thr Phe Ser Ser Asp Leu Ser Lys Gln Met Glu Glu Glu Ala Val Arg Leu Phe Ile Glu Trp Leu Lys Asn-NH$_2$ [SEQ ID NO. 90]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3280.7.

EXAMPLE 98

Preparation of Peptide having SEQ ID NO. 91
His Gly Glu Gly Thr Phe Ser Thr Asp Leu Ser Lys Gln Met Glu Glu Glu Ala Val Arg Leu Phe Ile Glu Trp Leu Lys Asn-NH$_2$ [SEQ ID NO. 91]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3294.7.

EXAMPLE 99

Preparation of Peptide having SEQ ID NO. 92
His Gly Glu Gly Thr Phe Thr Ser Glu Leu Ser Lys Gln Met Ala Glu Glu Ala Val Arg Leu Phe Ile Glu Trp Leu Lys Asn-NH$_2$ [SEQ ID NO. 92]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3250.7.

EXAMPLE 100

Preparation of Peptide having SEQ ID NO. 93
His Gly Glu Gly Thr Phe Thr Ser Asp pentylgly Ser Lys Gln Leu Glu Glu Glu Ala Val Arg Leu Phe Ile Glu Phe Leu Lys Asn-NH$_2$ [SEQ ID NO. 93]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3253.5.

EXAMPLE 101

Preparation of Peptide having SEQ ID NO. 94
His Gly Glu Gly Thr Phe Thr Ser Asp Leu Ser Lys Gln Leu Glu Glu Glu Ala Val Arg Leu Naphthylala Ile Glu Phe Leu Lys Asn-NH$_2$ [SEQ ID NO. 94]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3289.5.

EXAMPLE 102

Preparation of Peptide having SEQ ID NO. 95
His Gly Glu Gly Thr Phe Thr Ser Asp Leu Ser Lys Gln Met Glu Glu Glu Ala Val Arg Leu Phe tButylgly Glu Trp Leu Lys Asn-NH$_2$ [SEQ ID NO. 95]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3183.4.

EXAMPLE 103

Preparation of Peptide having SEQ ID NO. 96
His Gly Glu Gly Thr Phe Thr Ser Asp Leu Ser Lys Gln Leu Glu Glu Glu Ala Val Arg Leu Phe Ile Asp Phe Leu Lys Asn-NH$_2$ [SEQ ID NO. 96]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3237.6.

EXAMPLE 104

Preparation of Peptide having SEQ ID NO. 97
His Gly Glu Gly Thr Phe Thr Ser Asp Ala Ser Lys Gln Leu Glu Glu Glu Ala Val Arg Leu Phe Ile Glu Phe Leu Lys Asn Gly Gly Pro Ser Ser-NH$_2$ [SEQ ID NO. 97]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3637.9.

EXAMPLE 105

Preparation of Peptide having SEQ ID NO. 98
His Gly Glu Gly Thr Phe Thr Ser Asp Ala Ser Lys Gln Met Glu Glu Glu Ala Val Arg Leu Phe Ile Glu Trp Leu Lys Asn Gly-NH₂ [SEQ. ID NO. 98]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3309.7.

EXAMPLE 106

Preparation of Peptide having SEQ ID NO. 99
His Gly Glu Gly Thr Phe Thr Ser Asp Ala Ser Lys Gln Met Glu Glu Glu Ala Val Arg Leu Phe Ile Glu Trp Leu Lys Asn Gly Gly hPro Ser Ser Gly Ala hPro hPro-NH₂ [SEQ ID NO. 99]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 46. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3711.1.

EXAMPLE 107

Preparation of C-Terminal Carboxylic Acid Peptides Corresponding to the Above C-Terminal Amide Sequences for SEQ ID NOS. 7, 40–61, 68–75, 78–80 and 87–98

Peptides having the sequences of SEQ ID NOS. 7, 40–61, 68–75, 78–80 and 87–98 are assembled on the so called Wang resin (p-alkoxybenzylalacohol resin (Bachem, 0.54 mmole/g)) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLE 108

Preparation of C-Terminal Carboxylic Acid Peptides Corresponding to the Above C-Terminal Amide Sequences for SEQ ID NOS. 62–67, 76, 77, 81–86 and 99

Peptides having the sequences of SEQ ID NOS. 62–67, 76, 77, 81–86 and 99 are assembled on the 2-chlorotritylchloride resin (200–400 mesh), 2% DVB (Novabiochem, 0.4–1.0 mmole/g)) using Fmoc-protected amino acids (Applied Biosystems, Inc.), cleaved from the resin, deprotected and purified in a similar way to Example 46. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLE 109

Preparation of Peptide having SEQ ID NO. 100
Ala Gly Glu Gly Thr Phe Thr Ser Asp Leu Ser Lys Gln Leu Glu Glu Glu Ala Val Arg Leu Phe Ile Glu Phe Leu Lys Asn-NH₂ [SEQ ID NO. 100]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 60% Solvent B in Solvent A over 30 minutes) of the lyophilized peptide gave product peptide having an observed retention time of 19.2 minutes. Electrospray Mass Spectrometry (M): calculated 3171.6; found 3172.

EXAMPLE 110

Preparation of Peptide having SEQ ID NO. 101
His Gly Ala Gly Thr Phe Thr Ser Asp Leu Ser Lys Gln Leu Glu Glu Glu Ala Val Arg Leu Phe Ile Glu Phe Leu Lys Asn-NH₂ [SEQ ID NO. 101]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 14.9 minutes. Electrospray Mass Spectrometry (M): calculated 3179.6; found 3180.

EXAMPLE 111

Preparation of Peptide having SEQ ID NO. 102

His Gly Glu Ala Thr Phe Thr Ser Asp Leu Ser Lys Gln Leu Glu Glu Glu Ala Val Arg Leu Phe Ile Glu Phe Leu Lys Asn-NH$_2$ [SEQ. ID NO. 102]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 12.2 minutes. Electrospray Mass Spectrometry (M): calculated 3251.6; found 3253.3.

EXAMPLE 112

Preparation of Peptide having SEQ ID NO. 103

His Gly Glu Gly Thr Phe Thr Ser Ala Leu Ser Lys Gln Leu Glu Glu Glu Ala Val Arg Leu Phe Ile Glu Phe Leu Lys Asn-NH$_2$ [SEQ ID NO 103]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 16.3 minutes. Electrospray Mass Spectrometry (M): calculated 3193.6; found 3197.

EXAMPLE 113

Preparation of Peptide having SEQ ID NO. 104

Ala Gly Glu Gly Thr Phe Thr Ser Asp Leu Ser Lys Gln Met Glu Glu Glu Ala Val Arg Leu Phe Ile Glu Trp Leu Lys Asn-NH$_2$ [SEQ ID NO. 104]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3228.6.

EXAMPLE 114

Preparation of Peptide having SEQ ID NO. 105

His Gly Ala Gly Thr Phe Thr Ser Asp Leu Ser Lys Gln Met Glu Glu Glu Ala Val Arg Leu Phe Ile Glu Trp Leu Lys Asn-NH$_2$ [SEQ ID NO. 105]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3234.7.

EXAMPLE 115

Preparation of Peptide having SEQ ID NO. 106

His Gly Glu Ala Thr Phe Thr Ser Asp Leu Ser Lys Gln Met Glu Glu Glu Ala Val Arg Leu Phe Ile Glu Trp Leu Lys Asn-NH$_2$ [SEQ ID NO. 106]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3308.7.

EXAMPLE 116

Preparation of Peptide having SEQ ID NO. 107

His Gly Glu Gly Thr Phe Thr Ser Ala Leu Ser Lys Gln Met Glu Glu Glu Ala Val Arg Leu Phe Ile Glu Trp Leu Lys Asn-NH$_2$ [SEQ ID NO. 107]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3250.7

EXAMPLE 117

Preparation of Peptide having SEQ ID NO. 108

His Gly Glu Gly Thr Phe Thr Ser Asp Ala Ser Lys Gln Met Glu Glu Glu Ala Val Arg Leu Phe Ile Glu Trp Leu Lys Asn-NH$_2$ [SEQ ID NO. 108]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3252.6.

EXAMPLE 118

Preparation of Peptide having SEQ ID NO. 109

Ala Ala Glu Gly Thr Phe Thr Ser Asp Leu Ser Lys Gln Met Glu Glu Glu Ala Val Arg Leu Phe Ile Glu Trp Leu Lys Asn-NH$_2$ [SEQ ID NO. 109]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 119

Preparation of Peptide having SEQ ID NO. 110

Ala Ala Glu Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID NO. 110]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 120

Preparation of Peptide having SEQ ID NO. 111

Ala Gly Asp Gly Thr Phe Thr Ser Asp Leu Ser Lys Gln Met Glu Glu Glu Ala Val Arg Leu Phe Ile Glu Trp Leu Lys Asn-NH$_2$ [SEQ ID. NO. 111]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3214.6.

EXAMPLE 121

Preparation of Peptide having SEQ ID NO. 112

Ala Gly Asp Gly Thr Phe Thr Ser Asp Leu Ser Lys Gln Leu Glu Glu Glu Ala Val Arg Leu Phe Ile Glu Phe Leu Lys Asn-NH$_2$ [SEQ ID NO. 112]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.5.

EXAMPLE 122

Preparation of Peptide having SEQ ID NO. 113

Ala Gly Asp Gly Ala Phe Thr Ser Asp Leu Ser Lys Gln Met Glu Glu Glu Ala Val Arg Leu Phe Ile Glu Trp Leu Lys Asn-NH$_2$ [SEQ ID NO. 113]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3184.6.

EXAMPLE 123

Preparation of Peptide having SEQ ID NO. 114

Ala Gly Asp Gly Ala Phe Thr Ser Asp Leu Ser Lys Gln Leu Glu Glu Glu Ala Val Arg Leu Phe Ile Glu Phe Leu Lys Asn-NH$_2$ [SEQ ID NO. 114]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3127.5.

EXAMPLE 124

Preparation of Peptide having SEQ ID NO. 115

Ala Gly Asp Gly Thr NaphthylAla Thr Ser Asp Leu Ser Lys Gln Met Glu Glu Glu Ala Val Arg Leu Phe Ile Glu Trp Leu Lys Asn-NH$_2$ [SEQ ID NO. 115]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3266.4.

EXAMPLE 125

Preparation of Peptide having SEQ ID NO. 116

Ala Gly Asp Gly Thr Naphthylala Thr Ser Asp Leu Ser Lys Gln Leu Glu Glu Glu Ala Val Arg Leu Phe Ile Glu Phe Leu Lys Asn-NH$_2$ [SEQ ID NO. 116]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3209.4.

EXAMPLE 126

Preparation of Peptide having SEQ ID NO. 117

Ala Gly Asp Gly Thr Phe Ser Ser Asp Leu Ser Lys Gln Met Glu Glu Glu Ala Val Arg Leu Phe Ile Glu Trp Leu Lys Asn-NH$_2$ [SEQ ID NO. 117]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 127

Preparation of Peptide having SEQ ID NO. 118

Ala Gly Asp Gly Thr Phe Ser Ser Asp Leu Ser Lys Gln Leu Glu Glu Glu Ala Val Arg Leu Phe Ile Glu Phe Leu Lys Asn-NH$_2$ [SEQ ID NO. 118]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 128

Preparation of Peptide having SEQ ID NO. 119

Ala Gly Asp Gly Thr Phe Thr Ala Asp Leu Ser Lys Gln Met Glu Glu Glu Ala Val Arg Leu Phe Ile Glu Trp Leu Lys Asn-NH$_2$ [SEQ ID NO. 119]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3198.6.

EXAMPLE 129

Preparation of Peptide having SEQ ID NO. 120

Ala Gly Asp Gly Thr Phe Thr Ala Asp Leu Ser Lys Gln Leu Glu Glu Glu Ala Val Arg Leu Phe Ile Glu Phe Leu Lys Asn-NH$_2$ [SEQ ID NO. 120]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3141.5.

EXAMPLE 130

Preparation of Peptide having SEQ ID NO. 121

Ala Gly Asp Gly Thr Phe Thr Ser Ala Leu Ser Lys Gln Met Glu Glu Glu Ala Val Arg Leu Phe Ile Glu Trp Leu Lys Asn-NH$_2$ [SEQ ID NO. 121]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3170.6.

EXAMPLE 131

Preparation of Peptide having SEQ ID NO. 131

Ala Gly Asp Gly Thr Phe Thr Ser Ala Leu Ser Lys Gln Leu Glu Glu Glu Ala Val Arg Leu Phe Ile Glu Phe Leu Lys Asn-NH$_2$ [SEQ ID NO. 122]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3113.5.

EXAMPLE 132

Preparation of Peptide having SEQ ID NO. 123

Ala Gly Asp Gly Thr Phe Thr Ser Glu Leu Ser Lys Gln Met Glu Glu Glu Ala Val Arg Leu Phe Ile Glu Trp Leu Lys Asn-NH$_2$ [SEQ ID NO. 123]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3228.6.

EXAMPLE 133

Preparation of Peptide having SEQ ID NO. 124

Ala Gly Asp Gly Thr Phe Thr Ser Glu Leu Ser Lys Gln Leu Glu Glu Glu Ala Val Arg Leu Phe Ile Glu Phe Leu Lys Asn-NH$_2$ [SEQ ID NO. 124]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3171.6.

EXAMPLE 134

Preparation of Peptide having SEQ ID NO. 125

Ala Gly Asp Gly Thr Phe Thr Ser Asp Ala Ser Lys Gln Met Glu Glu Glu Ala Val Arg Leu Phe Ile Glu Trp Leu Lys Asn-NH$_2$ [SEQ ID NO. 125]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3172.5.

EXAMPLE 135

Preparation of Peptide having SEQ ID NO. 126

Ala Gly Asp Gly Thr Phe Thr Ser Asp Ala Ser Lys Gln Leu Glu Glu Glu Ala Val Arg Leu Phe Ile Glu Phe Leu Lys Asn-NH$_2$ [SEQ ID NO. 126]

The above-identified amidated peptiden is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.4.

EXAMPLE 136

Preparation of Peptide having SEQ ID NO. 127

Ala Gly Asp Gly Thr Phe Thr Ser Asp Pentylgly Ser Lys Gln Met Glu Glu Glu Ala Val Arg Leu Phe Ile Glu Trp Leu Lys Asn-NH$_2$ [SEQ ID NO. 127]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3230.4.

EXAMPLE 137

Preparation of Peptide having SEQ ID NO. 128

Ala Gly Asp Gly Thr Phe Thr Ser Asp Pentylgly Ser Lys Gln Leu Glu Glu Glu Ala Val Arg Leu Phe Ile Glu Phe Leu Lys Asn-NH$_2$ [SEQ ID NO. 128]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1-% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3198.6.

EXAMPLE 138

Preparation of Peptide having SEQ ID NO. 129

Ala Gly Asp Gly Thr Phe Thr Ser Asp Leu Ala Lys Gln Met Glu Glu Glu Ala Val Arg Leu Phe Ile Glu Trp Leu Lys Asn-NH$_2$ [SEQ ID NO. 129]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3141.5.

EXAMPLE 139

Preparation of Peptide having SEQ ID NO. 130

Ala Gly Asp Gly Thr Phe Thr Ser Asp Leu Ala Lys Gln Leu Glu Glu Glu Ala Val Arg Leu Phe Ile Glu Phe Leu Lys Asn-NH$_2$ [SEQ ID NO. 130]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.5.

EXAMPLE 140

Preparation of Peptide having SEQ ID NO. 131

Ala Gly Asp Gly Thr Phe Thr Ser Asp Leu Ser Ala Gln Met Glu Glu Glu Ala Val Arg Leu Phe Ile Glu Trp Leu Lys Asn-NH$_2$ [SEQ ID NO. 131]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.4.

EXAMPLE 141

Preparation of Peptide having SEQ ID NO. 132

Ala Gly Asp Gly Thr Phe Thr Ser Asp Leu Ser Ala Gln Leu Glu Glu Glu Ala Val Arg Leu Phe Ile Glu Phe Leu Lys Asn-NH$_2$ [SEQ ID NO. 132]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.6.

EXAMPLE 142

Preparation of Peptide having SEQ ID NO. 133

Ala Gly Asp Gly Thr Phe Thr Ser Asp Leu Ser Lys Ala Met Glu Glu Glu Ala Val Arg Leu Phe Ile Glu Trp Leu Lys Asn-NH$_2$ [SEQ ID NO. 133]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.5.

EXAMPLE 143

Preparation of Peptide having SEQ ID NO. 134

Ala Gly Asp Gly Thr Phe Thr Ser Asp Leu Ser Lys Ala Leu Glu Glu Glu Ala Val Arg Leu Phe Ile Glu Phe Leu Lys Asn-NH$_2$ [SEQ ID NO. 134]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.5.

EXAMPLE 144

Preparation of Peptide having SEQ ID NO. 135

Ala Gly Asp Gly Thr Phe Thr Ser Asp Leu Ser Lys Gln Ala Glu Glu Glu Ala Val Arg Leu Phe Ile Glu Trp Leu Lys Asn-NH$_2$ [SEQ ID NO. 135]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3154.5.

EXAMPLE 145

Preparation of Peptide having SEQ ID NO. 136

Ala Gly Asp Gly Thr Phe Thr Ser Asp Leu Ser Lys Gln Ala Glu Glu Glu Ala Val Arg Leu Phe Ile Glu Phe Leu Lys Asn-NH$_2$ [SEQ ID NO. 136]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.5.

EXAMPLE 146

Preparation of Peptide having SEQ ID NO. 137
Ala Gly Asp Gly Thr Phe Thr Ser Asp Leu Ser Lys Gln Pentylgly Glu Glu Glu Ala Val Arg Leu Phe Ile Glu Trp Leu Lys Asn-NH$_2$ [SEQ ID NO. 137]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3212.4.

EXAMPLE 147

Preparation of Peptide having SEQ ID NO. 138
Ala Gly Asp Gly Thr Phe Thr Ser Asp Leu Ser Lys Gln Pentylgly Glu Glu Glu Ala Val Arg Leu Phe Ile Glu Phe Leu Lys Asn-NH$_2$ [SEQ ID NO. 138]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3173.4.

EXAMPLE 148

Preparation of Peptide having SEQ ID NO. 139
Ala Gly Asp Gly Thr Phe Thr Ser Asp Leu Ser Lys Gln Met Ala Glu Glu Ala Val Arg Leu Phe Ile Glu Trp Leu Lys Asn-NH$_2$ [SEQ ID NO. 139]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3156.6.

EXAMPLE 149

Preparation of Peptide having SEQ ID NO. 140
Ala Gly Asp Gly Thr Phe Thr Ser Asp Leu Ser Lys Gln Leu Ala Glu Glu Ala Val Arg Leu Phe Ile Glu Phe Leu Lys Asn-NH$_2$ [SEQ. ID NO. 140]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 150

Preparation of Peptide having SEQ ID NO. 141
Ala Gly Asp Gly Thr Phe Thr Ser Asp Leu Ser Lys Gln Met Glu Ala Glu Ala Val Arg Leu Phe Ile Glu Trp Leu Lys Asn-NH$_2$ [SEQ ID NO. 141]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3156.6.

EXAMPLE 151

Preparation of Peptide having SEQ ID NO. 142
Ala Gly Asp Gly Thr Phe Thr Ser Asp Leu Ser Lys Gln Leu Glu Ala Glu Ala Val Arg Leu Phe Ile Glu Phe Leu Lys Asn-NH$_2$ [SEQ ID NO. 142]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 152

Preparation of Peptide having SEQ ID NO. 143
Ala Gly Asp Gly Thr Phe Thr Ser Asp Leu Ser Lys Gln Met Glu Glu Ala Ala Val Arg Leu Phe Ile Glu Trp Leu Lys Asn-NH$_2$ [SEQ ID NO. 143]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3156.6.

EXAMPLE 153

Preparation of Peptide having SEQ ID NO. 144
Ala Gly Asp Gly Thr Phe Thr Ser Asp Leu Ser Lys Gln Leu Glu Glu Ala Ala Val Arg Leu Phe Ile Glu Phe Leu Lys Asn-NH$_2$ [SEQ ID NO. 144]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 154

Preparation of Peptide having SEQ ID NO. 145
Ala Gly Asp Gly Thr Phe Thr Ser Asp Leu Ser Lys Gln Met Glu Glu Glu Ala Ala Arg Leu Phe Ile Glu Trp Leu Lys Asn-NH$_2$ [SEQ ID NO. 145]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3186.6.

EXAMPLE 155

Preparation of Peptide having SEQ ID NO. 146
Ala Gly Asp Gly Thr Phe Thr Ser Asp Leu Ser Lys Gln Leu Glu Glu Glu Ala Ala Arg Leu Phe Ile Glu Phe Leu Lys Asn-NH$_2$ [SEQ ID NO. 146]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3129.5.

EXAMPLE 156

Preparation of Peptide having SEQ ID NO. 147
Ala Gly Asp Gly Thr Phe Thr Ser Asp Leu Ser Lys Gln Met Glu Glu Glu Ala Val Ala Leu Phe Ile Glu Trp Leu Lys Asn-NH$_2$ [SEQ ID NO. 147]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3129.5.

EXAMPLE 157

Preparation of Peptide having SEQ ID NO. 148
Ala Gly Asp Gly Thr Phe Thr Ser Asp Leu Ser Lys Gln Leu Glu Glu Glu Ala Val Ala Leu Phe Ile Glu Phe Leu Lys Asn-NH$_2$ [SEQ ID NO. 148]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3072.4.

EXAMPLE 158

Preparation of Peptide having SEQ ID NO. 149
Ala Gly Asp Gly Thr Phe Thr Ser Asp Leu Ser Lys Gln Met Glu Glu Glu Ala Val Arg Ala Phe Ile Glu Trp Leu Lys Asn-NH$_2$ [SEQ ID NO. 149]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3172.5.

EXAMPLE 159

Preparation of Peptide having SEQ ID NO. 150
Ala Gly Asp Gly Thr Phe Thr Ser Asp Leu Ser Lys Gln Leu Glu Glu Glu Ala Val Arg Ala Phe Ile Glu Phe Leu Lys Asn-NH$_2$ [SEQ ID NO. 150]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.5.

EXAMPLE 160

Preparation of Peptide having SEQ ID NO. 151
Ala Gly Asp Gly Thr Phe Thr Ser Asp Leu Ser Lys Gln Met Glu Glu Glu Ala Val Arg Leu Naphthylala Ile Glu Trp Leu Lys Asn-NH$_2$ [SEQ ID NO. 151]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3266.4.

EXAMPLE 161

Preparation of Peptide having SEQ ID NO. 152
Ala Gly Asp Gly Thr Phe Thr Ser Asp Leu Ser Lys Gln Leu Glu Glu Glu Ala Val Arg Leu Naphthylala Ile Glu Phe Leu Lys Asn-NH$_2$ [SEQ ID NO. 152]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3209.4.

EXAMPLE 162

Preparation of Peptide having SEQ ID NO. 153
Ala Gly Asp Gly Thr Phe Thr Ser Asp Leu Ser Lys Gln Met Glu Glu Glu Ala Val Arg Leu Phe Val Glu Trp Leu Lys Asn-NH$_2$ [SEQ ID NO. 153]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 163

Preparation of Peptide having SEQ ID NO. 154
Ala Gly Asp Gly Thr Phe Thr Ser Asp Leu Ser Lys Gln Leu Glu Glu Glu Ala Val Arg Leu Phe Val Glu Phe Leu Lys Asn-NH$_2$ [SEQ ID NO. 154]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 164

Preparation of Peptide having SEQ ID NO. 155
Ala Gly Asp Gly Thr Phe Thr Ser Asp Leu Ser Lys Gln Met Glu Glu Glu Ala Val Arg Leu Phe tButylgly Glu Trp Leu Lys Asn-NH$_2$ [SEQ ID NO. 155]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3216.5.

EXAMPLE 165

Preparation of Peptide having SEQ ID NO. 156
Ala Gly Asp Gly Thr Phe Thr Ser Asp Leu Ser Lys Gln Leu Glu Glu Glu Ala Val Arg Leu Phe tButylgly Glu Phe Leu Lys Asn-NH$_2$ [SEQ ID NO. 156]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3159.4.

EXAMPLE 166

Preparation of Peptide having SEQ ID NO. 157
Ala Gly Asp Gly Thr Phe Thr Ser Asp Leu Ser Lys Gln Met Glu Glu Glu Ala Val Arg Leu Phe Ile Asp Trp Leu Lys Asn-NH$_2$ [SEQ ID NO. 157]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 167

Preparation of Peptide having SEQ ID NO. 158

Ala Gly Asp Gly Thr Phe Thr Ser Asp Leu Ser Lys Gln Leu Glu Glu Glu Ala Val Arg Leu Phe Ile Asp Phe Leu Lys Asn-NH$_2$ [SEQ ID NO. 158]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 168

Preparation of Peptide having SEQ ID NO. 159

Ala Gly Asp Gly Thr Phe Thr Ser Asp Leu Ser Lys Gln Met Glu Glu Glu Ala Val Arg Leu Phe Ile Glu Ala Leu Lys Asn-NH$_2$ [SEQ ID NO. 159]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 169

Preparation of Peptide having SEQ ID NO. 160

Ala Gly Asp Gly Thr Phe Thr Ser Asp Leu Ser Lys Gln Leu Glu Glu Glu Ala Val Arg Leu Phe Ile Glu Ala Leu Lys Asn-NH$_2$ [SEQ ID NO. 160]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3081.4.

EXAMPLE 170

Preparation of Peptide having SEQ ID NO. 161

Ala Gly Asp Gly Thr Phe Thr Ser Asp Leu Ser Lys Gln Met Glu Glu Glu Ala Val Arg Leu Phe Ile Glu Trp Ala Lys Asn-NH$_2$ [SEQ ID NO. 161]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3172.5.

EXAMPLE 171

Preparation of Peptide having SEQ ID NO. 162

Ala Gly Asp Gly Thr Phe Thr Ser Asp Leu Ser Lys Gln Leu Glu Glu Glu Ala Val Arg Leu Phe Ile Glu Phe Ala Lys Asn-NH$_2$ [SEQ ID NO. 162]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.5.

EXAMPLE 172

Preparation of Peptide having SEQ ID NO. 163

Ala Gly Asp Gly Thr Phe Thr Ser Asp Leu Ser Lys Gln Met Glu Glu Glu Ala Val Arg Leu Phe Ile Glu Trp Leu Ala Asn-NH$_2$ [SEQ ID NO. 163]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.5.

EXAMPLE 173

Preparation of Peptide having SEQ ID NO. 164

Ala Gly Asp Gly Thr Phe Thr Ser Asp Leu Ser Lys Gln Leu Glu Glu Glu Ala Val Arg Leu Phe Ile Glu Phe Leu Ala Asn-NH$_2$ [SEQ ID NO. 164]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.4.

EXAMPLE 174

Preparation of Peptide having SEQ ID NO. 165
Ala Gly Asp Gly Thr Phe Thr Ser Asp Leu Ser Lys Gln Met Glu Glu Glu Ala Val Arg Leu Phe Ile Glu Trp Leu Lys Ala-NH$_2$ [SEQ ID NO. 165]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3171.6.

EXAMPLE 175

Preparation of Peptide having SEQ ID NO. 166
Ala Gly Asp Gly Thr Phe Thr Ser Asp Leu Ser Lys Gln Leu Glu Glu Glu Ala Val Arg Leu Phe Ile Glu Phe Leu Lys Ala-NH$_2$ [SEQ ID NO. 166]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3114.5.

EXAMPLE 176

Preparation of Peptide having SEQ ID NO. 167
Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro-NH$_2$ [SEQ ID NO. 167]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4033.5.

EXAMPLE 177

Preparation of Peptide having SEQ ID NO. 168
His Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro-NH$_2$ [SEQ ID NO. 168]

The above-identified amidated peptide is assembled on 4-(2'-4-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3984.4.

EXAMPLE 178

Preparation of Peptide having SEQ ID NO. 169
His Gly Glu Ala Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro-NH$_2$ [SEQ ID NO. 169]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4016.5.

EXAMPLE 179

Preparation of Peptide having SEQ ID NO. 170
His Gly Glu Gly Thr Phe Thr Ser Ala Leu Ser Lys Gln Met Glu Glu Glu Ala Val Arg Leu Phe Ile Glu Trp Leu Lys Asn Gly Gly Pro Ser Ser Gly Ala Pro-NH$_2$ [SEQ ID NO. 170]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3861.3.

EXAMPLE 180

Preparation of Peptide having SEQ ID NO. 171
Ala Gly Glu Gly Thr Phe Thr Ser Asp Ala Ser Lys Gln Leu Glu Glu Glu Ala Val Arg Leu Phe Ile Glu Phe Leu Lys Asn Gly Gly Pro Ser Ser Gly Ala Pro-NH$_2$ [SEQ ID NO. 171]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3746.1.

EXAMPLE 181

Preparation of Peptide having SEQ ID NO. 172

Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ ID NO. 172]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3742.1.

EXAMPLE 182

Preparation of Peptide having SEQ ID NO. 173

His Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala-NH$_2$ [SEQ ID NO. 173]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3693.1.

EXAMPLE 183

Preparation of Peptide having SEQ ID NO. 174

His Gly Glu Ala Thr Phe Thr Ser Asp Leu Ser Lys Gln Met Glu Glu Glu Ala Val Arg Leu Phe Ile Glu Trp Leu Lys Asn Gly Gly Pro Ser Ser Gly-NH$_2$ [SEQ ID NO. 174]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3751.2.

EXAMPLE 184

Preparation of Peptide having SEQ ID NO. 175

His Gly Glu Gly Thr Phe Thr Ser Ala Leu Ser Lys Gln Met Glu Glu Glu Ala Val Arg Leu Phe Ile Glu Trp Leu Lys Asn Gly Gly Pro Ser Ser-NH$_2$ [SEQ ID NO. 175]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3634.1.

EXAMPLE 185

Preparation of Peptide having SEQ ID NO. 176

Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser-NH$_2$ [SEQ ID NO. 176]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3526.9.

EXAMPLE 186

Preparation of Peptide having SEQ ID NO. 177

His Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser-NH$_2$ [SEQ ID NO. 177]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3477.9.

EXAMPLE 187

Preparation of Peptide having SEQ ID NO. 178

His Gly Glu Ala Thr Phe Thr Ser Asp Leu Ser Lys Gln Met Glu Glu Glu Ala Val Arg Leu Phe Ile Glu Trp Leu Lys Asn Gly Gly Pro-NH$_2$ [SEQ ID No. 178]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3519.9.

EXAMPLE 188

Preparation of Peptide having SEQ ID NO. 179
His Gly Glu Gly Thr Phe Thr Ser Ala Leu Ser Lys Gln Leu Glu Glu Glu Ala Val Arg Leu Phe Ile Glu Phe Leu Lys Asn Gly Gly-NH$_2$ [SEQ ID NO. 179]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3307.7.

EXAMPLE 189

Preparation of Peptide having SEQ ID NO. 180
Ala Gly Glu Gly Thr Phe Thr Ser Asp Leu Ser Lys Gln Leu Glu Glu Glu Ala Val Arg Leu Phe Ile Glu Phe Leu Lys Asn Gly-NH$_2$ [SEQ ID NO. 180]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN).

Analytical RP-HPLC (gradient 30% to 60% Solvent B in Solvent A over 30 minutes) of the lyophilized peptide is then carried out to determine the retention time of the product peptide. Electrospray Mass Spectrometry-(M): calculated 3186.5.

EXAMPLE 190

Preparation of Peptide having SEQ ID NO. 181
His Gly Ala Gly Thr Phe Thr Ser Asp Leu Ser Lys Gln Met Glu Glu Glu Ala Val Arg Leu Phe Ile Glu Trp Leu Lys Asn Gly Gly tPro Ser Ser Gly Ala tPro tPro tPro-NH$_2$ [SEQ ID NO. 181]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Double couplings are required at residues 37,36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4121.1.

EXAMPLE 191

Preparation of Peptide having SEQ ID NO. 182
His Gly Glu Ala Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala tPro tPro tPro-NH$_2$ [SEQ ID NO. 182].

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4173.2.

EXAMPLE 192

Preparation of Peptide having SEQ ID NO. 183
His Gly Glu Gly Thr Phe Thr Ser Ala Leu Ser Lys Gln Met Glu Glu Glu Ala Val Arg Leu Phe Ile Glu Trp Leu Lys Asn Gly Gly NMeala Ser Ser Gly Ala NMeala NMeala-NH$_2$ [SEQ ID NO. 183]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3796.1.

EXAMPLE 193

Preparation of Peptide having SEQ ID NO. 184
Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala hPro-NH$_2$ [SEQ ID NO. 184]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. A double coupling is required at residue 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3871.1.

EXAMPLE 194

Preparation of Peptide having SEQ ID NO. 185
His Gly Ala Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ ID NO. 185]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3750.2.

EXAMPLE 195

Preparation of Peptide having SEQ ID NO. 186
His Gly Asp Ala Thr Phe Thr Ser Asp Leu Ser Lys Gln Met Glu Glu Glu Ala Val Arg Leu Phe Ile Glu Trp Leu Lys Asn Gly Gly-NH$_2$ [SEQ ID NO. 186]

The above-identified amdiated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3408.8.

EXAMPLE 196

Preparation of Peptide having SEQ ID NO. 187
Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$ [SEQ ID NO. 187]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4120.6.

EXAMPLE 197

Preparation of Peptide having SEQ ID NO. 188
Ala Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-NH$_2$ [SEQ ID NO. 188]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4005.5.

EXAMPLE 198

Preparation of C-Terminal Carboxylic Acid Peptides Corresponding to the Above C-Terminal Amide Sequences for Peptides having SEQ ID NOs. 100–166, 172–177, 179–180 and 185–188.

C-terminal carboxylic acid peptides corresponding to amidated having SEQ ID NOS. 100–166, 172–177, 179–180 and 185–188 are assembled on the so called Wang resin (p-alkoxybenzylalacohol resin (Bachem, 0.54 mmole/g)) using Fmoc-protected amino acids (Applied Biosystems, Inc.), cleaved from the resin, deprotected and purified in a similar way to that described in Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLE 199

Preparation of C-Terminal Carboxylic Acid Peptides Corresponding to the Above C-Terminal Amide Sequences for Peptides having SEQ ID NOS. 167–171, 178 and 181–184.

C-terminal carboxylic acid peptides corresponding to amidated SEQ ID NOS. 167–171, 178 and 181–184 are assembled on the 2-chlorotritylchloride resin (200–400 mesh), 2% DVB (Novabiochem, 0.4–1.0 mmole/g)) using Fmoc-protected amino acids (Applied Biosystems, Inc.), cleaved from the resin, deprotected and purified in a similar way to that described in Example 109. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLES A TO E

Reagents Used

GLP-1[7-36]NH$_2$ (GLP-1) was purchased from Bachem (Torrance, Calif.). All other peptides were prepared using synthesis methods such as those described therein. All chemicals were of the highest commercial grade. The CAMP SPA immunoassay was purchased from Amersham. The radioligands were purchased from New England Nuclear (Boston, Mass.). RINm5f cells (American Type Tissue Collection, Rockville, Md.) were grown in DME/F12 medium containing 10% fetal bovine serum and 2 mM L-glutamine. Cells were grown at 37° C. and 5% $CO_2$/95% humidified air and medium was replaced every 2 to 3 days. Cells were grown to confluence then harvested and homogenized using on a Polytron homogenizer. Cell homogenates were stored frozen at −70° C. until used.

EXAMPLE A

GLP-1 Receptor Binding Studies

Receptor binding was assessed by measuring displacement of [$^{125}$I]GLP-1 or [$^{125}$I]exendin(9-39) from RINm5f membranes. Assay buffer contained 5 µg/ml bestatin, 1 µg/ml phosphoramidon, 1 mg/ml bovine serum albumin (fraction V), 1 mg/ml bacitracin, and 1 mM $MgCl_2$ in 20 mM HEPES, pH 7.4. To measure binding, 30 µg membrane protein (Bradford protein assay) was resuspended in 200 µl assay buffer and incubated with 60 pM [$^{125}$I]GLP-1 or [$^{125}$I]exendin(9-39) and unlabeled peptides for 120 minutes at 23 C in 96 well plates (Nagle Nunc, Rochester, N.Y.). Incubations were terminated by rapid filtration with cold phosphate buffered saline, pH 7.4, through polyethyleneimine-treated GF/B glass fiber filters (Wallac Inc., Gaithersburg, Md.) using a Tomtec Mach II plate harvester (Wallac Inc., Gaithersburg, Md.). Filters were dried, combined with scintillant, and radioactivity determined in a Betaplate liquid scintillant counter (Wallac Inc.).

Peptide samples were run in the assay as duplicate points at 6 dilutions over a concentration range of $10^{-6}$M to $10^{-12}$M to generate response curves. The biological activity of a sample is expressed as an $IC_{50}$ value, calculated from the raw data using an iterative curve-fitting program using a 4-parameter logistic equation (Prizm, GraphPAD Software).

EXAMPLE B

Cyclase Activation Study

Assay buffer contained 10 $\mu$M GTP, 0.75 mM ATP, 2.5 mM $MgCl_2$, 0.5 mM phosphocreatine, 12.5 U/ml creatine kinase, 0.4 mg/ml aprotinin, 1 $\mu$M IBMX in 50 mM HEPES, pH 7.4. Membranes and peptides were combined in 100 ml of assay buffer in 96 well filter-bottom plates (Millipore Corp., Bedford, Mass.). After 20 minutes incubation at 37° C., the assay was terminated by transfer of supernatant by filtration into a fresh 96 well plate using a Millipore vacuum manifold. Supernatant CAMP contents were quantitated by SPA immunoassay. Peptide samples were run in the assay as triplicate points at 7 dilutions over a concentration range of $10^{-6}$M to $10^{-12}$M to generate response curves. The biological activity of a particular sample was expressed as an $EC_{50}$ value, calculated as described above.

EXAMPLE C

Determination of Blood Glucose Levels in db/db Mice

C57BLKS/J-m-db mice at least 3 months of age were utilized for the study. The mice were obtained from The Jackson Laboratory and allowed to acclimate for at least one week before use. Mice were housed in groups of ten at 22° C.±1° C. with a 12:12 light:dark cycle, with lights on at 6 a.m. All animals were deprived of food for 2 hours before taking baseline blood samples. Approximately 70 $\mu$l of blood was drawn from each mouse via eye puncture, after a light anesthesia with metophane. After collecting baseline blood samples, to measure plasma glucose concentrations, all animals receive subcutaneous injections of either vehicle (10.9% NaCl), exendin-4 or test compound (1 $\mu$g) in vehicle. Blood samples were drawn again, using the same procedure, after exactly one hour from the injections, and plasma glucose concentrations were measured. For each animal, the % change in plasma value, from baseline value, was calculated.

EXAMPLE D

Dose Response Determination of Blood Glucose Levels in db/db Mice

C57BLKS/J-m-db/db mice, at least 3 months of age were utilized for the study. The mice were obtained from The Jackson Laboratory and allowed to acclimate for at least one week before use. Mice were housed in groups of ten at 22° C. ±1° C. with a 12:12 light:dark cycle, with lights on at 6 a.m. All animals were deprived of food for 2 hours before taking baseline blood samples. Approximately 70 $\mu$l of blood was drawn from each mouse via eye puncture, after a light anesthesia with metophane. After collecting baseline blood samples, to measure plasma glucose concentrations, all animals receive subcutaneous injections of either vehicle, exendin-4 or test compound in concentrations indicated. Blood samples were drawn again, using the same procedure, after exactly one hour from the injections, and plasma glucose concentrations were measured. For each animal, the % change in plasma value, from baseline value, was calculated and a dose dependent relationship was evaluated using Graphpad Prizm™ software.

EXAMPLE E

Gastric Emptying

The following study was and may be carried out to examine the effects of exendin-4 and/or an exendin agonist compound on gastric emptying in rats. This experiment followed a modification of the method of Scarpignato, et al., Arch. Int. Pharmacodyn. Ther. 246:286–94, 1980. Male Harlan Sprague Dawley (HSD) rats were used. All animals were housed at 22.7±0.8 C in a 12:12 hour light:dark cycle (experiments being performed during the light cycle) and were fed and watered ad libitum (Diet LM-485, Teklad, Madison, Wis.). Exendin-4 was synthesized according to standard peptide synthesis methods. The preparation of exendin-4 is described in Example 14. The determination of gastric emptying by the method described below was performed after a fast of ~20 hours to ensure that the stomach contained no chyme that would interfere with spectrophotometric absorbance measurements.

Conscious rats received by gavage, 1.5 ml of an acaloric gel containing 1.5% methyl cellulose (M-0262, Sigma Chemical Co, St Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In separate experiments on 7 rats, the stomach and small intestine were both excised and opened into an alkaline solution. The quantity of phenol red that could be recovered from the upper gastrointestinal tract within 20 minutes of gavage was 89±4%; dye which appeared to bind irrecoverably to the gut luminal surface may have accounted for the balance. To account for a maximal dye recovery of less than 100%, percent of stomach contents remaining after 20 min were expressed as a fraction of the gastric contents recovered from control rats sacrificed immediately after gavage in the same experiment. Percent gastric contents remaining= (absorbance at 20 min)/(absorbance at 0 mm)×100.

Various modifications of the invention in addition to those shown and described herein will become apparent to those skilled in the art from the foregoing description and fall within the scope of the following claims.

We claim:

1. A pharmaceutical formulation which is a liquid dosage form suitable for multi-use administration comprising about 0.005% to about 0.4% (w/v) of exendin-4, a buffer, an iso-osmolality modifier, and about 0.005% to about 1.0% (w/v) of a preservative selected from the group consisting of m-cresol, phenol, alcohol, methyl-, ethyl-, propyl- and butyl-paraben and any combination thereof, wherein said formulation has a pH of between about 3.0 and about 7.0.

2. The formulation of claim 1, said formulation having a pH of between about 4.0 and about 6.0.

3. The formulation of claim 1, wherein said exendin-4 is present at a concentration of between about 0.005% and about 0.05% (w/v).

4. The formulation of claim 1, wherein said buffer is selected from the group consisting of an acetate buffer, a glutamate buffer, a citrate buffer, a phosphate buffer, and any combination thereof.

5. The formulation of claim 1, wherein said buffer comprises an acetate buffer.

6. The formulation of claim 1, wherein said buffer comprises a glutamate buffer.

7. The formulation of claim 1, wherein said buffer comprises a citrate buffer.

8. The formulation of claim 1, wherein said buffer is at a concentration between about 0.002% and about 0.5% (w/v).

9. The formulation of claim 1, wherein said pH is between about 4.0 and about 5.0.

10. The formulation of claim 1, wherein said iso-osmolality modifier is a carbohydrate, a polyhydric alcohol, or a combination thereof, and said iso-osmolality modifier is at a concentration between about 1% and 10% (w/v).

11. The formulation of claim 10, wherein said polyhydric alcohol is selected from the group consisting of sorbitol, mannitol, inositol, glycerol, xylitol, polyethylene glycols, and any combination thereof.

12. The formulation of claim 10, wherein said carbohydrate is selected from the group consisting of galactose, arabinose, lactose, and any combination thereof.

13. The formulation of claim 1, wherein said iso-osmolality modifier is mannitol, sorbitol, or a combination thereof.

14. The formulation of claim 1, wherein said iso-osmolality modifier comprises mannitol.

15. The formulation of claim 1, wherein said iso-osmolality modifier comprises sorbitol.

16. The formulation of claim 1, wherein said preservative comprises m-cresol.

17. The formulation of claim 1, wherein said preservative comprises phenol.

18. The formulation of claim 1, wherein said formulation is suitable for administration via injection to achieve a dose of from about 0.1 µg/kg to about 0.5 µg/kg of said exendin-4.

19. The formulation of claim 1, wherein said formulation is suitable for administration via injection to achieve a dose of from about 0.005 µg/kg to about 0.2 µg/kg of said exendin-4.

20. The formulation of claim 1, wherein said formulation is suitable for administration via injection to achieve a dose of from about 1 µg/day to about 1 mg/day of said exendin-4.

21. A pharmaceutical formulation which is a liquid dosage form suitable for multi-use administration comprising 0.025% (w/v) of exendin-4, 0.159% (w/v) of an acetate buffer, 4.3% (w/v) mannitol, and 0.22% (w/v) m-cresol, wherein said formulation has a pH of 4.5.

22. A pharmaceutical formulation which is a liquid dosage form suitable for multi-use administration comprising exendin-4, a buffer, an iso-osmolality modifier, and about 0.005% to about 1.0% (w/v) of a preservative selected from the group consisting of m-cresol, phenol, alcohol, methyl-, ethyl-, propyl- and butyl-paraben and any combination thereof, wherein said formulation has a pH of between about 3.0 and about 6.0.

23. The formulation of claim 22, wherein said formulation is suitable for oral administration to achieve a dose of from about 500 µg/day to about 12,000 µg/day of said exendin-4 in a single or divided dose.

24. The formulation of claim 22, wherein said formulation is suitable for pulmonary administration to achieve a dose from about 100 µg/day to about 12,000 µg/day of said exendin-4 in a single or divided dose.

25. The formulation of claim 22, wherein said formulation is suitable for nasal administration to achieve a dose from about 10 µg/day to about 12,000 µg/day of said exendin-4 in a single or divided dose.

26. The formulation of claim 22, wherein said formulation is suitable for buccal administration to achieve a dose from about 100 µg/day to about 12,000 µg/day of said exendin-4 in a single or divided dose.

27. The formulation of claim 22, wherein said formulation is suitable for sublingual administration to achieve a dose from about 10 µg/day to about 8,000 µg/day of said exendin-4 in a single or divided dose.

28. The formulation of claim 22, said formulation having a pH of between about 4.0 and about 6.0.

29. The formulation of claim 22, wherein said pH is between about 4.0 and about 5.0.

30. The formulation of claim 22, wherein said buffer is selected from the group consisting of an acetate buffer, a glutamate buffer, a citrate buffer, a phosphate buffer, and any combination thereof.

31. The formulation of claim 22, wherein said buffer comprises an acetate buffer.

32. The formulation of claim 22, wherein said buffer comprises a glutamate buffer.

33. The formulation of claim 22, wherein said buffer comprises a citrate buffer.

34. The formulation of claim 22, wherein said buffer is at a concentration between about 0.02% and about 0.5% (w/v).

35. The formulation of claim 22, wherein said iso-osmolality modifier is a carbohydrate, a polyhydric alcohol, or a combination thereof, and said iso-osmolality modifier is at a concentration between about 1% and 10% (w/v).

36. The formulation of claim 35, wherein said polyhydric alcohol is selected from the group consisting of sorbitol, mannitol, inositol, glycerol, xylitol, polyethylene glycols, and any combination thereof.

37. The formulation of claim 35, wherein said carbohydrate is selected from the group consisting of galactose, arabinose, lactose, and any combination thereof.

38. The formulation of claim 22, wherein said iso-osmolality modifier is mannitol, sorbitol, or a combination thereof.

39. The formulation of claim 22, wherein said iso-osmolality modifier comprises mannitol.

40. The formulation of claim 22, wherein said iso-osmolality modifier comprises sorbitol.

41. The formulation of claim 22, wherein said preservative comprises m-cresol.

42. The formulation of claim 22, wherein said preservative comprises phenol.

* * * * *

UNITED STATES PATENT AND TRADEMARK OFFICE
CERTIFICATE OF CORRECTION

PATENT NO.       : 6,902,744 B1
APPLICATION NO.  : 09/889330
DATED            : June 7, 2005
INVENTOR(S)      : Orville G. Kolterman et al.

Page 1 of 1

It is certified that error appears in the above-identified patent and that said Letters Patent is hereby corrected as shown below:

In Column 91, lines 9-10, delete the text of Claim 8 beginning with "8. The formulation" and ending with "and about 0.5% (w/v)." and insert the following claim:

--8. The formulation of claim 1, wherein said buffer is at a concentration between about 0.02% and about 0.5% (w/v).--

Signed and Sealed this

Fifteenth Day of August, 2006

JON W. DUDAS
*Director of the United States Patent and Trademark Office*